United States Patent
Platzek et al.

(10) Patent No.: US 6,641,797 B2
(45) Date of Patent: Nov. 4, 2003

(54) PERFLUOROALKYL-CONTAINING COMPLEXES WITH SUGAR RADICALS, PROCESS FOR THEIR PRODUCTION AND THEIR USE

(75) Inventors: Johannes Platzek, Berlin (DE); Peter Mareski, Berlin (DE); Ulrich Niedballa, Berlin (DE); Bernd Raduechel, Berlin (DE); Hanns-Joachim Weinmann, Berlin (DE); Bernd Misselwitz, Glienicke (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/925,622

(22) Filed: Aug. 10, 2001

(65) Prior Publication Data

US 2002/0076379 A1 Jun. 20, 2002

Related U.S. Application Data

(60) Provisional application No. 60/234,952, filed on Sep. 26, 2000.

(30) Foreign Application Priority Data

Aug. 11, 2000 (DE) .......................... 100 40 381

(51) Int. Cl.⁷ .................. A61K 51/00; A61B 5/055; C07D 225/00
(52) U.S. Cl. ................. 424/1.65; 424/1.73; 424/9.36; 424/9.363; 424/9.364; 424/9.365; 424/9.4; 424/9.43; 540/465; 540/474
(58) Field of Search ................. 424/1.65, 1.73, 424/9.3, 9.36, 9.361, 9.363, 9.364, 9.4, 9.43, 9.44, 9.365; 534/10–16; 540/465, 470, 474

(56) References Cited

U.S. PATENT DOCUMENTS

| | | |
|---|---|---|
| 5,707,604 A | 1/1998 | Ranney |
| 5,804,163 A | 9/1998 | Gibby et al. |
| 5,863,518 A | 1/1999 | Hashiguchi et al. |

FOREIGN PATENT DOCUMENTS

| | | |
|---|---|---|
| DE | 689 01 924 T2 | 7/1992 |
| DE | 196 03 033 A | 7/1997 |
| DE | 690 32 374 T2 | 7/1998 |
| DE | 197 29 013 A1 | 2/1999 |
| DE | 197 28 954 C1 | 4/1999 |
| DE | 199 14 101 C1 | 10/2000 |
| EP | 0 707 857 A | 4/1996 |
| EP | 1 088 558 A2 | 4/2001 |
| WO | WO 97/26017 | 7/1997 |
| WO | WO 99/01161 A | 1/1999 |
| WO | WO 99/32154 A | 7/1999 |

Primary Examiner—Michael G. Hartley
(74) Attorney, Agent, or Firm—Millen, White, Zelano & Branigan, P.C.

(57) ABSTRACT

Perfluoroalkyl-containing complexes with sugar radicals of general formula I

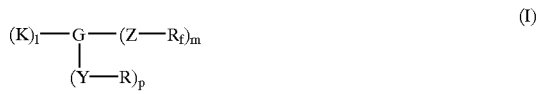

in which R represents a monosaccharide or oligosaccharide radical that is bonded via the 1-OH position or 1-SH position, $R_f$ means a perfluorinated carbon chain, K is a metal complex, and Y and Z represent linker groups, are suitable for intravenous lymphography, for tumor diagnosis and for infarction and necrosis imaging.

26 Claims, No Drawings

PERFLUOROALKYL-CONTAINING COMPLEXES WITH SUGAR RADICALS, PROCESS FOR THEIR PRODUCTION AND THEIR USE

This application claims priority to provisional application No. 60/234,952, filed Sep. 26, 2000.

The invention relates to the subjects that are characterized in the claims, namely perfluoroalkyl-containing metal complexes with sugar radicals of general formula I, process for their production and their use in NMR diagnosis and x-ray diagnosis, radiodiagnosis and radiotherapy, in MRT-lymphography and as blood-pool agents. The compounds according to the invention are quite especially suitable for intravenous lymphography, for tumor diagnosis and for infarction and necrosis imaging.

In nuclear magnetic resonance, the element fluorine is second in importance to the element hydrogen.

1) Fluorine has a high sensitivity of 83% of that of hydrogen.
2) Fluorine has only one NMR-active isotope.
3) Fluorine has a resonance frequency that is similar to hydrogen—fluorine and hydrogen can be measured with the same system.
4) Fluorine is biologically inert.
5) Fluorine does not occur in biological material (exception: teeth) and can therefore be used as a probe or contrast medium against a background that is free of interfering signals.

The effect of these properties is that fluorine occupies a broad space in diagnostic patent literature with magnetic nuclear resonance as a basis: fluorine-19-imaging, functional diagnosis, spectroscopy.

U.S. Pat. No. 4,639,364 (Mallinckrodt) thus proposes trifluoromethanesulfonamides as contrast media for fluorine-19-imaging:

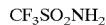

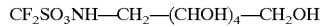

German Patent DE 4203254 (Max-Planck-Gesellschaft), in which an aniline derivative is proposed:

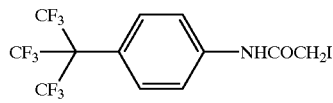

also relates to fluorine-19-imaging.

Fluorine-19-imaging is the subject of Application WO 93/07907 (Mallinckrodt), in which phenyl derivatives are also claimed as contrast media:

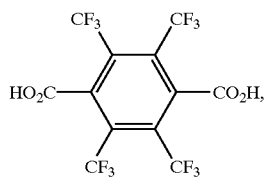

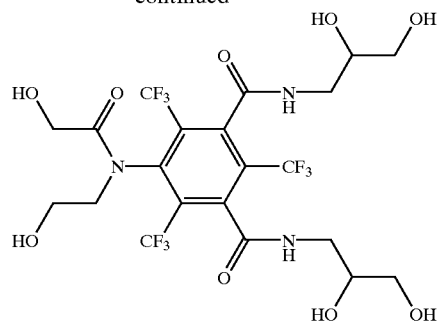

For fluorine-19-imaging, compounds of considerably simpler structure are also claimed. Thus, U.S. Pat. No. 4,586,511 (Children's Hospital Medical Center) mentions perfluorooctylbromide

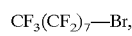

European Patent EP 307863 (Air Products) mentions perfluoro-15-crown-5-ether

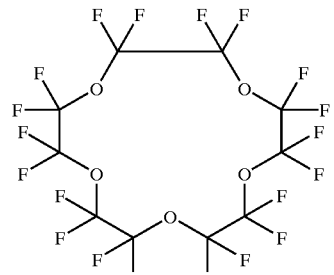

and U.S. Pat. No. 4,588,279 (University of Cincinnati, Children's Hospital Research Foundation) mentions perfluorocarbon compounds such as perfluorocyclononane or -octane, perfluorinated ethers such as tetrahydrofuran

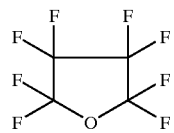

or diethers such as perfluoropropylene glycol-diether

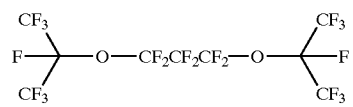

The compounds that are mentioned in Application WO 94/22368 (Molecular Biosystems), e.g.,

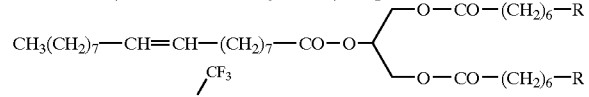

which as

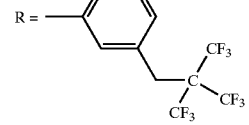

fluorine-containing radicals have the perfluorine-1H group or 1H-neopentyl group, are also used for fluorine-19-imaging.

U.S. Pat. No. 5,362,478 (VIVORX) indicates another structural type with expanded diagnostic use, in which the fluorocarbon/polymer shell combination is claimed for imaging purposes. Perfluorononane and human serum albumin are mentioned. This combination proves suitable, moreover, for using the fluorine atom as a probe for local temperature measurement and for determining the partial oxygen pressure.

Perfluorocarbons are also claimed in U.S. Pat. No. 4,586,511 for oxygen determination.

In German Patent DE 4008179 (Schering), fluorine-containing benzenesulfonamides are claimed as pH probes:

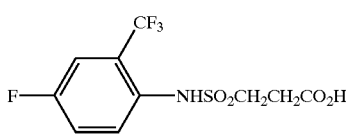

For NMR diagnosis, compounds that contain iodine and fluorine atoms are also claimed as contrast-enhancing agents in WO 94/05335 and WO 94/22368 (both molecular biosystems):

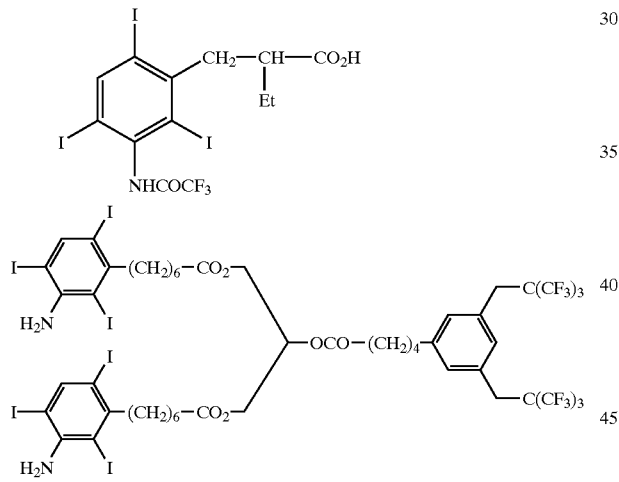

The fluorine-paramagnetic metal ion combination is also claimed for fluorine-19-imaging, specifically for open-chain complexes in WO 94/22368 (Molecular Biosystems) with, e.g.:

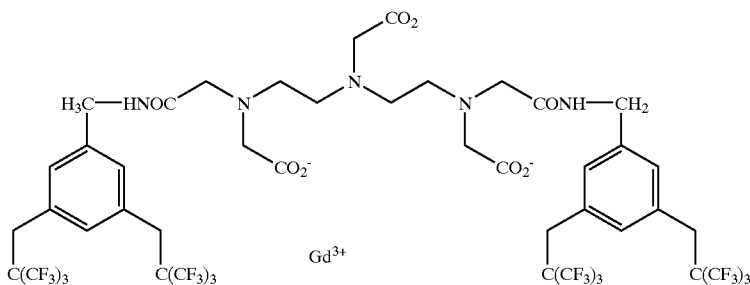

and in EP 292 306 (TERUMO Kabushiki Kaisha) with, e.g.:

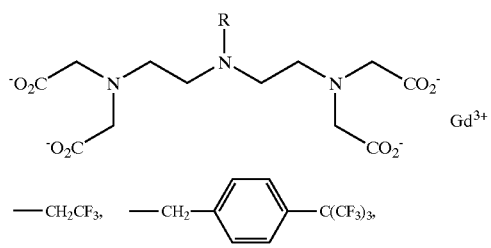

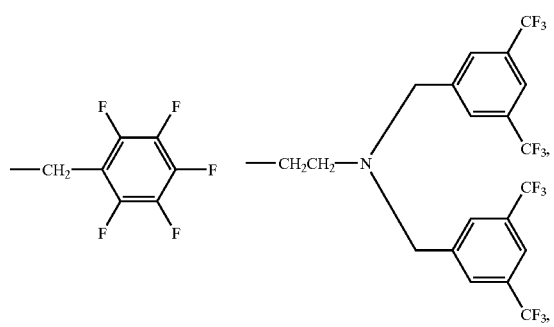

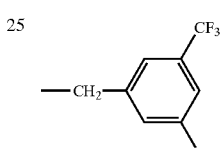

but also for cyclic compounds, as they are mentioned in EP 628 316 (TERUMO Kabushiki Kaisha)

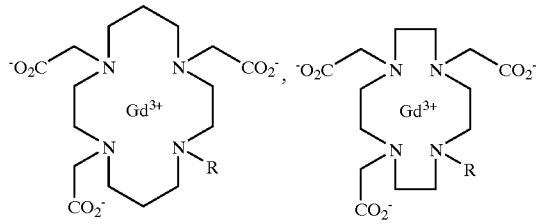

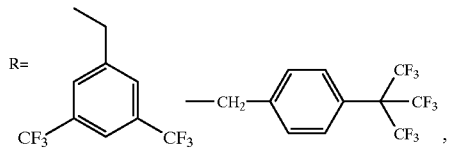

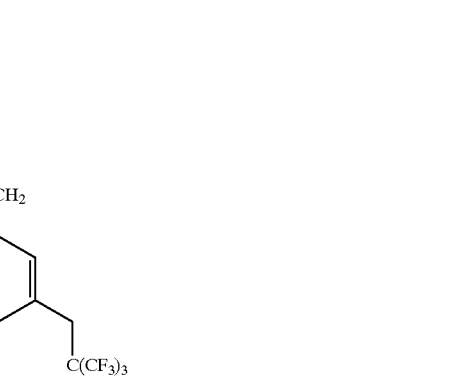

-continued

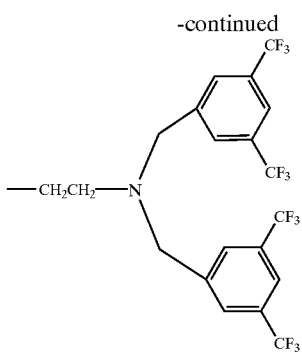

The combination of fluorine atom and rare-earth metal is also claimed for NMR-spectroscopic temperature measurements in DE 4317588 (Schering):

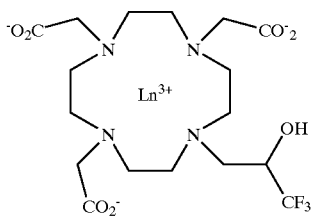

Ln: Rare earths: La, Pr, Dy, Eu

While no interactions occur between the two nuclei in compounds that contain the elements fluorine and iodine, intensive interaction does occur in compounds that contain fluorine and paramagnetic centers (radicals, metal ions) and that are expressed in a shortening of the relaxation time of the fluorine nucleus. The extent of this effect depends on the number of unpaired electrons of the metal ion ($Gd^{3+}$>$Mn^{2+}$>$Fe^{3+}$>$Cu^{2+}$) and on the removal between the paramagnetic ion and the $^{19}F$-atom.

The more unpaired electrons of the metal ion are present and the closer the latter are brought to the fluorine, the greater the shortening of the relaxation time of the fluorine nucleus.

The shortening of the relaxation time as a function of the distance from the paramagnetic ion becomes apparent in all nuclei with an uneven spin number, thus also in the case of protons, and gadolinium compounds are therefore widely used as contrast media in nuclear spin tomography (Magnevist[R], Prohance[R], Omniscan[R], and Dotarem[R]).

In $^1H$-MR imaging ($^1H$-MRI), however, relaxation time $T^1$ or $T^2$ of the protons, i.e., mainly the protons of water, and not the reaction time of the fluorine nuclei, is measured and used for imaging. The quantitative measurement for the shortening of the relaxation time is relaxivity [L/mmol·s]. Complexes of paramagnetic ions are successfully used for shortening relaxation times. In the following table, the relaxivity of several commercial preparations is indicated:

| | $T^1$-Relaxivity in Water [L/mmoL s, 39° C., 0.47 T] | $T^1$-Relaxivity in Plasma [L/mmol s, 39° C., 0.47 T] |
|---|---|---|
| MAGNEVIST[R] | 3.8 | 4.8 |
| DOTAREM[R] | 3.5 | 4.3 |
| OMNISCAN[R] | 3.8 | 4.4 |
| PRO HANCE[R] | 3.7 | 4.9 |

Only interactions between protons and the gadolinium ion are found-in these compounds. For these contrast media in water, a relaxivity of about 4 [L/mmol·s] is thus observed.

Both fluorine compounds for fluorine-19-imaging, in which the shortened relaxation time of the fluorine nucleus is used, and non-fluorine-containing compounds, in which the relaxation time of protons of water is measured, are thus used successfully for MR imaging.

In the introduction of a perfluorocarbon-containing radical into a paramagnetic contrast medium, i.e., in the combination of properties that were previously known as suitable only for fluorine-imaging compounds, the relaxivity that relates to the protons of water also quickly increases, surprisingly enough, with compounds that were used for proton imaging. It now reaches values of 10–50 [L/mmol·s] in comparison to values of between 3.5 and 3.8 [L/mmol·s] as they were already cited for a few commercial products in the table above.

Perfluoroalkyl-containing metal complexes are already known from DE 196 03 033.1. These compounds, however, cannot be used satisfactorily for all applications. Thus, there is still a need for contrast media for the visualization of malignant tumors, lymph nodes and necrotic tissue.

Malignant tumors metastasize in clusters in regional lymph nodes, whereby multiple lymph node stations may also be involved. Lymph node metastases thus are found in about 50–69% of all patients with malignant tumors (Elke, Lymphographie (Lymphography), in: Frommhold, Stender, Thurn (eds.), Radiologische Diagnostik in Klinik und Praxis [Radiological Diagnosis in Clinical Studies and in Practice], Volume IV, Thieme Verlag Stuttgart, 7th Ed., 434–496, 1984.). The diagnosis of a metastatic attack of lymph nodes is of great importance with respect to the treatment and prognosis of malignant types of diseases. With modern imaging methods (CT, US and MRI), lymphogenous evacuations of malignant tumors are detected only inadequately, since in most cases only the size of the lymph node can be used as a diagnostic criterion. Thus, small metastases in non-enlarged lymph nodes (<2 cm) cannot be distinguished from lymph node hyperplasias without a malignant attack (Steinkamp et al., Sonographie und Kernspintomographie: Differentialdiagnostik von reaktiver Lymphknoten-vergröSerung und Lymphknoten-metastasen am Hals [Sonography and Nuclear Spin Tomography: Differential Diagnosis of Reactive Lymph Node Enlargement and Lymph Node Metastasis on the Neck], Radiol. Diagn. 33:158, 1992).

It would be desirable if a distinction could be made when using specific contrast media lymph nodes with metastatic attack and hyperplastic lymph nodes.

Direct x-ray lymphography (injection of an oily contrast medium suspension into a prepared lymph vessel) is known as an invasive method that is used only very rarely and that can visualize only small lymph drainage stations.

Fluorescence-labeled dextrans are also used experimentally in animal experiments to be able to observe lymphatic drainage after their interstitial administration. All commonly used markers for the visualization of lymph tracts and lymph nodes after interstitial/intracutaneous administration have in common the fact that they are substances with particulate character ("particulates," e.g., emulsions and nanocrystal suspensions) or large polymers (see above, WO 90/14846). Based on their inadequate local and systemic compatibility as well as their small lymphatic passageway, which causes inadequate diagnostic efficiency, the previously described preparations still do not prove optimally suitable for indirect lymphography, however.

Since the visualization of lymph nodes is of central importance for the early detection of metastatic attack in cancer patients, there is a great need for lymph-specific contrast medium preparations for diagnosis of corresponding changes of the lymphatic system.

The highest possible contrast medium concentration and high stability are just as desirable as the diagnostically relevant, most uniform possible lymphatic concentration over several lymph stations. The burden on the overall organism should be kept low by quick and complete excretion of the contrast medium. A quick start-up, if possible as early as within a few hours after the administration of contrast media, is important for the radiological practice. Good compatibility is necessary. a possible lymph node metastasizing to be visualized.

Another important area in medicine is the detection, localization and monitoring of necroses or infarctions. Thus, myocardial infarction is not a stationary process, but rather a dynamic process, which extends over a long period (weeks to months). The disease proceeds in about three phases, which are not strictly separated from one another, but rather are overlapping. The first phase, the development of myocardial infarction, comprises the 24 hours after the infarction, in which the destruction from the subendocardium to the myocardium progresses like a shock wave (wave front phenomenon). The second phase, the already existing infarction, comprises the stabilization of the area in which fiber formation (fibrosis) takes place as a healing process. The third phase, the healed infarction, begins after all destroyed tissue is replaced by fibrous scar tissue. During this period, an extensive restructuring takes place.

Up until now, no precise and reliable process is known that enables the current phase of a myocardial infarction to be diagnosed in a living patient. To evaluate a myocardial infarction, it is of decisive importance to know how large the proportion of the tissue that is lost in the infarction is and at what point the loss took place, since the type of therapy depends on this knowledge.

Infarctions take place not only in the myocardium, but rather also in other tissues, especially in the brain.

While the infarction can be healed to a certain extent, in a necrosis, locally limited tissue death, only the harmful sequelae for the residual organism can be prevented or at least reduced. Necroses can develop in many ways: by traumas, chemicals, oxygen deficiency or by radiation. As in infarction, the knowledge of the extent and type of a necrosis is important for further medical treatment.

Tests to improve the localization of infarctions and necroses by using contrast media in non-invasive processes, such as scintigraphy or nuclear spin tomography, therefore already took place earlier. The literature is full of reports on attempts to use porphyrins for necrosis imaging. The results that are achieved, however, paint a contradictory picture. Winkelman and Hoyes thus describe in Nature, 200, 903 (1967) that manganese-5,10,15,20-tetrakis(4-sulfonatophenyl)-porphyrin (TPPS) selectively accumulates in the necrotic portion of a tumor.

Lyon et al. (Magn. Res. Med. 4, 24 (1987)) observed, however, that manganese-TPPS is dispersed in the body, specifically in the kidney, liver, tumor and only in a small portion of the muscles. In this case, it is advantageous that the concentration in the tumor reaches its maximum only on the fourth day and only after the authors had increased the dose from 0.12 mmol/kg to 0.2 mmol/kg. The authors therefore also speak of a non-specific take-up of TPPS in the tumor. Bockhurst et al. in turn report in Acta Neurochir 60, 347 (1994, Suppl.) that MnTPPS binds selectively to tumor cells.

Foster et al. (J. Nucl. Med. 26, 756 (1985)) in turn found that $^{111}$In-5,10,15,20-tetrakis-(4-N-methyl-pyridinium)-porphyrin (TMPyP) does not accumulate in the necrotic portion, but rather in the living edge layers. It follows from the above that a porphyrin-tissue interaction exists and is obvious but not necessary.

In Circulation Vol. 90, No. 4, part 2, page 1468, Abstract No. 2512 (1994), Ni et al. report that they can visualize infarction areas with a manganese-tetraphenyl-porphyrin (Mn-TPP) and a gadolinium-mesoporphyrin (Gd-MP). In International Patent Application WO 95/31219, both substances were used in infarction and necrosis imaging. Authors Marchal and Ni write (see Example 3) that for the compound Gd-MP, the metal content of the infarction-kidney was high, similar to that of the non-infarcted organ, but that it was nine times as large for the myocardium in the case of infarcted tissue (Example 1). It was surprising that the ratio of the signal intensities in MRI for infarcted patients was comparatively high in comparison to healthy tissue in both cases with 2.10 or 2.19. Other metalloporphyrins have been described in Application DE 19835082 (Schering AG).

Porphyrins tend to be stored in the skin, which results in a photosensitization. The sensitization can last for days, and even weeks. This in an undesirable side-effect in using porphyrins as diagnostic agents. In addition, the therapeutic index for the porphyrins is only very small, since, e.g., for Mn-TPPS, an action is used only at a dose of 0.2 mmol/kg, but $LD_{50}$ is already approximately 0.5 mmol/kg.

Contrast media for necrosis and infarction imaging that are not derived from the porphyrin skeleton are described in DE 19744003 (Schering AG), DE 19744004 (Schering AG) and WO 99/17809 (EPIX). To date, however, there are still no compounds that can be used satisfactorily as contrast media in infarction and necrosis imaging.

The object of the invention was therefore to make available contrast media that can be used in particular for MRT-lymphography, but also for tumor diagnosis and necrosis and infarction imaging.

The object of the invention is achieved by the perfluoroalkyl-containing complexes with sugar radicals of general formula I

in which

R represents a monosaccharide or oligosaccharide radical that is bonded via the 1-OH position or 1-SH position, $R_f$ is a perfluorinated, straight-chain or branched carbon chain with the formula $—C_nF_{2n}E$, in which E represents a terminal fluorine, chlorine, bromine, iodine or hydrogen atom, and n stands for numbers 4–30, K stands for a metal complex of general formula II

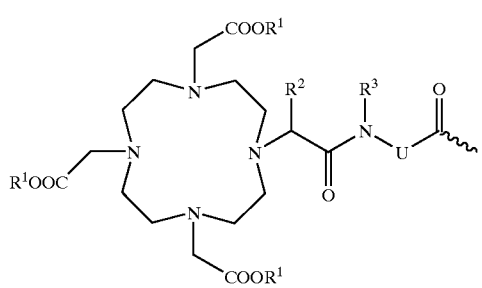

(II)

in which

R¹ means a hydrogen atom or a metal ion equivalent of atomic numbers 21–29, 31–33, 37–39, 42–44, 49 or 57–83, provided that at least two R¹ stand for metal ion equivalents, R² and R³, independently of one another, represent hydrogen, $C_1$–$C_7$ alkyl, benzyl, phenyl, —$CH_2OH$ or —$CH_2OCH_3$, and U represents —$C_6H_4$—O—$CH_2$-ω-, —$(CH_2)_{1-5}$-ω, a phenylene group, —$C_6H_4$—$(OCH_2CH_2)_{0-1}$—, $N(CH_2COOH)$—$CH_2$-ω or a $C_1$–$C_{12}$ alkylene group or a $C_7$—$C_{12}$—$C_6H_4$—O group that is optionally interrupted by one or more oxygen atoms, 1 to 3 —NHCO groups or 1- to 3 —CONH groups and/or is substituted with 1 to 3 —$(CH_2)_{0-5}$COOH groups, whereby ω stands for the binding site to —CO—, or of general formula III

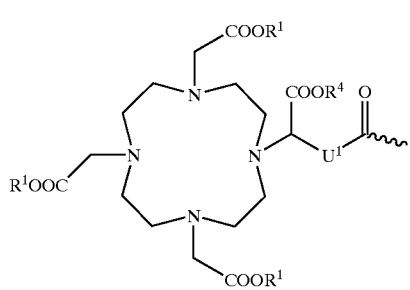

(III)

in which R¹ has the above-mentioned meaning, R⁴ represents hydrogen or a metal ion equivalent that is mentioned under R¹, and U¹ represents —$C_6H_4$—O—$CH_2$-ω-, whereby ω means the binding site to —CO— or of general formula IV

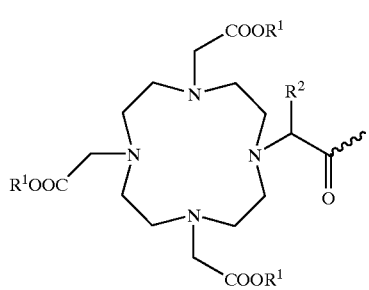

(IV)

in which R¹ and R² have the above-mentioned meaning or of general formula V A or V B

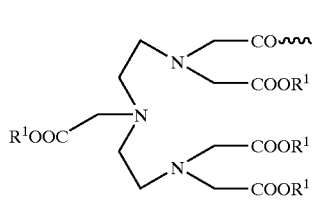

(VA)

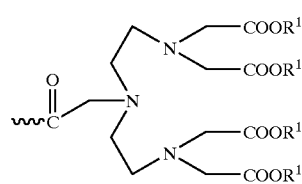

(VB)

in which R¹ has the above-mentioned meaning, or of general formula VI

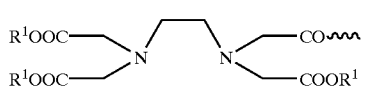

(VI)

in which R¹ has the above-mentioned meaning, or of general formula VII

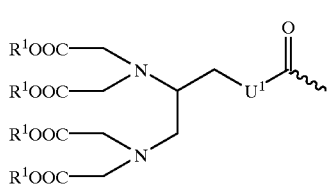

(VII)

in which R¹ has the above-mentioned meaning, and

U¹ represents —$C_6H_4$—O—$CH_2$-ω-, whereby ω means the binding site to —CO—, or of general formula VIII

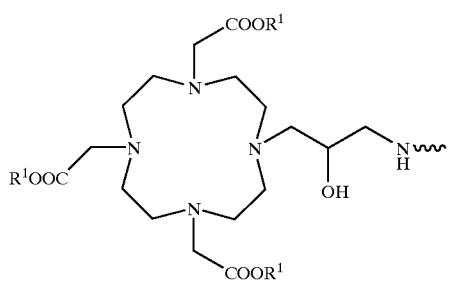

(VIII)

in which R¹ has the above-mentioned meaning, and in radical K, optionally present free acid groups optionally can be present as salts of organic and/or inorganic bases or amino acids or amino acid amides, G for the case that K means metal complexes II to VII represents a radical that is functionalized in at least three places and that is selected from radicals a) to j) below (a) 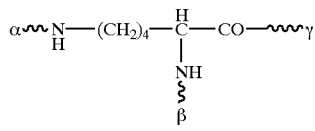

(b) 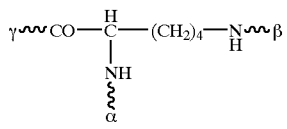

(c) 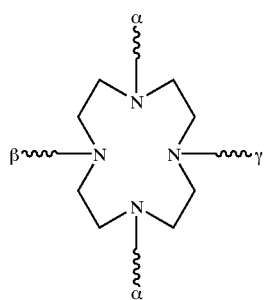

(d) 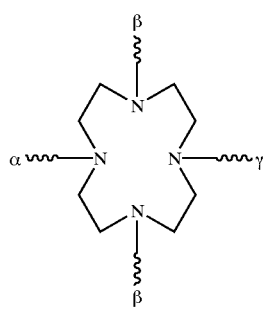

(e) 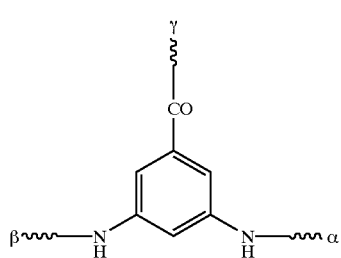

(f) 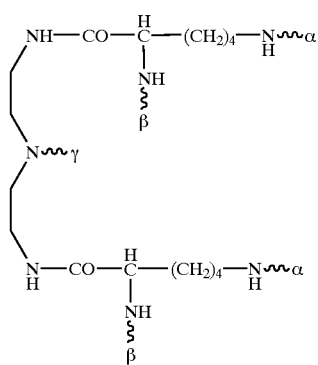

(g) 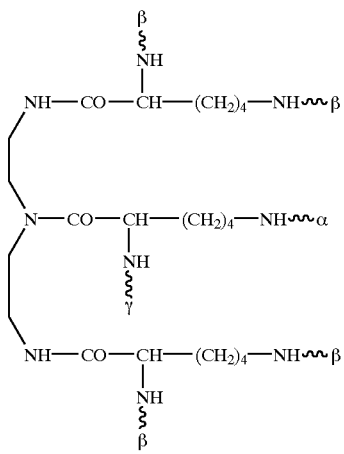

(h) 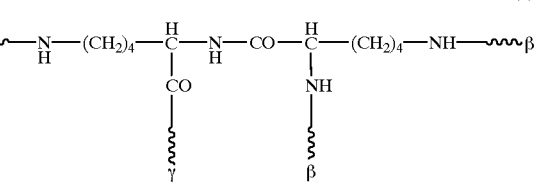

(i) 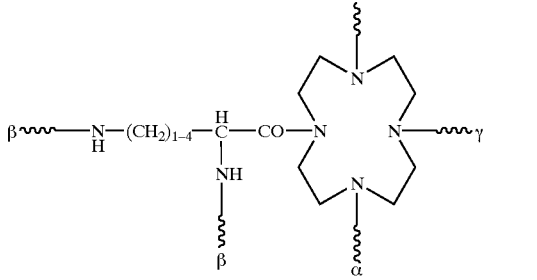

(j) 

and

G for the case that K means metal complex VIII represents a radical that is functionalized in at least three places and that is selected from k) or l), (k) 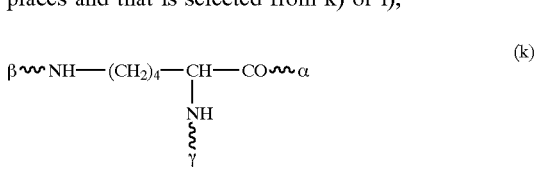

(l) 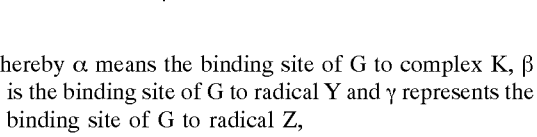

whereby α means the binding site of G to complex K, β is the binding site of G to radical Y and γ represents the binding site of G to radical Z, Y means —CH$_2$, δ-(CH$_2$)$_n$CO-β (whereby n=1–5), δ-CH$_2$—CHOH—CO-β or δ-CH(CHOH—CH$_2$OH)—CHOH—CHOH—CO-β, whereby δ represents the binding site to sugar radical R and β is the binding site to radical G Z stands for

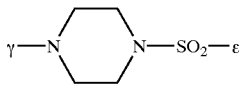

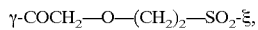

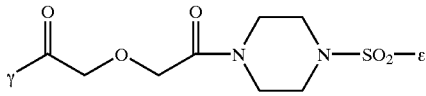

or

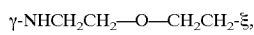

whereby γ represents the binding site of Z to radical G, and

ξ means the binding site of Z to perfluorinated radical $R_f$, and l, m, independently of one another, mean the whole numbers and p means the whole numbers 1 to 4.

If the compound according to the invention is intended for use in NMR diagnosis, the metal ion of the signal-transmitting group must be paramagnetic. These are especially the divalent and trivalent ions of the elements of atomic numbers 21–29, 42, 44 and 58–70. Suitable ions are, for example, the chromium(III) ion, iron(II) ion, cobalt(II) ion, nickel(II) ion, copper(II) ion, praseodymium(III) ion, neodymium(III) ion, samarium(III) ion and ytterbium(III) ion. Because of their strong magnetic moment, gadolinium (III), terbium(III), dysprosium(III), holmium(III), erbium (III), iron(III) and manganese(II) ions are especially preferred.

For the use of the compounds according to the invention in nuclear medicine (radiodiagnosis and radiotherapy), the metal ion must be radioactive. For example, radioisotopes of the elements with atomic numbers 27, 29, 31–33, 37–39, 43, 49, 62, 64, 70, 75 and 77 are suitable. Technetium, gallium, indium, rhenium, and yttrium are preferred.

If the compound according to the invention is intended for use in x-ray diagnosis, the metal ion is preferably derived from an element of a higher atomic number to achieve a sufficient absorption of x-rays. It was found that diagnostic agents that contain a physiologically compatible complex salt with metal ions of elements of atomic numbers 25, 26 and 39 as well as 57–83 are suitable for this purpose.

Manganese(II), iron(II), iron(III), praseodymium(III), neodymium(III), samarium(III), gadolinium(III), ytterbium (III) or bismuth(III) ions, especially dysprosium(III) ions and yttrium(III) ions, are preferred.

Acidic hydrogen atoms that are optionally present in $R^1$, i.e., those that have not been substituted by the central ion, can optionally be replaced completely or partially by cations of inorganic and/or organic bases or amino acids or amino acid amides.

Suitable inorganic cations are, for example, the lithium ion, the potassium ion, the calcium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine, and ornithine as well as the amides of otherwise acidic or neutral amino acids.

Especially preferred compounds of general formula I are those with macrocycle K of general formula II.

Radical U in metal complex K preferably means —CH$_2$— or C$_6$H$_4$—O—CH$_2$-ω, whereby ω stands for the binding site to —CO—.

Alkyl groups $R^2$ and $R^3$ in the macrocycle of general formula II can be straight-chain or branched. By way of example, methyl, ethyl, propyl, isopropyl, n-butyl, 1-methylpropyl, 2-methylpropyl, n-pentyl, 1-methylbutyl, 2-methylbutyl, 3-methylbutyl, and 1,2-dimethylpropyl can be mentioned. $R^2$ and $R^3$, independently of one another, preferably mean hydrogen or $C_1$–$C_4$ alkyl.

In a quite especially preferred embodiment, $R^2$ stands for methyl and $R^3$ stands for hydrogen.

The benzyl group or the phenyl group $R^2$ or $R^3$ in macrocycle K of general formula II can also be substituted in the ring.

Radical R in general formula I means a monosaccharide or oligosaccharide radical or thio sugar radical bonded via the 1-OH position or 1-SH position, whereby in this connection according to the invention, this can also be deoxy sugars that contain an H atom instead of one or more OH groups. In a preferred embodiment of the invention, R means a monosaccharide radical with 5 or 6 C atoms, preferably glucose, mannose, galactose, ribose, arabinose or xylose or their deoxy sugars, such as, for example, 6-deoxygalactose (fucose) or 6-deoxymannose (rhamnose) or their thio sugars, whereby glucose, mannose and galactose are especially preferred.

Of the compounds of general formula I according to the invention, in addition those are preferred in which $R_f$ means —C$_n$F$_{2n+1}$. n preferably stands for the numbers 4–15. Quite especially preferred are radicals —C$_4$F$_9$, —C$_6$F$_{13}$, —C$_8$F$_{17}$, —C$_{12}$F$_{25}$ and —C$_{14}$F$_{29}$ as well as the radicals of the compounds that are mentioned in the examples.

Radical G that is functionalized in at least three places in general formula I, which represents the "skeleton," means lysine radical (a) or (b) in a preferred embodiment of the invention.

Y and Z mean the linkers indicated in general formula I, whereby independently of one another, the radical

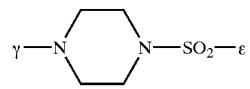

is preferred for Z and the radical δ-CH$_2$CO-β is preferred for Y.

The perfluoroalkyl-containing metal complexes with sugar radicals of general formula I

with K in the meaning of a metal complex of general formulas II to VII and G in the meaning of formulas a) to j), in which Y, Z, R, $R_f$, m, p and l have the above-mentioned meaning, are produced, in a way that is known in the art, by a carboxylic acid of general formula IIa

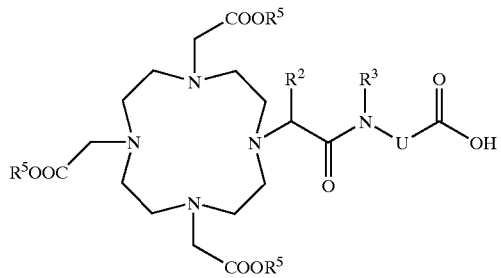

(IIa)

in which $R^5$ means a metal ion equivalent of atomic numbers 21–29, 31–33, 37–39, 42–44, 49 or 57–83 or a carboxyl protective group,
and $R^2$, $R^3$ and U have the above-mentioned meaning,
or a carboxylic acid of general formula IIIa

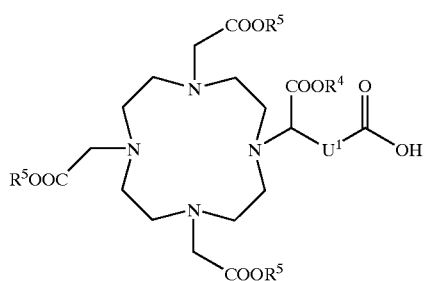

(IIIa)

in which $R^4$, $R^5$, and $U^1$, have the above-mentioned meaning
or a carboxylic acid of general formula IVa

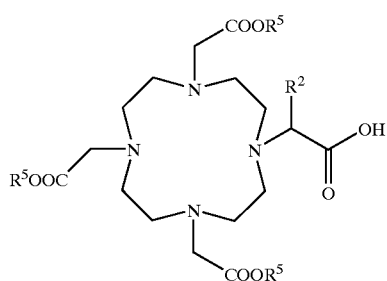

(IVa)

in which $R^5$ and $R^2$ have the above-mentioned meaning
or a carboxylic acid of general formula Va or Vb

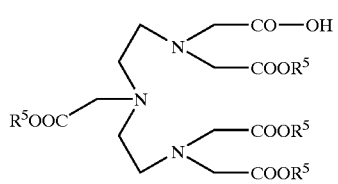

(Va)

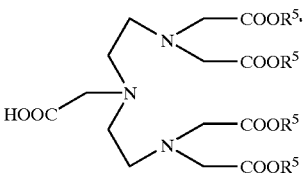

(Vb)

in which $R^5$ has the above-mentioned meaning
or a carboxylic acid of general formula VIa

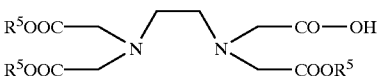

(VIa)

in which $R^5$ has the above-mentioned meaning
or a carboxylic acid of general formula VIIa

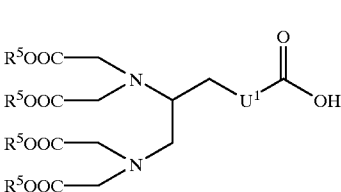

(VIIa)

in which $R^5$ and $U^1$ have the above-mentioned meanings, being reacted in optionally activated form with an amine of general formula IX

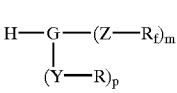

(IX)

in which G has the meaning of formulas a) to j), and R, $R_f$, Y, Z, m and p have the indicated meaning, in a coupling reaction and optionally subsequent cleavage of optionally present protective groups into a metal complex of general formula I, or if $R^5$ has the meaning of a protective group, being reacted after cleavage of these protective groups in a subsequent step in a way that is known in the art with at least one metal oxide or metal salt of an element of atomic numbers 21–29, 31–33, 37–39, 42–44, 49 or 57–83, and then, if desired, optionally present, acidic hydrogen atoms being substituted by cations of inorganic and/or organic bases, amino acid or amino acid amides.

The compounds of general formula I according to the invention with K in the meaning of a metal complex of general formula VIII and G in the meaning of formulas k) or l) are produced in a way that is known in the art by an amine of general formula VIIIa

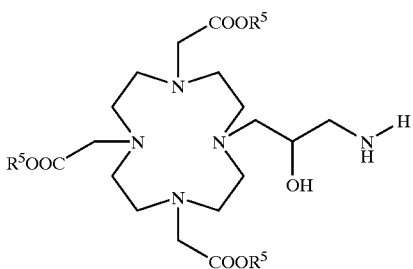

(VIIIa)

in which R means a metal ion equivalent of atomic numbers 21–29, 31–33, 37–39, 42–44, 49 or 57–83, or a carboxyl protective group, being reacted with an optionally activated carboxylic acid of general formula X

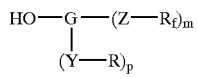

(X)

in which G has the meaning of formulas k) or l) and R, $R_f$, Y, Z, m and p have the indicated meanings, in a coupling reaction and optionally subsequent cleavage of optionally present protective groups to a metal complex of general formula I or if $R^5$ has the meaning of a protective group, being reacted after cleavage of these protective groups in a subsequent step in a way that is known in the art with at least one metal oxide or metal salt of an element of atomic numbers 21–29, 31–33, 37–39, 42–44, 49 or 57–83, and then, if desired, optionally present acid hydrogen atoms being substituted by cations of inorganic and/or organic bases, amino acids or amino acid amides.

The carboxylic acids of general formulas IIa to VIIa that are used are either known compounds or are produced according to the process described in the examples. Thus, the production of carboxylic acids of general formula IIa is known from DE 196 52 386. The production of carboxylic acids of general formula IIIa can be carried out analogously to Example 3 of this application. The production of the carboxylic acids of general formula IVa can be derived from DE 197 28 954.

A precursor for compounds of general formula VA is $N^3$-(2,6-dioxomorpholinoethyl)-$N^6$-(ethoxycarbonylmethyl)-3,6-diaza-octanedioic acid, which is described in EP 263 059.

The compounds of general formula VD are derived from the isomeric diethylenetriamine-pentaacetic acid, which binds via the acetic acid that is on the center N atom. This DTPA is described in Patents DE 195 07 819 and DE 195 08 058.

Compounds of general formula VI are derived from N-(carboxymethyl)-N-[2-(2,6-dioxo-4-morpholinyl)-ethyl]-glycine, whose production is described in J. Am. Oil. Chem. Soc. (1982), 59 (2), 104–107.

Compounds of general formula VII are derived from 1-(4-carboxymethoxybenzyl)-ethylenediamine-tetraacetic acid, whose production is described in U.S. Pat. No. 4,622,420.

The production of amines of general formula IX and carboxylic acids of general formula X is described in detail in the examples of this application and can be carried out analogously to the processes described in the examples. The amine of general formula VIIIa is a known starting compound.

The perbenzylated sugar acids used as starting substances can be produced analogously to Lockhoff, Angew. Chem. [Applied Chem.] 1998, 110, No. 24, p. 3634 ff. Thus, e.g., the production of the 1-O-acetic acid of perbenzyl-glucose is carried out over 2 stages, via trichloroacetamidate and reaction with hydroxyacetic acid ethyl ester, $BF_3$-catalysis in THF and subsequent saponification with NaOH in MeOH/THF.

In a more advantageous process, the perbenzylated sugar acids that are used as starting substances can also be produced by the perbenzylated 1-OH-sugar being dissolved in a water-immiscible organic solvent and being reacted with an alkylating reagent of general formula XI Nu-L—COO-Sg (XI), in which Nu means a nucleofuge, L is —$(CH_2)$—$_n$, (whereby n=1–5), —$CH_2$—CHOH—, —CH(CHOH—$CH_2OH$)—CHOH—CHOH—, and Sg represents a protective group, in the presence of a base and optionally a phase transfer catalyst. As nucleofuges, for example, the radicals —Cl, —Br, —I, OTs, —OMs, —$OSO_2CF_3$, —$OSO_2C_4F_9$ or —$OSO_2C_8F_{17}$ can be contained in the alkylating reagent of general formula XI.

The protective group is a conventional acid protective group. These protective groups are well known to one skilled in the art (Protective Groups in Organic Syntheses, Second Edition, T. W. Greene and P. G. M. Wuts, John Wiley & Sons Inc., New York 1991).

The reaction according to the invention can be carried out at temperatures of 0–50° C., preferably 0° C. to room temperature. The reaction times are from 10 minutes to 24 hours, preferably 20 minutes to 12 hours.

The base is added either in solid form, preferably in fine-powder form, or as 10–70%, preferably 30–50% aqueous solution. NaOH and KOH are used as preferred bases.

As organic, water-immiscible solvents, for example, toluene, benzene, $CF_3$-benzene, hexane, cyclohexane, diethyl ether, tetrahydrofuran, dichloromethane, MTB or their mixtures can be used in the alkylating process according to the invention.

As phase-transfer catalysts, the quaternary ammonium salts or phosphonium salts or else crown ethers, such as, e.g., [15]-crown-5 or [18]-crown-6, that are known for this purpose are used in the process according to the invention. Quaternary ammonium salts with four identical or different hydrocarbon groups at the cation, selected from methyl, ethyl, propyl, isopropyl, butyl or isobutyl, are preferably suitable. The hydrocarbon groups at the cation must be large enough to ensure good solubility of the alkylating reagent in the organic solvent. According to the invention, N(butyl)$_4^+$—Cl$^-$, N(butyl)$_4^+$—HSO$_4^-$, but also N(methyl)$_4^+$—Cl$^-$ are especially preferably used.

It has been shown that the metal complexes according to the invention are especially suitable for NMR diagnosis and x-ray diagnosis, but also for radiodiagnosis and radiotherapy. The subject of the invention is therefore also the use of the perfluoroalkyl-containing metal complexes according to the invention with sugar radicals for the production of contrast media for use in NMR diagnosis and x-ray diagnosis, especially for lymphography, for tumor diagnosis, and for infarction imaging and necrosis imaging, as well as in radiodiagnosis and radiotherapy. The compounds according to the invention are extremely well suited for use in interstitial lymphography and especially in intravenous lymphography. In addition, they can also be used for visualization of the vascular space (blood-pool agents).

Subjects of the invention are also pharmaceutical agents that contain at least one physiologically compatible compound according to the invention, optionally with the additives that are commonly used in galenicals.

The compounds of this invention are distinguished by a very good systemic compatibility and a high lymph node concentration in three successive lymph node stations (which is important especially for i.v. lymphography). They are thus especially well suited for use in MRT lymphography.

The compounds according to the invention are also extremely well suited for detecting and localizing vascular diseases, since they are dispersed exclusively in the latter in the administration in the intravascular space. The compounds according to the invention make it possible, with the help of nuclear spin tomography, to distinguish between tissue that is well supplied with blood and tissue that is poorly supplied with blood and thus to diagnose an ischemia. Because of its anemia, infarcted tissue can also be distinguished from surrounding healthy or ischemic tissue, when the contrast media according to the invention are used. This is of special importance if the point is, e.g., to distinguish a myocardial infarction from an ischemia.

Compared to the macromolecular compounds previously used as blood-pool agents, such as, for example, Gd-DTPA-polylysine, the compounds according to the invention also show a higher $T^1$-relaxivity and thus are distinguished by an increase of signal intensity in NMR imaging. Since in addition they have an extended retention in the blood space, they can also be administered in relatively small doses (of, e.g., $\leq 50$ μmol of Gd/l of body weight). The compounds according to the invention are primarily quickly and as completely as possible eliminated from the body, however.

It was also shown that the compounds according to the invention accumulate in areas with elevated vascular permeability, such as, e.g., in tumors; they make it possible to make statements on the perfusion of tissues, provide the possibility of determining the blood volumes in tissues, to selectively shorten the relaxation times or densities of the blood and to graphically visualize the permeability of blood vessels. Such physiological data cannot be obtained by the use of extracellular contrast media, such as, e.g., Gd-DTPA (Magnevist$^{(R)}$. From these considerations also arise their uses in modern imaging processes nuclear spin tomography and computer tomography: specific diagnosis of malignant tumors, early therapy control in cytostatic, antiphlogistic or vasodilatative therapy, early detection of underperfused areas (e.g., in the myocardium), angiography in vascular diseases, and detection and diagnosis of sterile or infectious inflammations.

The production of the pharmaceutical agents according to the invention is carried out in a way that is known in the art by the complex compounds according to the invention— optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the Ca-complexes that correspond to the metal complexes according to the invention) or —if necessary—electrolytes such as, for example, sodium chloride or—if necessary—antioxidants, such as, for example, ascorbic acid.

If suspensions or solutions of the agents according to the invention in water or physiological salt solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween$^{(R)}$, Myrj$^{(R)}$] and/or flavoring substance(s) for taste correction [for example, ethereal oils]

Basically, it is also possible to produce the pharmaceutical agents according to the invention without isolating the complexes. In any case, special care must be used to carry out the chelation so that the complexes according to the invention are practically free of non-complexed metal ions that have a toxic effect.

This can be ensured, for example, with the aid of color indicators, such as xylenol orange, by control titrations during the production process. The invention therefore also relates to a process for the production of the complex compounds and their salts. As a final precaution, there remains purification of the isolated complex.

In the in-vivo administration of the agents according to the invention, the latter can be administered together with a suitable vehicle, such as, for example, serum or physiological common salt solution and together with another protein, such as, for example, human serum albumin (HSA).

The agents according to the invention are usually administered parenterally, preferably i.v. They can also be administered intravascularly or interstitially/intracutaneously depending on whether bodily vessels or tissue are to be studied.

The pharmaceutical agents according to the invention preferably contain 0.1 μmol–2 mol/l of the complex and are generally dosed in amounts of 0.0001–5 mmol/kg.

The agents according to the invention meet the many requirements for suitability as contrast media for nuclear spin tomography. After oral or parenteral administration, they are thus extremely well suited for enhancing the informational value of the image that is obtained with the aid of a nuclear spin tomograph by increasing the signal intensity. They also show the high effectiveness that is necessary to load the body with the smallest possible amount of foreign substances and the good compatibility that is necessary to maintain the non-invasive character of the studies.

The good water solubility and low osmolality of the agents according to the invention make it possible to produce highly concentrated solutions, so as to keep the volume burden of the circulatory system within reasonable limits and to offset the dilution by bodily fluids. In addition, the agents according to the invention show not only high stability in vitro, but also surprisingly high stability in vivo, so that a release or an exchange of the ions—which are inherently toxic—and which are bonded to the complexes can take place only extremely slowly within the time in which the new contrast media are completely excreted again.

In general, the agents according to the invention for use as NMR diagnostic agents are dosed in amounts of 0.0001–5 mmol/kg, preferably 0.005–0.5 mmol/kg.

The complex compounds according to the invention also can advantageously be used as susceptibility reagents and as shift reagents for in-vivo-NMR spectroscopy.

Based on their advantageous radioactive properties, and the good stability of the complex compounds contained therein, the agents according to the invention are also suitable as radiodiagnostic agents. Details of such a use and dosage are described in, e.g., "Radiotracers for Medical Applications," CRC-Press, Boca Raton, Fla.

The compounds and agents according to the invention can also be used in positron-emission tomography, which uses positron-emitting isotopes, such as, e.g., $^{43}$SC, $^{44}$SC, $^{52}$Fe, $^{55}$CO, $^{68}$Ga and $^{86}$Y (Heiss, W. D.; Phelps, M. E.; Positron Emission Tomography of Brain, Springer Verlag Berlin, Heidelberg, N.Y. 1983).

The compounds according to the invention are also suitable, surprisingly enough, for differentiating malignant and benign tumors in areas without blood-brain barriers.

Dynamic magnetic resonance imaging of breast neoplasms using a blood-pool agent helps to better differentiate between benign and malignant lesions because it demonstrates the enlarged interstitial space and increased capillary permeability in carcinomas.

MRI following intravenous administration of the compounds of the invention can be used to quantitate changes in capillary integrity induced by hoperoxia, including acute capillary leakiness and return to normal endothelial integrity with recovery from hyperoxic injury.

Histologic findings confirmed regional hyperpermeability.

The technique is generally applicable to the study of abnormal capillary permeability.

They are also distinguished in that they are completely eliminated from the body and thus are well-tolerated.

Since the substances according to the invention accumulate in malignant tumors (no diffusion in healthy tissue, but high permeability of tumor vessels), they can also support the radiation therapy of malignant tumors. The latter is distinguished from the corresponding diagnosis only by the amount and type of the isotope used. The purpose in this case is the destruction of tumor cells with high-energy shortwave radiation with as small a range of action as possible. For this purpose, interactions of the metals (such as, e.g., iron or gadolinium) that are contained in the complexes are used with ionizing radiation (e.g., x-rays) or with neutron rays. By this effect, the local radiation dose at the site where the metal complex is located (e.g., in tumors) is significantly increased. To produce the same radiation dose in malignant tissue, the radiation exposure for healthy tissue can be considerably reduced when using such metal complexes and thus side-effects imposing a burden for the patients are avoided. The metal-complex-conjugates according to the invention are therefore also suitable as radiosensitizing substances in radiation therapy of malignant tumors (e.g., use of Mossbauer effects or in neutron capture therapy). Suitable β-emitting ions are, for example, $^{46}$SC, $^{47}$Sc, $^{48}$Sc, $^{72}$Ga, $^{73}$Ga and $^{90}$Y. Suitably short half-lives that have α-emitting ions are, for example, $^{211}$Bi, $^{212}$Bi, $^{213}$Bi and $^{214}$Bi, whereby $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy proposed by R. L. Mills et al. (Nature Vol. 336, (1988), p. 787), the central ion must be derived from a Mossbauer isotope, such as, for example, $^{57}$Fe or $^{151}$Eu.

In the in-vivo administration of the agents according to the invention, the latter can be administered together with a suitable vehicle, such as, for example, serum, or physiological common salt solution and together with another protein, such as, for example, human serum albumin. In this case, the dosage depends on the type of cellular disorder, the metal ion that is used and the type of imaging method.

The agents according to the invention are usually administered parenterally, preferably i.v. They can also—as already discussed—be administered intravascularly or interstitially/intracutaneously depending on whether bodily vessels or tissue are to be studied.

The agents according to the invention are extremely well suited as x-ray contrast media, whereby it is especially to be emphasized that no displays of the anaphylaxis-like reactions known from the iodine-containing contrast media can be detected with them in biochemical-pharmacological studies. Because of the advantageous absorption properties in the areas of higher tube voltages, they are especially valuable for digital subtraction techniques.

In general, the agents according to the invention for use as x-ray contrast media analogously to the meglumine-diatrizoate example are dosed in amounts of 0.1–5 mmol/kg, preferably 0.25–1 mmol/kg.

In particular, higher blood concentrations are achieved with the compounds according to the invention than with extracellular contrast media. They are dispersed after i.v. administration only into the intravascular space and thus have a decisive advantage compared to the extracellular contrast media.

EXAMPLE 1 a) 2-N-Trifluoroacetyl-6-N-benzyloxycarbonyl-L-lysine 100.0 g (356.7 mmol) of 6-N-benzyloxycarbonyl-L-lysine is dissolved in a mixture that consists of 1000 ml of trifluoroacetic acid ethyl ester and 500 ml of ethanol, and it is stirred for 24 hours at room temperature. It is evaporated to the dry state, and the residue is crystallized from diisopropyl ether.

Yield: 128.9 g (96% of theory) of a colorless, crystalline powder.
Melting point: 98.5° C.
Elementary analysis:

| Cld: | C 51.07 | H 5.09 | N 7.44 | F 15.14 |
|------|---------|--------|--------|---------|
| Fnd: | C 51.25 | H 5.18 | N 7.58 | F 15.03 | b) 2-N-Trifluoroacetyl-6-N-benzyloxycarbonyl-L-lysine[1-(4-perfluorooctylsulfonyl)piperazine]-amide 164.2 g (0.664 mmol) of EEDQ (2-ethoxy-1,2-dihydroquinoline-1-carboxylic acid ethyl ester) is added at 0° C. to 125.0 g (332.0 mmol) of the title compound of Example 1a) and 188.7 g (332.0 mmol) of 1-perfluorooctylsulfonylpiperazine (produced according to DE 19603033) in 750 ml of tetrahydrofuran, and it is stirred overnight at room temperature. It is evaporated to the dry state in a vacuum and chromatographed on silica gel (mobile solvent: dichloromethane/methanol=20:1).

Yield: 286.0 g (93% of theory) of a colorless solid.
Melting point: 92° C.
Elementary analysis:

| Cld: | C 36.30 | H 2.83 | N 6.05 | F 41.01 | S 3.46 |
|------|---------|--------|--------|---------|--------|
| Fnd: | C 36.18 | H 2.94 | N 5.98 | F 40.87 | S 3.40 | c) 6-N-Benzyloxycarbonyl-L-lysine-[1-(4-perfluorooctylsulfonyl)-piperazine]-amide Ammonia gas is introduced at 0° C. for one hour into a solution that consists of 280.0 g (302.2 mmol) of the title compound of Example 1b) in 2000 ml of ethanol. It is then stirred for four hours at 0° C. It is evaporated to the dry state, and the residue is absorptively precipitated from water. The solid is filtered off and dried in a vacuum (50° C.)

Yield: 243.5 g (97% of theory) of an amorphous solid.
Elementary analysis:

| | | | | | |
|---|---|---|---|---|---|
| Cld: | C 37.60 | H 3.28 | N 6.75 | F 38.89 | S 3.86 |
| Fnd: | C 37.55 | H 3.33 | N 6.68 | F 38.78 | S 3.81 | d) 6-N-Benzyloxycarbonyl-2-N-[1-O-α-D-carbonylmethyl-(2,3,4,6-tetra-O-benzyl-mannopyranose]-L-lysine-[1-(4-perfluorooctylsulfonyl)-piperazine]-amide 41.27 g (200.0 mmol) of N,N-dicyclohexylcarbodiimide is added at 0° C. to a solution that consists of 100.0 g (120.4 mol) of the title compound of Example 1c), 72.1 g (120.4 mol) of 1-O-α-D-carboxymethyl-2,3,4,6-tetra-O-benzyl-mannopyranose and 13.86 g (120.4 mol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum and chromatographed on silica gel (mobile solvent: dichloromethane/ethanol=20:1).

Yield: 136.1 g (87% of theory) of a viscous oil.
Elementary analysis:

| | | | | | |
|---|---|---|---|---|---|
| Cld: | C 57.32 | H 4.89 | N 4.31 | F 24.86 | S 2.47 |
| Fnd: | C 57.38 | H 5.07 | N 4.22 | F 24.78 | S 2.39 | e) 2-N-[1-O-α-D-Carbonylmethyl-mannopyranose]-L-lysine-1-[(4-perfluorooctylsulfonyl)-piperazine]-amide 130.0 g (100.0 mmol) of the title compound of Example 1d) is dissolved in 2000 ml of ethanol, and 10.0 g of palladium catalyst (10% Pd/C) is added. It is hydrogenated for 12 hours at room temperature. Catalyst is filtered out, and the filtrate is evaporated to the dry state in a vacuum.

Yield: 91.7 g (quantitative) of a colorless solid.
Elementary analysis:

| | | | | | |
|---|---|---|---|---|---|
| Cld: | C 34.07 | H 3.63 | N 6.11 | S 3.50 | F 35.24 |
| Fnd: | C 33.91 | H 3.72 | N 6.04 | S 3.40 | F 35.31 | f) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-mannopyranose]-L-lysine-[1-(4-perfluorooctylsulfonyl)-piperazine]-amide, Gd complex 50.0 g (54.55 mmol) of the title compound of Example 1e), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 75.9 g (91.0% of theory) of a colorless solid.
Water content: 8.6%.
Elementary analysis (relative to anhydrous substance):

| | | | | | | |
|---|---|---|---|---|---|---|
| Cld: | C 35.34 | H 4.09 | N 8.24 | S 2.10 | F 21.12 | Gd 10.28 |
| Fnd: | C 35.28 | H 4.15 | N 8.19 | S 2.15 | F 21.03 | Gd 10.14 |

EXAMPLE 2 a) 6-N-[1,4,7-Tris(carboxylatomethyl]-1,4,7,10-tetraazacyclododecane-10-N-(pentanoyl-3-aza-4-oxo-5-yl)]-2-N-[1-O-α-D-carbonylmethyl-mannopyranose]-L-lysine-[1-(4-perfluorooctylsulfonyl)-piperazine]-amide, Gd complex 50.0 g (54.55 mmol) of the title compound of Example 1e), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mmol) of N,N-dicyclohexylcarbodiimide is added and then stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile.

Yield: 76.0 g (92.0% of theory) of a colorless solid.
Water content: 6.88%.
Elementary analysis (relative to anhydrous substance):

| | | | | | | |
|---|---|---|---|---|---|---|
| Cld: | C 34.90 | H 3.93 | N 8.32 | S 2.12 | F 21.33 | Gd 10.38 |
| Fnd: | C 34.81 | H 4.02 | N 8.27 | S 2.09 | F 21.22 | Gd 10.19 |

EXAMPLE 3 a) 2-[4-3-Oxapropionic acid ethyl ester]-phenylacetic acid methyl ester 233.8 g (1400.0 mmol) of 2-bromoacetic acid ethyl ester is added to 200.0 g (1204.0 mmol) of 4-hydroxyphenylacetic acid methyl ester, 212.0 g (2000.0 mmol) of sodium carbonate in 2000 ml of acetone, and it is refluxed for 5 hours. The solid is filtered off and evaporated to the dry state in a vacuum. The residue is chromatographed on silica gel (mobile solvent: n-hexane/ethyl acetate=15:1).

Yield: 288.5 g (95.0% of theory) of a colorless oil.
Elementary analysis:

| | | |
|---|---|---|
| Cld: | C 61.90 | H 6.39 |
| Fnd: | C 61.75 | H 6.51 | b) 2-[4-3-Oxapropionic acid ethyl ester)]-phenyl-2-bromoacetic acid methyl ester 201.0 g (1130.0 mmol) of N-bromosuccinimide and 100.0 mg of dibenzoyl peroxide are added to 285.0 g (1130.0 mmol) of the title compound of Example 3a), dissolved in 2000 ml of carbon tetrachloride, and it is refluxed for eight hours. It is cooled in an ice bath, the precipitated succinimide is filtered off, and the filtrate is evaporated to the dry state in a vacuum. The residue is purified on silica gel (mobile solvent: n-hexane/acetone=15:1).

Yield: 359.2 g (96.0% of theory) of a colorless, viscous oil.
Elementary analysis:

| Cld: | C 47.28 | H 4.57 | Br 24.16 |
|------|---------|--------|----------|
| Fnd: | C 47.19 | H 4.71 | Br 24.05 | c) 2-[4-(3-Oxapropionic acid ethyl ester)]-phenyl-2-[1-(1,4,7,10-tetraazacyclododecan-1-yl]-ethyl acetate 350.0 g (1057.0 mmol) of the title compound of Example 3b) is added to 603.0 g (3500.0 mmol) of 1,4,7,10-tetraazacyclododecane, in 6000 ml of chloroform, and it is stirred overnight at room temperature. It is extracted 3 times with 3000 ml of water each, the organic phase is dried on magnesium sulfate and evaporated to the dry state in a vacuum. The residue is used without further purification in the next reaction (Example 3d).

Yield: 448.0 (quantitative) of a viscous oil.
Elementary analysis:

| Cld: | C 59.70 | H 8.11 | N 13.26 |
|------|---------|--------|---------|
| Fnd: | C 59.58 | H 8.20 | N 13.18 | d) 2-[4-(3-Oxapropionic acid)]-phenyl-2-[1,4,7-tris(carboxymethyl)-1,4,7,10-tetraazacyclododecan-10-yl]-acetic acid 445.0 g (1053.0 mmol) of the title compound of Example 3c) and 496.0 g (5270.0 mmol) of chloroacetic acid are dissolved in 4000 ml of water. It is set at a pH of 10 with 30% aqueous sodium hydroxide solution, and it is stirred for 8 hours at 70° C. Then, the pH of the reaction solution is set at 13 by mixing with 30% aqueous sodium hydroxide solution, and it is refluxed for 30 minutes. The solution is cooled in an ice bath and set at a pH of 1 by adding concentrated hydrochloric acid. It is evaporated to the dry state in a vacuum. The residue is taken up in 4000 ml of methanol, and it is absorptively precipitated for one hour at room temperature. Precipitated common salt is filtered out, the filtrate is evaporated to the dry state, and the residue is purified on RP-18 C (mobile solvent: gradient that consists of water/ethanol/acetonitrile).

Yield: 403.0 g (69.0% of theory) of a colorless solid.
Water content: 10.2%.
Elementary analysis (relative to anhydrous substance):

| Cld: | C 51.98 | H 6.18 | N 10.10 |
|------|---------|--------|---------|
| Fnd: | C 51.80 | H 6.31 | N 10.01 | e) 2-[4-(3-Oxapropionic acid)]-phenyl-2-[1,4,7-tris(carboxylatomethyl)-1,4,7,10-tetraazacyclododecan-10-yl]-acetic acid, Gd complex 130.73 g (360.65 mmol) of gadolinium oxide is added to 400 g (721.3 mmol) of the title compound of Example 3d) in 2000 ml of water, and it is stirred for 5 hours at 80° C. The solution is filtered, and the filtrate is freeze-dried.

Yield: 511 g (quantitative) of an amorphous solid.
Water content: 11.0%.
Elementary analysis (relative to anhydrous substance):

| Cld: | C 40.67 | H 4.41 | N 7.98 | Gd 22.19 |
|------|---------|--------|--------|----------|
| Fnd: | C 40.51 | H 4.52 | N 8.03 | Gd 22.05 | f) 6-N-[2-[4-(3-Oxapropionyl)-phenyl]-2-[1,4,7-tris(carboxylatomethyl)-1,4,7,10-tetraazacyclododecan-10-yl]-acetic acid)]-2-N-(1-O-α-D-carbonylmethyl-mannopyranose)-L-lysine-[1-(4-perfluorooctylsulfonyl)-piperazine]-amide, Gd complex, sodium salt 50.0 g (54.55 mmol) of the title compound of Example 1e), 6.28 g (54.55 mmol) of N-hydroxysuccinimide, 4.62 g (109.0 mmol) of lithium chloride and 38.66 g (54.55 mol) of the title compound of Example 3e) are dissolved in 400 ml of dimethyl sulfoxide while being heated slightly. At 10° C., 16.88 g (81.8 mmol) of N,N-dicyclohexylcarbodiimide is added and then stirred overnight at room temperature. The solution is poured into 3000 ml of acetone and stirred for 10 minutes. The precipitated solid is filtered off and then purified-by chromatography (RP-18 mobile solvent: gradient that consists of water/ethanol/acetonitrile).

The product that is obtained is dissolved in a little water, and the pH of the solution is set at 7.4 with aqueous sodium hydroxide solution. Then, the product solution is freeze-dried.

Yield: 79.1 g (89% of theory) of a colorless solid.
Water content: 10.3%.
Elementary analysis (relative to anhydrous substance):

| Cld: | C 36.86 | H 3.77 | N 6.88 | S 1.97 | F 19.82 | Gd 9.65 |
|------|---------|--------|--------|--------|---------|---------|
| Fnd: | C 36.75 | H 3.84 | N 6.80 | S 2.03 | F 19.75 | Gd 9.57 |

EXAMPLE 4 a) 6-N-[1,4,7-Tris(t butyloxycarbonylmethyl)-1,4,7,10-tetraazacyclododecane-10-carbonylmethyl]-2-N-(1-O-α-D-carbonylmethyl-mannopyranose)-L-lysine-[1-(4-perfluorooctylsulfonyl)-piperazine]-amide 15.0 g (26.19 mmol) of 1,4,7-tris(t-butyloxycarbonylmethyl)-10-carboxymethyl-1,4,7,10-tetraazacyclododecane (produced according to: WO91/05762), 24.0 g (26.19 mmol) of the title compound of Example 1e) and 3.01 g (26.19 mmol) of N-hydroxysuccinimide are dissolved in 150 ml of dimethylformamide, and 8.25 g (40.0 mmol) of N,N-dicyclohexylcarbodiimide is added at 0° C. It is stirred overnight at room temperature. The precipitated urea is filtered off, and the filtrate is evaporated to the dry state in a vacuum. The residue is chromatographed on silica gel (mobile solvent: dichloromethane/methanol=20:1).

Yield: 35.45 g (92.0% of theory) of a colorless solid.
Elementary analysis:

| Cld: | C 44.08 | H 5.69 | N 7.62 | F 21.95 | S 2.18 |
|---|---|---|---|---|---|
| Fnd: | C 44.01 | H 5.81 | N 7.53 | F 21.87 | S 2.03 | b) 6-N-[1,4,7-Tris(carboxylatomethyl]-1,4,7,10-tetraazacyclododecane-10-carbonylmethyl-]-2-N-[1-O-α-D-carbonylmethyl-mannopyranose]-L-lysine-[1-(4-perfluorooctylsulfonyl)-piperazine]-amide, Gd complex 30.0 g (20.39 mmol) of the title compound of Example 4a) is dissolved in 50 ml of chloroform, and 300 ml of trifluoroacetic acid is added. It is stirred for 10 minutes at room temperature. It is evaporated to the dry state in a vacuum, and the residue is dissolved in 300 ml of water. 3.69 g (10.19 mmol) of gadolinium oxide is added, and it is stirred for 5 hours at 80° C. The solution is evaporated to the dry state in a vacuum and purified on silica gel (RP-18; mobile solvent: gradient that consists of water/ethanol/acetonitrile).

Yield: 11.0 g (37.0% of theory) of a colorless and amorphous solid.
Water content: 11.3%.
Elementary analysis (relative to anhydrous substance):

| Cld: | C 34.62 | H 3.87 | N 7.59 | F 22.16 | S 2.20 | Gd 10.97 |
|---|---|---|---|---|---|---|
| Fnd: | C 34.57 | H 3.95 | N 7.60 | F 22.05 | S 2.13 | Gd 10.90 |

EXAMPLE 5 a) 6-N-[3,6,9-Tris(carboxymethyl)-3,6,9-triazaundecanedioic acid-1-carboxy-11-oyl]-2-N-[1-O-α-D-carbonylmethyl-mannopyranose]-L-lysine-[1-(4-perfluorooctylsulfonyl)-piperazine]-amide 12.10 g (30.0 mmol) of 3-N-(2,6-dioxomorpholinoethyl)-6-N-(ethoxycarbonylmethyl)-3,6-diazaoctanedioic acid is added to 24.0 g (26.19 mmol) of the title compound of Example 1e), dissolved in 100 ml of dimethylformamide/30 ml of pyridine, and it is stirred for 5 hours at 5° C. It is evaporated to the dry state in a vacuum. The residue is dissolved in 200 ml of water, and the pH of the resulting solution is set at 13 by adding 20% aqueous sodium hydroxide solution. It is stirred for 8 hours at 22° C. and a pH of 13. The solution is brought to a pH of 7.2 by adding concentrated hydrochloric acid, and then it is evaporated to the dry state in a vacuum. The residue is chromatographed on silica gel RP-18 (mobile solvent: gradient that consists of water/ethanol/acetonitrile).

Yield: 17.26 g (51.0% of theory) of a colorless solid.
Water content: 9.3%.
Elementary analysis (relative to anhydrous substance):

| Cld: | C 37.19 | H 4.21 | N 7.59 | F 25.00 | S 2.48 |
|---|---|---|---|---|---|
| Fnd: | C 37.10 | H 4.30 | N 7.48 | F 25.07 | S 2.42 | b) 6-N-[3,6,9-Tris(carboxylatomethyl)-3,6,9-triazaundecanedioic acid-1-carboxy-11-oyl]-2-N-[1-O-α-D-carbonylmethyl-mannopyranose]-L-lysine-[1-(4-perfluorooctylsulfonyl)-piperazine]-amide, Gd complex, sodium salt 1.40 g (3.87 mmol) of gadolinium oxide is added to 10.0 g (7.74 mmol) of the title compound of Example 5a) in 100 ml of water, and it is stirred for 2 hours at 70° C. The solution is filtered. The filtrate is set at a pH of 7.4 with 2N sodium hydroxide solution, and it is freeze-dried.

Yield: 11.36 g (quantitative) of an amorphous solid.
Water content: 10.5%.
Elementary analysis (relative to anhydrous substance):

| Cld: | C 32.72 | H 3.43 | N 6.68 | S 2.18 | Gd 10.71 | Na 1.57 | F 22.00 |
|---|---|---|---|---|---|---|---|
| Fnd: | C 32.65 | H 3.51 | N 6.71 | S 2.08 | Gd 10.61 | Na 1.68 | F 21.87 |

EXAMPLE 6 a) 6-N-Benzyloxycarbonyl-2-N-[1,4,7-tris(carboxylatomethyl)-1,4,7,10-tetraazacyclododecane]-10-(pentanoyl-3aza 4-oxo-5-methyl-5yl)]-L-lysine-[1-(4-perfluorooctylsulfonyl)-piperazine]-amide, Gd complex 50.0 g (60.20 mmol) of the title compound of Example 1c), 6.93 g (60.20 mmol) of N-hydroxysuccinimide, 5.09 g (120.0 mmol) of lithium chloride and 37.91 g (60.20 mmol) of 1,4,7-tris[carboxylatomethyl]-1,4,7,10-tetraazacyclododecane-10-(pentanoyl-3-aza-4-oxo-5-methyl-5-yl), Gd complex, are dissolved in 400 ml of dimethyl sulfoxide while being heated slightly. At 10° C., 20.63 g (100.0 mmol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography (silica gel RP-18; mobile solvent: gradient that consists of water/ethanol/acetonitrile).

Yield: 75.53 g (87.0% of theory) of a colorless solid.
Water content: 10.1%.
Elementary analysis (relative to anhydrous substance):

| Cld: | C 37.48 | H 3.84 | N 8.74 | S 2.22 | F 22.39 | Gd 10.90 |
|---|---|---|---|---|---|---|
| Fnd: | C 37.39 | H 4.02 | N 8.70 | S 2.16 | F 22.29 | Gd 10.75 | b) 2-N-1,4,7-Tris(carboxylatomethyl]-1,4,7,10-tetraazacyclododecane-Gd-complex, 10-(pentanoyl-3-aza-4-oxo-5-methyl-5-yl)-L-lysine-[1-(4-perfluorooctylsulfonyl)-piperazine]-amide 70.0 g (48.53 mmol) of the title compound of Example 1d) is dissolved in 500 ml of water/100 ml of ethanol, mixed with 5.0 g of palladium catalyst (10% Pd/C) and hydrogenated at room temperature under a hydrogen atmosphere (1 atm) until no more hydrogen absorption can be observed. Then, catalyst is suctioned out, it is thoroughly rewashed with ethanol (twice with 75 ml each) and evaporated to the dry state in a vacuum. The title compound is obtained as a strongly viscous and colorless oil.

Yield: 63.5 g (quantitative).
Water content: 9.8%.
Elementary analysis (relative to anhydrous substance):

| | | | | | | |
|---|---|---|---|---|---|---|
| Cld: | C 37.48 | H 3.84 | N 8.74 | S 2.22 | F 22.39 | Gd 10.90 |
| Fnd: | C 37.39 | H 4.03 | N 8.65 | S 2.20 | F 22.31 | Gd 10.78 | c) 6-N-(1-O-α-D-Carbonylmethyl-2,3,4,6-tetra-O-benzyl-mannopyranose)-2-N-[1,4,7-tris(carboxylatomethyl)-1,4,7,10-tetraazacyclododecane, Gd-complex-10-(pentanoyl-3-aza-4oxo-5-methyl-5yl)]-L-lysine-[1-(4-perfluorooctylsulfonyl)-piperazine]-amide 50.0 g (38.22 mmol) of the title compound of Example 6b), 4.40 g (38.22 mmol) of N-hydroxysuccinimide, 3.39 g (80.0 mmol) of lithium chloride and 22.88 g (38.22 mmol) of 1-O-α-D-carboxymethyl-2,3,4,6-tetra-O-benzyl-mannopyranose are dissolved in 400 ml of dimethyl sulfoxide while being heated slightly (30 to 40° C.). At 10° C., 10.32 g (50.0 mmol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 64.25 g (89.0% of theory) of a colorless solid.
Water content: 10.9%.
Elementary analysis (relative to anhydrous substance):

| | | | | | | |
|---|---|---|---|---|---|---|
| Cld: | C 46.42 | H 4.54 | N 6.67 | S 1.70 | F 17.10 | Gd 8.33 |
| Fnd: | C 46.36 | H 4.71 | N 6.60 | S 1.61 | F 17.19 | Gd 8.21 | d) 6-N-(1-O-α-D-Carbonylmethyl-2,3,4,6-tetra-O-benzyl-mannopyranose)-2-N-[1,4,7-tris(carboxylatomethyl)-1,4,8,10-tetraazacyclododecane, Gd-complex-10-(pentanoyl-3-aza-4oxo-5-methyl-5yl)]-L-lysine-[1-(4-perfluorooctylsulfonyl)-piperazine]-amide 60.0 g (31.77 mmol) of the title compound of Example 6c) is dissolved in 500 ml of ethanol and mixed with 6.0 g of palladium catalyst (10% Pd/C). It is hydrogenated at room temperature under a hydrogen atmosphere (1 atm) until no more hydrogen absorption can be observed. Then, catalyst is suctioned out, it is thoroughly rewashed with ethanol (twice with 150 ml each) and evaporated to the dry state in a vacuum.

Yield: 48.55 g (quantitative) of a colorless solid.
Water content: 3.9%.
Elementary analysis (relative to anhydrous substance):

| | | | | | | |
|---|---|---|---|---|---|---|
| Cld: | C 35.37 | H 4.02 | N 8.25 | S 2.10 | F 21.13 | Gd 10.29 |
| Fnd: | C 35.28 | H 4.13 | N 8.17 | S 2.03 | F 21.05 | Gd 10.20 |

EXAMPLE 7 a) 1,7-Bis-(benzyloxycarbonyl)-4-[2-(N-ethyl-N-perfluorooctylsulfonyl]-amino]-acetyl]-1,4,7,10-tetraazacyclododecane)

49.46 g (200.0 mmol) of EEDQ (2-ethoxy-1,2-dihydroquinoline-1-carboxylic acid ethyl ester) is added at 0° C. to 50.0 g (113.5 mmol) of 1,7-bis(benzyloxycarbonyl)-1,4,7,10-tetraazacyclododecane and 66.42 g (113.5 mmol) of 2-(N-ethyl-N-perfluorooctylsulfonyl)-aminoacetic acid (produced according to DE 196 03 033) in-300 ml of tetrahydrofuran, and it is stirred overnight at room temperature. It is evaporated to the dry state in a vacuum and chromatographed on silica gel (mobile solvent: dichloromethane/methanol=20:1).

Yield: 65.2 g (57% of theory) of a colorless solid.
Elementary analysis:

| | | | | | |
|---|---|---|---|---|---|
| Cld: | C 42.91 | H 3.80 | N 6.95 | F 32.05 | S 3.18 |
| Fnd: | C 42.85 | H 3.90 | N 6.87 | F 31.98 | S 3.15 | b) 1,7-Bis-(benzyloxy)-4-[2-(N-ethyl-N-perfluorooctylsulfonyl)-amino]-acetyl-10-[1-O-α-D-carbonylmethyl-2,3,4,6-tetra-O-benzyl-mannopyranose]-1,4,7,10-tetraazacyclododecane 24.73 g (100 mmol) of EEDQ (2-ethoxy-1,2-dihydroquinoline-1-carboxylic acid ethyl ester) is added at 0° C. to 60.0 g (59.53 mmol) of the title compound of Example 7a) and 35.64 g (59.53 mmol) of 1-O-α-D-carboxymethyl-2,3,4,6-tetra-O-benzyl-mannopyranose, produced according to DE 19728954, in 300 ml of tetrahydrofuran, and it is stirred overnight at room temperature. It is evaporated to the dry state in a vacuum and chromatographed on silica gel (mobile solvent: dichloromethane/methanol=20:1).

Yield: 76.6 g (81.0% of theory) of a colorless solid.
Elementary analysis:

| | | | | | |
|---|---|---|---|---|---|
| Cld: | C 54.44 | H 4.70 | N 4.41 | F 20.33 | S 2.02 |
| Fnd: | C 54.37 | H 4.81 | N 4.35 | F 20.27 | S 1.96 | c) 1-[2-(N-Ethyl-N-perfluorooctylsulfonyl)-amino]-acetyl-7-(1-O-α-D-carbonylmethyl-mannopyranose)-1,4,7,10-tetraazacyclododecane 70 g (44.07 mmol) of the title compound of Example 7b is dissolved in 800 ml of ethanol, and 8 g of palladium catalyst (10% Pd/C) is added. It is hydrogenated at room temperature. Catalyst is filtered out, and the filtrate is evaporated to the dry state in a vacuum.

Yield: 42.3 g (quantitative) of a colorless solid.
Elementary analysis:

| | | | | | |
|---|---|---|---|---|---|
| Cld: | C 35.04 | H 3.99 | N 7.30 | F 33.65 | S 3.34 |
| Fnd: | C 35.15 | H 4.13 | N 7.13 | F 33.48 | S 3.26 | d) 1,7-Bis-[1,4,7-tris(carboxylatomethyl)-1,4,7,10-tetraazacyclododecane-Gd-complex-10-(pentanoyl-3-aza-4-oxo-5-methyl-5yl)-4-[2-(N-ethyl-N-perfluorooctylsulfonyl)-amino]-acetyl-10-(1-O-α-D-carbonylmethyl-mannopyranose)-1,4,7,10-tetraazacyclododecane 20 g (20.84 mmol) of the title compound of Example 7c, 5.09 g (120 mmol) of lithium chloride and 37.78 g (60 mmol) of 1,4,7-tris(carboxylatomethyl)-10-pentanoyl-3-aza-4-oxo-5-methyl-5yl)-1,4,7,10-tetraazacyclododecane, Gd complex, are dissolved in 400 ml of dimethyl sulfoxide while being heated slightly. At 10° C., 29.67 g (120 mmol) of EEDQ is added, and then it is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 13.2 g (29.0% of theory) of a colorless solid.
Water content: 11.8%.
Elementary analysis (relative to anhydrous substance):

| | | | | | |
|---|---|---|---|---|---|
| Cld: | C 36.31 | H 4.34 | N 9.62 | S 1.47 | F 14.79 Gd 14.41 |
| Fnd: | C 36.24 | H 4.27 | N 9.58 | S 1.51 | F 14.85 Gd 14.25 |

EXAMPLE 8 a) 1,7-Bis(benzyloxycarbonyl)-4-[2-(N-ethyl-N-perfluorooctylsulfonyl)-amino]-acetyl-10-[pentanoyl-3-aza-4-oxo-5-methyl-5yl-[1,4,7-tris(carboxylatomethyl)-Gd-complex, 1,4,7,10-tetraazacyclododecan-10-yl]-1,4,7,10-tetraazacyclododecane 50.0 g (49.61 mmol) of the title compound of Example 7a), 5.71 g (49.61 mmol) of N-hydroxysuccinimide, 4.24 g (100 mmol) of lithium chloride and 31.24 g (49.61 mmol) of 1,4,7-tris(carboxylatomethyl)-10(pentanoyl-3-aza-4-oxo-5-methyl-5-yl)-1,4,7,10-tetraazacyclododecane, Gd complex, are dissolved in 350 ml of dimethyl sulfoxide while being heated slightly. At 10° C., 15.47 g (75 mmol) of N,N-dicyclohexylcarbodiimide is added, and it then is stirred overnight at room temperature. The solution is poured into 2000 ml of acetone and stirred for 10 minutes. The precipitated solid is filtered off and then purified by chromatography (silica gel RP-18, mobile solvent: gradient that consists of water/ethanol/acetonitrile).

Yield: 65.1 g (81.0% of theory) of a colorless solid.
Water content: 7.9%.
Elementary analysis (relative to anhydrous substance):

| | | | | | |
|---|---|---|---|---|---|
| Cld: | C 40.79 | H 4.11 | N 8.65 | S 1.98 | F 19.94 Gd 9.72 |
| Fnd: | C 40.71 | H 4.20 | N 8.58 | S 2.03 | F 19.87 Gd 9.68 | b) 1-[2-(N-Ethyl-N-perfluorooctylsulfonyl)-amino]-acetyl-7{-pentanoyl-3-aza-4-oxo-5-methyl-5yl-[tris(carboxylatomethyl-1,4,7,10-tetraazacyclododecan-10-yl]-Gd-complex}-1,4,7,10 tetraazacyclododecane 60.0 g (37.05 mmol) of the title compound of Example 8a) is dissolved in 600 ml of ethanol, and 6.0 g of palladium catalyst (10% Pd/C) is added. It is hydrogenated at room temperature. Catalyst is filtered out, and the filtrate is evaporated to the dry state in a vacuum.

Yield: 50.06 g (quantitative) of a colorless solid.
Water content: 3.9%
Elementary analysis (relative to anhydrous substance):

| | | | | | |
|---|---|---|---|---|---|
| Cld: | C 34.67 | H 4.03 | N 10.37 | S 2.37 | F 23.90 Gd 11.64 |
| Fnd: | C 34.58 | H 4.15 | N 10.28 | S 2.30 | F 23.84 Gd 11.57 | c) 1-[2-(N-Ethyl-N-perfluorooctylsulfonyl)-amino]-acetyl-4,10-bis[1-O-α-D-carbonylmethyl-2,3,4,6-tetra-O-benzyl-mannopyranose]-7-{pentanoyl-3-aza-4-oxo-5-methyl-5-yl-[1,4,7-tris(carboxylatomethyl)-1,4,7,10-tetraazacyclododecan-10-yl]-Gd complex}-1,4,7,10-tetraazacyclododecane 40.0 g (29.60 mmol) of the title compound of Example 8b), 2.54 g (60.0 mmol) of lithium chloride and 44.9 g (75.0 mmol) of 1-O-α-D-carboxymethyl-2,3,4,6-tetra-O-benzyl-mannopyranose are dissolved in 300 ml of dimethyl sulfoxide while being heated slightly. At 10° C., 24.73 g (100.0 mmol) of EEDQ is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 31.98 g (43.0% of theory) of a colorless solid.
Water content: 3.5%.
Elementary analysis (relative to anhydrous substance):

| | | | | | |
|---|---|---|---|---|---|
| Cld: | C 53.06 | H 5.05 | N 5.57 | S 1.28 | F 12.85 Gd 6.26 |
| Fnd: | C 52.95 | H 5.19 | N 5.48 | S 1.23 | F 12.77 Gd 6.14 | d) 1-[2-(N-Ethyl-N-perfluorooctylsulfonyl)-amino]-acetyl-4,10-bis[1-O-α-D-carbonylmethyl-2,3,4,6-tetra-O-benzyl-mannopyranose]-7-{pentanoyl-3-aza-4-oxo-5-methyl-5-yl-[1,4,7-tris(carboxylatomethyl)-1,4,7,10-tetraazacyclododecan-10-yl]-Gd complex}-1,4,7,10-tetraazacyclododecane 30.0 g (11.94 mmol) of the title compound of Example 8c) is dissolved in 300 ml of ethanol/30 ml of water, and 4.0 g of palladium catalyst (10% Pd/C) is added. It is hydrogenated at room temperature, catalyst is filtered out, and the filtrate is evaporated to the dry state in a vacuum.

Yield: 21.39 g (quantitative) of a colorless solid.
Water content: 3.4%.
Elementary analysis (relative to anhydrous substance):

| | | | | | |
|---|---|---|---|---|---|
| Cld: | C 36.87 | H 4.39 | N 7.82 | S 1.79 | F 18.03 Gd 8.78 |
| Fnd: | C 36.80 | H 4.50 | N 7.85 | S 1.68 | F 17.91 Gd 8.70 |

EXAMPLE 9 a) 6-N-[3,6-Bis(carboxymethyl)-octane-1,8-dicarboxylic acid-1-carboxy-8-oyl]-2-N-(1-O-α-D-carboxymethyl-mannopyranose)-lysine-[1-(4-perfluorooctylsulfonyl)-piperazine]-amide 25.62 g (100.0 mmol) of ethylenediamine-N,N,N',N'-tetraacetic acid dianhydride is added to 27.5 g (30.0 mmol)

of the title compound of Example 1e), dissolved in 300 ml of dimethylformamide/100 ml of pyridine, and it is stirred for 5 hours at 50° C. It is evaporated to the dry state in a vacuum. The residue is dissolved in 300 ml of water, set at a pH of 10 by adding 20% aqueous sodium hydroxide solution, and then the basic product solution is brought to a pH of 3 by adding concentrated hydrochloric acid, and it is evaporated to the dry state in a vacuum. The residue is chromatographed on silica gel RP-18 (mobile solvent: gradient that consists of water/ethanol/acetonitrile).

| Yield: | 18.22 g (51.0% of theory) of a colorless solid. | | | | |
|---|---|---|---|---|---|
| Water content: | 7.9%. | | | | |
| Elementary analysis (relative to anhydrous substance): | | | | | |
| Cld: | C 36.31 | H 3.98 | N 7.06 | F 27.12 | S 2.69 |
| Fnd: | C 36.23 | H 4.07 | N 6.98 | F 27.05 | S 2.62 | b) 6-N-[3,6-Bis(carboxylatomethyl)-octane-1,8-dicarboxylic acid-1-carboxylato-8-oyl-Mn-complex, sodium salt]-2-N-(1-O-α-D-carboxymethyl-mannopyranose)-L-lysine-[1-(4-perfluorooctylsulfonyl)-piperazine]-amide 10 g (8.397 mmol) of the title compound of Example 9a) is dissolved in 200 ml of water. 965 mg (8.397 mmol) of manganese(II) carbonate is added, and it is stirred for 3 hours at 60° C. The solution is set at a pH of 7.4 with 5% aqueous sodium hydroxide solution, filtered, and then freeze-dried.

| Yield: | 10.52 g (99.0% of theory) of a colorless solid. |
|---|---|
| Water content: | 7.8%. |
| Elementary analysis (relative to anhydrous substance): | |
| Cld: | C 34.16 H 3.50 N 6.64 S 2.53 F 25.52 Mn 4.34 Na 1.82 |
| Fnd: | C 34.06 H 3.61 N 6.58 S 2.47 F 25.47 Mn 4.30 Na 1.97 |

EXAMPLE 10 a) 1,2,3,4,6-Penta-O-acetyl-α,β-D-mannopyranose

Analogously to what is described in the literature [M. L. Wolfrom and A. Thompson in Methods in Carbohydrate Chemistry (R. L. Whistler, M. L. Wolfrom and J. N. BeMiller, Eds.), Academic Press, New York, Vol. II, 53, pp. 211–215, (1963)], the reaction of 150 g (832.5 mmol) of α,β-D-mannopyranose with a mixture that consists of 1500 ml of absolute pyridine and 1500 ml of acetic acid anhydride yields, after working-up, 315 g (96.7%) of the above-mentioned title compound as a crude product in the form of a viscous and colorless oil. By $^1$H-NMR spectroscopic study of the thus obtained title compound, it was possible to determine the α to β ratio of both anomers at 4:1. Separation of α,β-anomers of the above-mentioned title compound can be eliminated to perform the subsequent reaction step.

| Elementary analysis: | | |
|---|---|---|
| Cld: | C 49.21 | H 5.68 |
| Fnd: | C 49.12 | H 5.78 | b) 1-O-α-D-(5-Ethoxycarbonyl)-pentyl-2,3,4,6-tetra-O-acetyl-mannopyranose

Analogously to what is described in the literature for the synthesis of aryl glycopyranosides [J. Conchie and G. A. Levvy in Methods in Carbohydrate Chemistry (R. L. Whistler, M. L. Wolfrom and J. N. BeMiller, Eds.), Academic Press, New York, Vol. II, 90, pp. 345–347, (1963)], the reaction of 156.2 g (400 mmol) of the title compound of Example 10a) as an α,β-anomer mixture with 67 ml (400 mmol) of 6-hydroxy-hexanoic acid ethyl ester and 60.8 ml (520 mmol) of tin(IV) chloride results in a total of 600 ml of 1,2-dichloroethane after column-chromatographic purification (eluant: hexane/ethyl acetate 2:1) to form 100.05 g (51% of theory) of the above-mentioned title compound as a colorless and viscous oil. By $^1$H-NMR-spectroscopic study of the thus obtained title compound, it was possible to show that the above-mentioned title compound is only the pure α-anomer.

| Elementary analysis: | | |
|---|---|---|
| Cld: | C 52.94 | H 6.77 |
| Fnd: | C 52.80 | H 6.78 | c) 1-O-α-D-(5-Carboxy)-pentyl-2,3,4,6-tetra-O-benzyl-mannopyranose

A stirred suspension of 141.0 g (289 mmol) of the title compound of Example 1b) in 200 ml of dioxane is mixed at room temperature and with simultaneous vigorous stirring in portions with a total of 238.5 g (4.26 mol) of fine-powder potassium hydroxide powder. To make it easier to stir, the reaction mixture is mixed with another 200 ml of dioxane, and the thus obtained suspension is subsequently heated to boiling heat and mixed drop by drop at this temperature with a total of 372 ml (3.128 mol) of benzyl bromide over a period of two hours. After a reaction time of 4 hours at 110° C. followed by 12 hours at room temperature, the reaction mixture is slowly poured into a total of 2.5 liters of ice water for the purpose of working-up, and the water phase is subsequently completely extracted with diethyl ether. After the thus obtained ether phase is washed and after the subsequent drying of the same on sodium sulfate, salt is suctioned out, and the diethyl ether is drawn off in a vacuum. Excess benzyl bromide is then distilled off from the reaction mixture in an oil pump vacuum quantitatively at an oil bath temperature of 180° C. The thus obtained, resinous-oily residue is purified on silica gel with use of ethyl acetate/hexane (1:10) as an eluant.

| Yield: | 172.2 g (91.0% of theory) of the above-mentioned title compound in the form of a colorless and extremely viscous oil. | |
|---|---|---|
| Elementary analysis: | | |
| Cld: | C 75.68 | H 7.16 |
| Fnd: | C 75.79 | H 7.04 | d) 6-N-Benzyloxycarbonyl-2-N-[1-O-α-D-(5-carbonyl)-pentyl-2,3,4,6-tetra-O-benzyl-mannopyranose]-L-lysine-[1-(4-perfluorooctylsulfonyl)-piperazine]-amide 100.0 g (134.0 mmol) of the carboxylic acid that is produced under Example 10c) and 32.4 g (281.4 mmol) of N-hydroxysuccinimide are dissolved in 500 ml of dimethylformamide and mixed in portions at 0° C. with a total of 58.0 g (281.4 mmol) of N,N'-dicyclohexylcarbodiimide, and it is stirred for 3 more hours at this temperature. A solution, cooled to 0° C., of 111.3 g (134.0 mmol) of the title compound of Example 1c), dissolved in 300 ml of dimethylformamide, is added drop by drop to the thus produced active ester solution, and it is stirred for 2 hours at 0° C. and for 12 hours at room temperature. For working-up, precipitated dicyclohexylurea is filtered out, and the solvent is then evaporated to the dry state. The thus obtained residue is then chromatographed on silica gel (mobile solvent: dichloromethane/ethanol 20:1; chromatography is carried out with use of a solvent gradient with continuous increase of the proportion of ethanol).

Yield: 132.5 g (67.4% of theory) of the title compound in the form of a colorless and strongly viscous oil.
Elementary analysis:

| | | | | | |
|---|---|---|---|---|---|
| Cld: | C 54.02 | H 4.88 | N 3.82 | F 22.01 | S 2.19 |
| Fnd: | C 53.87 | H 4.85 | N 4.02 | F 22.55 | S 2.06 | e) 2-N-[1-O-α-D-(5-Carbonyl)pentyl]-mannopyranose]-L-lysine-[-1-(4-perfluorooctylsulfonyl)-piperazine]-amide 120.0 g (81.77 mmol) of the compound, produced under 10d), is dissolved in 800 ml of ethanol, mixed with 4.5 g of Pearlman's catalyst (Pd 20%, C) and hydrogenated at room temperature under a hydrogen atmosphere (1 atm) until no more hydrogen absorption can be observed (about 8 hours). Catalyst is suctioned out, it is thoroughly rewashed with ethanol (about 200 ml) and evaporated to the dry state in a vacuum. The title compound is obtained as a strongly viscous and colorless oil.

Yield: 78.5 g (98.7% of theory)
Elementary analysis:

| | | | | | |
|---|---|---|---|---|---|
| Cld: | C 37.04 | H 4.25 | N 5.76 | F 33.20 | S 3.30 |
| Fnd: | C 36.96 | H 4.85 | N 5.41 | F 34.13 | S 3.22 | f) 2-N-[1-O-α-D-(5-Carbonyl)pentyl-mannopyranose]-6-N-[1,4,7-tris-(carboxylatomethyl)-10-(-3-aza-4-oxo-5-methyl-5-yl-pentanoyl)-1,4,7,10-tetraazacyclododecane]-L-lysine-[1-(4-perfluorooctylsulfonyl)-piperazine]-amide, Gd complex 99.8 g (158.4 mmol; 2.2 molar equivalents relative to the amine component of Example 10e) that is used of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 6.7 g of anhydrous lithium chloride (158.4 mmol) are dissolved at 40° C. in 800 ml of absolute dimethyl sulfoxide while being stirred. At this temperature, it is subsequently mixed with a total of 18.2 g (158.4 mmol) of N-hydroxysuccinimide and 70.0 g (71.96 mmol) of the title compound of Example 10e), dissolved in 250 ml of absolute dimethyl sulfoxide. After cooling to room temperature, the reaction solution is mixed with 32.7 g (158.4 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off: 3,000 Da), and low-molecular components are removed. The retentate is then freeze-dried.

Yield: 93.0 g (81.6% of theory) as a colorless lyophilizate.
H$_2$O content 9.53%.
(Karl-Fischer):
Elementary analysis (relative to anhydrous substance):

| | | | | | | |
|---|---|---|---|---|---|---|
| Cld: | C 37.15 | H 4.39 | N 7.96 | F 20.38 | S 2.02 | Gd 9.92 |
| Fnd: | C 36.92 | H 4.50 | N 7.68 | F 19.77 | S 1.91 | Gd 10.08 |

EXAMPLE 11 a) 2-N-[1-O-α-D-(5-Carbonyl)pentyl-mannopyranose]-6-N-{2-[4-(3-oxapropionyl)-phenyl]-2-[1,4,7-tris-(carboxylatomethyl)-1,4,7,10-tetraazacyclododecan-10-yl]-acetic acid}-L-lysine-[1-(4-perfluorooctylsulfonyl)-piperazine]-amide, Gd complex, sodium salt A stirred suspension of 5.0 g (9.06 mmol) of the title compound of Example 3e) in 15 ml of absolute dimethyl sulfoxide is mixed at 70° C. with 0.68 g (15.9 mmol) of lithium chloride. After 30 minutes of stirring at 70° C., the now clear reaction solution is mixed in portions with a total of 1.83 g (15.9 mmol) of N-hydroxysuccinimide, and the reaction mixture is kept at this temperature for 1 more hour. After cooling to 0° C., it is mixed with 4.52 g (23.85 mmol) of dicyclohexylcarbodiimide, and the reaction solution is stirred for another hour at 0° C., followed by 12 hours at 22° C. The thus obtained reaction solution of the N-hydroxysuccinimide ester of the title compound of Example 3e) is now mixed drop by drop at 22° C. with a solution of 4.0 g (4.12 mmol) of the title compound of Example 1e) in 15 ml of absolute dimethyl sulfoxide, and it is stirred for another 12 hours at room temperature. For working-up, the reaction solution is added in drops at 22° C. in 900 ml of acetone, whereby the title compound precipitates as a colorless precipitate. The precipitate is suctioned off, dissolved in 200 ml of distilled water, and then the pH of this solution is set at exactly 7.2 with 1 molar sodium hydroxide solution. The thus obtained aqueous product solution is ultrafiltered three times with a YM-3 ultrafiltration membrane (AMICON(R): cut-off: 3,000 Da) for the purpose of desalination and the separation of low-molecular components. The thus obtained retentate is then freeze-dried.

Yield: 6.33 g (92.4% of theory, relative to the amine component that is used) as a colorless lyophilizate with a water content of 7.38%.
Elementary analysis (relative to anhydrous substance):

| | | | | | | |
|---|---|---|---|---|---|---|
| Cld: | C 38.48 | H 4.13 | N 6.65 | F 19.16 | S 1.90 | Gd 9.33 Na 1.36 |
| Fnd: | C 39.52 | H 4.12 | N 6.67 | F 19.70 | S 1.89 | Gd 9.30 Na 1.41 |

EXAMPLE 12 a) 3,5-Bis-benzyloxycarbonylamino-benzoic acid-N-(3-oxa-1H,1H,2H,2H,4H,4H,5H,5H-perfluorotridecyl)-amide 20 g (47.5 mmol) of 3,5-bis-benzyloxycarbonylamino-benzoic acid (synthesis according to the subsequent bibliographic reference: Skulnick, Harvey I.; Johnson, Paul D.; Aristoff, Paul A.; Morris, Jeanette K.; Lovasz, Kristine D.; et al.; J. Med. Chem.; 40; 7; 1997; 1149–1164) and 4.78 g (47.5 mmol) of triethylamine are dissolved in a solvent mixture that consists of 125 ml of dry tetrahydrofuran and 125 ml of dry dioxane. After cooling to −15° C., a solution of 6.56 g (48 mmol) of isobutyl chloroformate in 30 ml of dry tetrahydrofuran is slowly added in drops while being stirred, whereby the internal temperature is to be kept below −10° C. After a reaction time of 15 minutes at −15° C., a solution of 58.6 g (47.5 mmol) of 1-amino-1H,1H,2H,2H, 4H,4H,5H,5H-3-oxa-perfluorotridecane and 4.78 g (47.5 mmol) of triethylamine in 100 ml of dry tetrahydrofuran is added in drops at −20° C. After a reaction time of one hour at −15° C. and two hours at room temperature, the reaction solution is evaporated to the dry state in a vacuum. The remaining residue is taken up in 300 ml of ethyl acetate and washed twice with 200 ml each of saturated sodium bicarbonate solution and once with 300 ml of water. After the organic phase is dried on sodium sulfate, salt is suctioned out, and the ethyl acetate is drawn off in a vacuum. The remaining oily residue is purified on silica gel with use of dichloromethane/hexane/2-propanol (10:5:1) as an eluant.

| Yield: | 36.2 g (82.5% of theory) of the title compound as a colorless oil. | | | |
|---|---|---|---|---|
| | Elementary analysis: | | | |
| Cld: | C 46.82 | H 3.27 | N 4.55 | F 34.97 |
| Fnd: | C 47.21 | H 3.31 | N 4.61 | F 34.48 | b) 3,5-Di-amino-benzoic acid-N-(3-oxa-1H,1H,2H, 2H,4H,4H,5H,5H-perfluorotridecyl)]-amide 30.0 g (32.4 mmol) of the amide that is produced under 12a) is dissolved in 300 ml of ethanol and mixed with 1.2 g of Pearlman's catalyst (Pd 20%, C). It is hydrogenated at room temperature under a hydrogen atmosphere (1 atm) until no more hydrogen absorption can be observed. Catalyst is suctioned out, it is thoroughly rewashed with ethanol (about 300 ml) and evaporated to the dry state in a vacuum. The title compound is obtained as a strongly viscous, yellowish oil.

| Yield: 20.12 g (94.8% of theory) | | | | |
|---|---|---|---|---|
| | Elementary analysis: | | | |
| Cld: | C 36.66 | H 2.77 | N 6.41 | F 49.28 |
| Fnd: | C 36.07 | H 2.87 | N 6.23 | F 49.43 | c) 3-N-[-(1-O-α-D-Carbonylmethyl-2,3,4,6-tetra-O-benzyl-mannopyranose)-5-amino-benzoic acid-N-(3-oxa-1H,1H,2H,2H,4H,4H,5H,5H-perfluorotridecyl)-amide 10.95 g (18.30 mmol) of 1-carboxymethyloxy-2,3,4-tetra-O-benzyl-α-D-mannopyranoside [production as described in Patent DE 197 28 954 C1] is dissolved in 150 ml of dimethylformamide and mixed with a total of 2.09 g (18.3 mmol) of N-hydroxysuccinimide. It is cooled to 0° C., and 3.78 g (18.3 mmol) of dicyclohexylcarbodiimide is added. It is stirred for one hour at 0° C. and then for 4 hours at room temperature. It is cooled to 0° C., and a solution that consists of 24.0 g (36.6 mmol, 2 molar equivalents relative to the carboxylic acid that is used) of the diamino compound, described under Example 12b), dissolved in 350 ml of dimethylformamide, is slowly added in drops within 3 hours. Then, it is stirred for one more hour at 0° C., then overnight at room temperature. It is evaporated to the dry state in a vacuum, and the residue is taken up in 300 ml of ethyl acetate. Precipitated urea is filtered out, and the filtrate is washed twice with 100 ml each of 5 aqueous soda solution. The organic phase is dried on magnesium sulfate and evaporated to the dry state in a vacuum. The residue is chromatographed on silica gel (mobile solvent: n-hexane/isopropanol 13:1). 16.8 g (74.3% of theory, relative to the carboxylic acid that is used) of the title compound is obtained in the form of a colorless oil. By increasing the polarity of the eluant composition to n-hexane/isopropanol 5:1, a total of 10.15 g of unreacted diamino compound 12b) is recovered in the subsequent chromatography fractions, which can be reacted again according to the above-mentioned reaction instructions.

| | Elementary analysis: | | | |
|---|---|---|---|---|
| Cld: | C 54.42 | H 4.40 | N 3.40 | F 26.13 |
| Fnd: | C 54.32 | H 4.49 | N 3.48 | F 25.94 | d) 3-N-[-(1-O-α-D-Carbonylmethyl-mannopyranose)]-5-amino-benzoic acid-N-(3-oxa-1H,1H,2H,2H,4H,4H,5H,5H-perfluorotridecyl)-amide Analogously to what is described for the synthesis of the title compound of Example 12b), the hydrogenolysis of 12.0 g (9.70 mmol) of the title compound of Example 12c), with use of 0.5 g of Pearlman's catalyst (Pd 20%, C) in an ethanol/water (9:1) mixture after working-up yields 8.08 g (96.7% of theory) of the above-mentioned title compound in the form of a yellowish-colored and viscous oil.

| | Elementary analysis: | | | |
|---|---|---|---|---|
| Cld: | C 37.64 | H 3.28 | N 4.88 | F 37.49 |
| Fnd: | C 37.32 | H 3.17 | N 4.97 | F 37.55 | e) 3-N-(1-O-α-D-Carbonylmethyl-mannopyranose)-5-N-{2-[4-(3-oxapropionyl)-phenyl]-2-[1,4,7-tris-(carboxylatomethyl)-1,4,7,10-tetraazacyclododecan-10-yl]-acetic acid}-benzoic acid-N-(3-oxa-1H, 1H, 2H,2H,4H,4H,5H,5H-perfluorotridecyl)-amide, Gd complex, sodium salt 13.6 g (19.2 mmol; 2.2 molar equivalents relative to the amine component that is used of Example 12d) of the Gd complex that is described under Example 3e) and 0.81 g of anhydrous lithium chloride (19.2 mmol) are dissolved at 40° C. in 100 ml of absolute dimethyl sulfoxide while being stirred, and it is mixed at this temperature with a total of 2.2 g (19.2 mmol) of N-hydroxysuccinimide and 7.5 g (8.7 mmol) of the title compound of Example 12d), dissolved in 50 ml of absolute dimethyl sulfoxide.

After cooling to room temperature, the reaction solution is mixed with 3.96 g (19.2 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off 3,000 Da), and low-molecular components are removed. The retentate is then freeze-dried.

| Yield: 11.51 g (84.5% of theory) as a colorless lyophilizate. H₂O content (Karl-Fischer): 6.77%. Elementary analysis (relative to anhydrous substance): | | | | | |
|---|---|---|---|---|---|
| Cld: | C 40.05 | H 3.94 | N 6.29 | F 20.71 | Gd 10.08 Na 1.47 |
| Fnd: | C 39.98 | H 4.00 | N 6.31 | F 20.73 | Gd 10.11 Na 1.42 |

EXAMPLE 13 a) 3,5-Bis-(benzyloxycarbonylamino)-1-{N-[1-(4-perfluorooctylsulfonyl)-piperazine]}-benzamide 10 g (23.75 mmol) of 3,5-bis-benzyloxycarbonylaminobenzoic acid (synthesis according to the subsequent bibliographic reference: Skulnick, Harvey I.; Johnson, Paul D.; Aristoff, Paul A.; Morris, Jeanette K.; Lovasz, Kristine D.; et al.; J. Med. Chem.; 40; 7; 1997; 1149–1164) and 2.39 g (23.75 mmol) of triethylamine are dissolved in a solvent mixture that consists of 60 ml of dry tetrahydrofuran and 70 ml of dry dioxane. After cooling to −15° C., a solution of 3.28 g (24 mmol) of isobutyl chloroformate in 20 ml of dry tetrahydrofuran is slowly added in drops, whereby the internal temperature does not exceed −10° C. After a reaction time of 15 minutes at −15° C., a solution of 23.0 g (23.75 mmol) of perfluorooctylsulfonylpiperazine and 2.39 g (23.75 mmol) of triethylamine in 50 ml of dry tetrahydrofuran is added in drops at −20° C. After a reaction time of one hour at −15° C. and two hours at room temperature, the reaction solution is evaporated to the dry state in a vacuum. The remaining residue is taken up in 200 ml of ethyl acetate and washed twice with 100 ml each of saturated sodium bicarbonate solution and once with 300 ml of water. After the organic phase is dried on sodium sulfate, salt is suctioned out, and the ethyl acetate is drawn off in a vacuum. The remaining oily residue is purified on silica gel with use of dichloromethane/hexane/2-propanol (15:5:1) as an eluant.

| Yield: 18.35 g (79.6% of theory) of the title compound as a colorless oil. Elementary analysis: | | | | | |
|---|---|---|---|---|---|
| Cld: | C 43.31 | H 2.80 | N 5.77 | F 33.27 | S 3.30 |
| Fnd: | C 43.21 | H 2.75 | N 5.61 | F 33.38 | S 3.22 | b) 3,5-Di-amino-1-{N-[1-(4-perfluorooctylsulfonyl)-piperazinel]}-benzamide 9.70 g (10.0 mmol) of the amide that is produced under 13a) is dissolved in 100 ml of ethanol and mixed with 0.4 g of Pearlman's catalyst (Pd 20%, C). It is hydrogenated at room temperature under a hydrogen atmosphere (1 atm) until no more hydrogen absorption can be observed. Catalyst is suctioned out, it is thoroughly rewashed with ethanol (about 150 ml) and evaporated to the dry state in a vacuum. The title compound is obtained as a strongly viscous, yellowish oil.

| Yield: 6.9 g (98.2% of theory). Elementary analysis: | | | | | |
|---|---|---|---|---|---|
| Cld: | C 32.49 | H 2.15 | N 7.98 | F 45.98 | S 4.56 |
| Fnd: | C 32.56 | H 2.17 | N 8.09 | F 45.63 | S 4.61 | c) 5-Amino-3-N-(1-O-α-D-carbonylmethyl-2,3,4,6-tetra-O-benzyl-mannopyranose)-benzoic acid-N-[1-(4-perfluorooctylsulfonyl)-piperazine]-amide 5.48 g (9.15 mmol) of 1-carboxymethyloxy-2,3, 4-tetra-O-benzyl-α-D-mannopyranoside [production as described in Patent DE 197 28 954 C1] is dissolved in 100 ml of dimethylformamide and mixed with a total of 1.04 g (9.15 mmol) of N-hydroxysuccinimide. It is cooled to 0° C., and 1.89 g (91.5 mmol) of dicyclohexylcarbodiimide is added. It is stirred for one hour at 0° C. and then for 4 hours at room temperature. After being cooled to 0° C. again, a solution that consists of 12.85 g (18.30 mmol, 2 molar equivalents relative to the carboxylic acid that is used) of the diamino compound, described under Example 13b) and dissolved in 250 ml of dimethylformamide, is slowly added in drops within 3 hours. Then, it is stirred for one more hour at 0° C., then overnight at room temperature. It is evaporated to the dry state in a vacuum, and the residue is taken up in 100 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 13:1). 8.14 g (69.4% of theory, relative to the carboxylic acid that is used) of the title compound is obtained in the form of a colorless oil. By increasing the polarity of the eluant composition during chromatography to 6:1 (n-hexane/isopropanol), a total of 4.36 g of unreacted diamino compound 13b) is recovered in the chromatography fractions below, which can be reacted again according to above-mentioned reaction instructions.

| Elementary analysis: | | | | | |
|---|---|---|---|---|---|
| Cld: | C 51.49 | H 4.01 | N 4.37 | F 25.17 | S 2.50 |
| Fnd: | C 51.60 | H 4.19 | N 4.28 | F 25.14 | S 2.44 | d) 5-Amino-3-N-(1-O-α-D-carbonylmethyl-mannopyranose)-benzoic acid-N-[1-(4-perfluorooctylsulfonyl)-piperazine]-amide Analogously to what is described for the synthesis of the title compound of Example 13b), the hydrogenolysis of 6.4 g (5.0 mmol) of the title compound of Example 13c) with use of 0.3 g of Pearlman's catalyst (Pd 20%, C) in an ethanol/water (8:1) mixture after working-up yields 4.43 g (96.2% of theory) of the above-mentioned title compound in the form of a yellowish-colored and viscous oil.

| Elementary analysis: | | | | | |
|---|---|---|---|---|---|
| Cld: | C 35.15 | H 2.95 | N 6.07 | F 35.01 | S 3.48 |
| Fnd: | C 35.32 | H 3.02 | N 5.89 | F 35.05 | S 3.58 | e) 3-N-(1-O-α-D-Carbonylmethyl-mannopyranose)-5-N-[1,4,7-tris(carboxylatomethyl)-10-(3-aza-4-oxo-5-methyl-5-yl-pentanoyl)-1,4,7,10-tetraazacyclododecane]-benzoic acid-N-[1-(4-perfluorooctylsulfonyl)-piperazine]-amide, Gd complex 5.54 g (8.8 mmol; 2.2 molar equivalents relative to the amine component of Example 13d) that is used) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g of anhydrous lithium chloride (8.8 mmol) are dissolved at 40° C. in 60 ml of absolute dimethyl sulfoxide while being stirred and mixed at this temperature with a total of 1.01 g (8.8 mmol) of N-hydroxysuccinimide and 3.7 g (4.0 mmol) of the title compound of Example 13d), dissolved in 40 ml of absolute dimethyl sulfoxide. After cooling to room temperature, the reaction solution is mixed with 1.82 g (8.8 mmol) of N,N'-dicyclohexylcarbodiimide, and it is stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON$^{(R)}$ YM-3 ultrafiltration membrane (cut-off 3,000 Da), and low-molecular components are removed. The retentate is then freeze-dried.

Yield: 5.36 g (87.4% of theory) as a colorless lyophilizate.
H$_2$O content (Karl-Fischer): 6.77%.
Elementary analysis (relative to anhydrous substance):

| | | | | | | |
|---|---|---|---|---|---|---|
| Cld: | C 36.01 | H 3.61 | N 8.22 | F 21.05 | Gd 10.25 | S 2.09 |
| Fnd: | C 35.87 | H 3.70 | N 8.22 | F 20.91 | Gd 10.18 | S 2.16 |

EXAMPLE 14 a) 1,4,7-Triazaheptane-1,7-bis-(2-N-trifluoroacetyl-6-N-benzyloxycarbonyl-L-lysine)-diamide 100 g (107.9 mmol) of the carboxylic acid that is produced under Example 1a) and 26.1 g (226.59 mmol) of N-hydroxysuccinimide are dissolved in 500 ml of dimethylformamide and mixed in portions at 0° C. with a total of 46.7 g (226.59 mmol) of N,N'-dicyclohexylcarbodiimide, and it is stirred for 3 more hours at this temperature. A solution, cooled to 0° C., of 5.57 g (53.95 mmol) of diethylenetriamine, dissolved in 60 ml of dimethylformamide, is added drop by drop to the thus produced active ester solution, and it is stirred for 2 hours at 0° C. and for 12 hours at room temperature. For working-up, precipitated dicyclohexylurea is filtered out, and the solvent is drawn off until a dry state is reached. The thus obtained residue is then chromatographed on silica gel (mobile solvent: dichloromethane/ethanol 15:1; chromatography was performed with use of a solvent gradient with continuous increase of the proportion of ethanol).

Yield: 26.0 g (58.8% of theory, relative to the amine component that is used) of the title compound in the form of a colorless and strongly viscous oil.
Elementary analysis:

| | | | | |
|---|---|---|---|---|
| Cld: | C 52.74 | H 5.78 | N 11.96 | F 13.90 |
| Fnd: | C 52.66 | H 5.89 | N 11.88 | F 14.02 | b) 1,4,7-Triazaheptane-1,7-bis-(2-N-trifluoroacetyl-6-N-benzyloxycarbonyl-L-lysine)-diamide-4-[2-(N-ethyl-N-perfluorooctylsulfonyl)-amino]-acetyl 16.18 g (27.0 mmol) of 2-[N-ethyl-N-perfluorooctylsulfonyl)-aminoacetic acid (production according to: DE 196 03 033), dissolved in 50 ml of tetrahydrofuran, is added to a solution that consists of 20 g (24.4 mmol) of the diamide that is produced under 14a) dissolved in a mixture that consists of 150 ml of tetrahydrofuran and 15 ml of chloroform at 0° C. and under nitrogen atmosphere. Then, a total of 18.0 g (36.6 mmol) of EEDQ [2-ethoxy-1-ethoxycarbonyl-1,2-dihydroquinoline] is added in portions at 0° C., and it is allowed to stir overnight at room temperature and then concentrated by evaporation in a vacuum. The remaining oil is chromatographed on silica gel (mobile solvent: n-hexane/isopropanol 15:1). 24.74 g (72.4% of theory, relative to the sec-amine that is used) of the title compound is obtained in the form of a colorless oil.

Elementary analysis:

| | | | | | |
|---|---|---|---|---|---|
| Cld: | C 42.01 | H 3.96 | F 31.19 | N 8.00 | S 2.29 |
| Fnd: | C 41.92 | H 4.07 | F 31.22 | N 7.87 | S 2.34 | c) 1,7-Bis-(6-N-benzyloxycarbonyl-L-lysine)-diamide-4-[2-(N-ethyl-N-perfluorooctylsulfonyl)-amino]-acetyl-1,4,7-triazaheptane 22.0 g (15.7 mmol) of the title compound that is produced under Example 14b) is dissolved in 100 ml of ethanol, and ammonia gas is introduced into this solution at 0° C. for 40 minutes. Then, it is stirred for another 4 hours at 0° C. and for 3 hours at room temperature and evaporated to the dry state in a vacuum at a bath temperature of 40° C. The remaining oily residue is purified on silica gel with use of dichloromethane/hexane/2-propanol (20:10:1) as an eluant.

Yield: 12.92 g (98.4% of theory) of the above-mentioned title compound as a colorless and strongly viscous oil.
Elementary analysis:

| | | | | | |
|---|---|---|---|---|---|
| Cld: | C 44.22 | H 4.64 | N 9.38 | S 2.68 | F 27.03 |
| Fnd: | C 44.31 | H 4.72 | N 9.30 | S 2.74 | F 26.99 | d) 1,7-Bis-[6-N-benzyloxycarbonyl-2-N-(1-O-α-D-carbonylmethyl-2,3,4,6-tetra-O-benzyl-mannopyranose)-L-lysine]-diamide-4-[2-(N-ethyl-N-perfluorooctylsulfonyl)-amino]-acetyl-1,4,7-triazaheptane 5.47 g (9.15 mmol) of 1-carboxymethyloxy-2,3, 4-tetra-O-benzyl-α-D-mannopyranoside [production as described in Patent DE 197 28 954 C1] is dissolved in 80 ml of dimethylformamide and mixed with a total of 1.05 g (9.15 mmol) of N-hydroxysuccinimide. It is cooled to 0° C., and 1.9 g (9.15 mmol) of dicyclohexylcarbodiimide is added. It is stirred for one hour at 0° C. and then for 4 hours at room temperature. It is cooled to 0° C., and a solution that consists of 7.65 g (9.15 mmol) of the amino compound, described under Example 14c) and dissolved in 50 ml of dimethylformamide, is slowly added in drops within 3 hours. It is stirred for one more hour at 0° C., then overnight at room temperature. It is evaporated to the dry state in a vacuum, and the residue is taken up in 100 ml of ethyl acetate., Precipitated urea is filtered out, and the filtrate is washed twice with 50 ml each of 5% aqueous soda solution. The organic phase is dried on magnesium sulfate and evaporated to the dry state in a vacuum. The residue is chromatographed on silica gel (mobile solvent: n-hexane/isopropanol 20:1). 17.01 g (78.9% of theory, relative to the carboxylic acid that is used) of the title compound is obtained in the form of a colorless oil.

| Elementary analysis: | | | | | |
|---|---|---|---|---|---|
| Cld: | C 59.13 | H 5.43 | N 4.76 | F 13.71 | S 1.36 |
| Fnd: | C 59.22 | H 5.39 | N 4.85 | F 13.70 | S 1.40 | e) 1,7-Bis-[2-N-(1-O-α-D-carbonylmethyl-mannopyranose)-L-lysine]-diamide-4-[2-(N-ethyl-N-perfluorooctylsulfonyl)-aminol-acetyl-1,4,7-triazaheptane 15.0 g (6.36 mmol) of the amide, produced under 14d), is dissolved in 150 ml of ethanol, and it is mixed with 0.5 g of Pearlman's catalyst (Pd 20%, C). It is hydrogenated at room temperature under a hydrogen atmosphere (1 atm) until no more hydrogen absorption can be observed. Catalyst is suctioned out, it is thoroughly rewashed with ethanol (about 100 ml) and evaporated to the dry state in a vacuum. The title compound is obtained as a strongly viscous, yellowish oil.

| Yield: | 8.54 g (97.2% of theory) | | | | |
|---|---|---|---|---|---|
| | Elementary analysis: | | | | |
| Cld: | C 39.13 | H 5.04 | N 8.11 | F 23.38 | S 2.32 |
| Fnd: | C 39.07 | H 4.98 | N 8.18 | F 23.40 | S 2.30 | f) 1,7-Bis-[2-N-(1-O-α-D-carbonylmethyl-mannopyranose)-6-N-[1,4,7-tris(carboxylatomethyl)-10-(3-aza-4-oxo-5-methyl-5-yl-pentanoyl)-1,4,7,10-tetraazacyclododecane ]-L-lysine]-diamide-4-[2-(N-ethyl-N-perfluorooctylsulfonyl)-amino]-acetyl-1,4,7-triazaheptane, digadolinium complex A stirred suspension of 5.7 g (9.06 mmol) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid in 75 ml of absolute dimethyl sulfoxide is mixed at 70° C. with 0.68 g (15.9 mmol) of lithium chloride. After 30 minutes of stirring at 70° C., the now clear reaction solution is mixed in portions with a total of 1.83 g (15.9 mmol) of N-hydroxysuccinimide, and the reaction mixture is kept at this temperature for 1 more hour. After cooling to 0° C., it is mixed with 4.52 g (23.85 mmol) of dicyclohexylcarbodiimide, and the reaction solution is stirred for another hour at 0° C., followed by 12 hours at 22° C. The thus obtained reaction solution of N-hydroxysuccinimide ester of the Gd complex of 10-(4-carboxy-1-methyl-2-oxo-3-azabutyl)-1,4,7,10-tetraazacyclododecane-1,4,7-triacetic acid is now mixed at 22° C. drop by drop with a solution of 2.84 g (2.06 mmol) of the title compound of Example 14e) in 15 ml of absolute dimethyl sulfoxide, and it is stirred for another 12 hours at room temperature. For working-up, the reaction solution is added in drops at 22° C. in 500 ml of acetone, whereby the title compound precipitates as colorless precipitate. The precipitate is suctioned off, dissolved in 200 ml of distilled water and ultrafiltered three times with a YM3-ultrafiltration membrane (AMICON(R): cut-off: 3,000 Da) for the purpose of desalination and the separation of low-molecular components. The thus obtained retentate is then freeze-dried.

| Yield: | 4.80 g (89.6% of theory, relative to the amine component that is used) as a colorless lyophilizate with a water content of 8.98%. | | | | | |
|---|---|---|---|---|---|---|
| | Elementary analysis (relative to anhydrous substance): | | | | | |
| Cld: | C 38.28 | H 4.84 | N 9.68 | F 12.40 | S 1.23 | Gd 12.07 |
| Fnd: | C 38.20 | H 4.91 | N 9.77 | F 12.45 | S 1.19 | Gd 12.10 |

EXAMPLE 15 a) 1,7-Bis(benzyloxycarbonyl)-4-{3-oxa-pentane-1,5-dicarboxylic acid-1-oyl-5-[1-(4-perfluorooctylsulfonyl)-piperazine]-amide}-1,4,7,10-tetraazacyclododecane 16.56 g (24.4 mmol) of the title compound of Example 15e), dissolved in 150 ml of tetrahydrofuran, is added at 0° C. and under nitrogen atmosphere to a solution of 10.75 g (24.4 mmol) of 1,7-bis-[benzyloxycarbonyl]-1,4,7,10-tetraazacyclododecane, dissolved in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C. and allowed to stir overnight at room temperature and then concentrated by evaporation in a vacuum. The remaining oil is chromatographed on silica gel (mobile solvent: n-hexane/isopropanol 12:1). 17.22 g (64.3% of theory, relative to the sec-amine that is used) of the monoamide and 3.8 g (8.8% of theory) of the diamide are obtained as by-products. The title compound is isolated in the form of a colorless oil.

| Elementary analysis: | | | | | |
|---|---|---|---|---|---|
| Cld: | C 43.41 | H 3.92 | F 29.18 | N 7.59 | S 2.60 |
| Fnd: | C 43.52 | H 4.07 | F 29.24 | N 7.67 | S 2.55 | b) 1,7-Bis(benzyloxycarbonyl)-4-{3-oxa-pentane-1,5-dicarboxylic acid-1-oyl-5-[1-(4-perfluorooctylsulfonyl)-piperazine]-amide }-10-[1-O-α-D-(5-carbonyl)-pentyl-2,3,4,6-tetra-O-benzyl-mannopyranose]-1,4,7,10-tetraazacyclododecane 10.0 g (13.4 mmol) of the carboxylic acid that is produced under Example 10c) and 3.24 g (28.1 mmol) of N-hydroxysuccinimide are dissolved in 100 ml of dimethylformamide and mixed in portions at 0° C. with a total of 5.8 g (28.1 mmol) of N,N'-dicyclohexylcarbodiimide, and it is stirred for 3 more hours at this temperature. A solution, cooled to 0° C., of 14.83 g (13.4 mmol) of the title compound of Example 15a), dissolved in 100 ml of dimethylformamide, is added drop by drop to the thus produced active ester solution, and it is stirred for 2 hours at 0° C. and for 12 hours at room temperature. For working-up, precipitated dicyclohexylurea is filtered out, and the solvent is drawn off until a dry state is reached. The thus obtained residue is then chromatographed on silica gel (mobile solvent: dichloromethane/ethyl acetate 20:1; the chromatography was carried out with use of a solvent gradient with continuous increase of the proportion of ethyl acetate).

| Yield: | 18.3 g (78.2% of theory) of the title compound in the form of a colorless and strongly viscous oil. Elementary analysis: | | | | |
|---|---|---|---|---|---|
| Cld: | C 55.11 | H 5.03 | N 4.82 | F 18.52 | S 1.84 |
| Fnd: | C 54.87 | H 4.85 | N 4.92 | F 18.55 | S 1.86 | c) 1-{3-oxa-pentane-1,5-dicarboxylic acid-1-oyl-5-[1-(4-perfluorooctylsulfonyl)-piperazine]-amide}-7-[1-O-α-D-(5-carbonyl)-pentyl-mannopyranose]-1,4,7,10-tetraazacyclododecane 17.0 g (9.75 mmol) of the compound that is produced under 14b) is dissolved in 150 ml of ethanol, mixed with 1.0 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with methanol (twice with 75 ml each) and evaporated to the dry state in a vacuum. The title compound is obtained as a strongly viscous and colorless oil.

| Yield: | 10.76 g (99.0% of theory). Elementary analysis: | | | | |
|---|---|---|---|---|---|
| Cld: | C 38.78 | H 4.61 | N 7.54 | F 28.97 | S 2.88 |
| Fnd: | C 38.86 | H 4.65 | N 7.41 | F 29.02 | S 2.92 | d) 1,7-Bis-[1,4,7-tris(carboxylatomethyl)-1,4,7,10-tetraazacyclododecane-Gd-complex-10-(pentanoyl-3-aza-4-oxo-5-methyl-5yl)-4-[2-(N-ethyl-N-perfluorooctylsulfonyl]-amino]-acetyl-2-oxa-acetyl]-10-[1-O-α-D-6-carbonylpentyl-mannopyranose]-1,4,7,10-tetraazacyclododecane 24.86 g (39.46 mmol; 4.4 molar equivalents relative to the amine component 15c) that is used of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 1.67 g of anhydrous lithium chloride (39.46 mmol) are dissolved at 40° C. in 200 ml of absolute dimethyl sulfoxide while being stirred and mixed at this temperature with a total of 4.53 g (39.46 mmol) of N-hydroxysuccinimide and 10.0 g (8.97 mmol) of the title compound of Example 14c), dissolved in 100 ml of absolute dimethyl sulfoxide. After cooling to room temperature, the reaction solution is mixed with 8.14 g (39.46 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cutoff: 3,000 Da), and low-molecular components are removed. The retentate is then freeze-dried.

| Yield: | 16.37 g (79.3% of theory) as a colorless lyophilizate. | | | | |
|---|---|---|---|---|---|
| H₂O content (Karl-Fischer): | 7.65%. | | | | |
| Elementary analysis (relative to anhydrous substance): | | | | | |
| Cld: | C 38.01 | H 4.61 | N 9.58 | F 13.81 | S 1.37 Gd 13.45 |
| Fnd: | C 37.92 | H 4.55 | N 9.58 | F 13.77 | S 1.31 Gd 13.48 | e) 3-Oxa-pentane-1,5-dicarboxylic acid-mono-[1-(4-perfluorooctylsulfonyl)-piperazine]-amide 25 g (44.0 mmol) of 1-perfluorooctylsulfonylpiperazine is dissolved in 150 ml of tetrahydrofuran and mixed at room temperature with a total of 5.1 g (44.0 mmol) of diglycolic acid anhydride, and the thus obtained reaction solution is refluxed for 12 hours. After cooling to room temperature, it is evaporated to the dry state, and the remaining oily residue is purified on silica gel with use of dichloromethane/2-propanol (16:1) as an eluant.

| Yield: | 27.94 g (92.8% of theory) of the above-mentioned title compound in the form of a colorless and viscous oil. Elementary analysis: | | | | |
|---|---|---|---|---|---|
| Cld: | C 58.52 | H 4.27 | N 1.98 | S 2.26 | F 22.80 |
| Fnd: | C 58.42 | H 4.41 | N 1.80 | S 2.28 | F 23.02 |

EXAMPLE 16 b) 1,7-Bis(benzyloxycarbonyl)-4-{3-oxa-pentane-1,5-dicarboxylic acid-1-oyl-5-[1-(4-perfluorooctylsulfonyl) -piperazine]-amide}-10-[1-O-β-D-6-carbonylpentyl-2,3,4,6-tetra-O-benzyl-glucopyranose]-1,4,7,10-tetraazacyclododecane)

68.5 g (91.79 mmol) of 1-carboxymethyloxy-2,3,4-tetra-O-benzyl-α-D-mannopyranoside [production as described in Patent DE 197 28 954 C1] is dissolved in 750 ml of dry tetrahydrofuran, and then 9.25 g (91.79 mmol) of triethylamine is added. After the reaction solution is cooled to −15° C. to −20° C., a solution of 12.64 g (92.5 mmol) of isobutyl chloroformate in 150 ml of dry tetrahydrofuran is slowly added in drops at this temperature while being stirred, whereby the rate of addition by drops can be selected in such a way that an internal temperature of −10° C. is not exceeded. After a reaction time of 15 minutes at −15° C., a solution of 101.6 g (91.79 mmol) of the title compound of Example 15a) and 9.25 g (91.79 mmol) of triethylamine are then slowly added in drops as solution in 500 ml of dry tetrahydrofuran at −20° C. After a reaction time of one hour at −15° C. and two hours at room temperature, the reaction solution is evaporated to the dry state in a vacuum. The remaining residue is taken up in 450 ml of ethyl acetate and washed twice with 300 ml each of saturated sodium bicarbonate solution and once with 400 ml of water. After the organic phase is dried on sodium sulfate, salt is suctioned out, and the ethyl acetate is drawn off in a vacuum. The remaining oily residue is purified on silica gel with use of dichloromethane/hexane/2-propanol (10:20:1) as an eluant.

| Yield: | 130.6 g (81.6% of theory) of the above-mentioned title compound as a colorless and strongly viscous oil. Elementary analysis: | | | | |
|---|---|---|---|---|---|
| Cld: | C 55.11 | H 5.03 | N 4.82 | F 18.52 | S 1.84 |
| Fnd: | C 55.20 | H 5.09 | N 4.91 | F 18.48 | S 1.80 | b) 1-{3-Oxa-pentane-1,5-dicarboxylic acid-1-oyl-5-[1-(4-perfluorooctylsulfonyl)-piperazine]-amide}-7-[1-O-α-D-(5-carbonyl)-pentyl-mannopyranose]-1,4,7,10-tetraazacyclododecane 110.0 g (63.08 mmol) of the compound, produced under 16a), is dissolved in 1000 ml of ethanol, mixed with 5.0 g of Pearlman's catalyst (Pd 20%, C) and hydrogenated until quantitative hydrogen uptake is reached. Catalyst is suctioned out, it is rewashed with ethanol and evaporated to the dry state in a vacuum. The title compound is obtained as a viscous and colorless oil.

| Yield: | 92.61 g (99.5% of theory) Elementary analysis: | | | | |
|---|---|---|---|---|---|
| Cld: | C 52.10 | H 5.12 | N 5.70 | F 21.89 | S 2.17 |
| Fnd: | C 52.20 | H 5.09 | N 5.71 | F 21.87 | S 2.20 | b) 1,7-Bis-[1,4,7-tris(carboxylatomethyl)-10-(3-aza-4-oxo-5-methyl-5-yl-pentanoyl)-4-{3-oxa-pentane-1,5-dicarboxylic acid-1-oyl-5-[1-(4-perfluorooctylsulfonyl)-piperazine]-amide}-10-[-O-α-D-(5-carbonyl)-pentyl-mannopyranose]-1,4,7,10-tetraazacyclododecane, digadolinium complex 55.4 g [88.0 mmol; 4.4 molar equivalents relative to the diamine component that is used of Example 13d)] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 3.7 g of anhydrous lithium chloride (88.0 mmol) are dissolved at 40° C. in 500 ml of absolute dimethyl sulfoxide while being stirred and mixed at this temperature with a total of 10.1 g (88.0 mmol) of N-hydroxysuccinimide and 29.5 g (20.0 mmol) of the title compound of Example 16b), dissolved in 200 ml of absolute dimethyl sulfoxide. After cooling to room temperature, the reaction solution is mixed with 18.2 g (88.0 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off 3,000 Da), and low-molecular components are removed. The retentate is then freeze-dried.

| Yield: | 35.96 g (76.9% of theory) as a colorless lyophilizate. | | | | |
|---|---|---|---|---|---|
| H₂O content (Karl-Fischer): | 5.98% | | | | |
| | Elementary analysis (relative to anhydrous substance): | | | | |
| Cld: | C 38.01 | H 4.61 | N 8.22 | F 13.81 | Gd 13.45 S 1.37 |
| Fnd: | C 37.87 | H 4.70 | N 8.22 | F 13.90 | Gd 13.48 S 1.36 |

EXAMPLE 17 b) 5-(Ethoxycarbonyl)pentyl-2,3,4,6-tetra-O-acetyl-α-D-mannopyranoside

Analogously to what is described in the literature for the synthesis of aryl glycopyranosides [J. Conchie and G. A. Levvy in Methods in Carbohydrate Chemistry (R. L. Whistler, M. L. Wolfrom and J. N. BeMiller, Eds.), Academic Press, New York, Vol. II, 90, pp. 345–347, (1963)], the reaction of 156.2 g (400 mmol) of D-mannosepentaacetate as α,β-(α,β-ratio=4:1)-anomer mixture [for synthesis of 1,2,3,4,6-penta-O-acetyl-α,β-D-mannopyranose, cf.: M. L. Wolfrom and A. Thompson in Methods in Carbohydrate Chemistry (R. L. Whistler, M. L. Wolfrom and J. N. BeMiller, Eds.), Academic Press, New York, Vol. II, 53, pp. 211–215, (1963)] with 67 ml (400 mmol) of 6-hydroxy-hexanoic acid ethyl ester and 60.8 ml (520 mmol) of tin(IV) chloride in a total of 600 ml of 1,2-dichloroethane after column-chromatographic purification (eluant: hexane/ethyl acetate 2:1) results in the formation of 100.05 g (51% of theory) of the above-mentioned title compound as a colorless and viscous oil. By $^1$H-NMR-spectroscopic study of the thus obtained title compound, it was possible to show that the above-mentioned title compound is only the pure α-anomer.

| | Elementary analysis: | |
|---|---|---|
| Cld: | C 52.94 | H 6.77 |
| Fnd: | C 52.80 | H 6.78 | b) 5-(Carboxy)pentyl-2,3,4,6-tetra-O-benzyl-α-D-mannopyranoside

A stirred suspension of 141.0 g (289 mmol) of the title compound of Example 17a) in 200 ml of dioxane is mixed at room temperature and with simultaneous vigorous stirring in portions with a total of 238.5 g (4.26 mol) of fine-powder potassium hydroxide powder. To make the stirring easier, the reaction mixture is mixed with another 200 ml of dioxane, and the thus obtained suspension is subsequently heated to boiling heat and mixed drop by drop at this temperature with a total of 372 ml (3.128 mol) of benzyl bromide over a period of two hours. After a reaction time of 4 hours at 110° C., followed by 12 hours at room temperature, the reaction mixture is slowly poured into a total of 2.5 liters of ice water for the purpose of working-up, and the water phase is subsequently completely extracted with diethyl ether. After the thus obtained ether phase is washed and after the subsequent drying of the ether phase on sodium sulfate, salt is suctioned out, and the diethyl ether is drawn off in a vacuum. Excess benzyl bromide is then distilled off from the reaction mixture in an oil pump vacuum quantitatively at an oil bath temperature of 180° C. The thus obtained, resinous-oily residue is purified on silica gel with use of ethyl acetate/hexane (1:10) as an eluant.

| Yield: | 172.2 g (91.0% of theory) of the above-mentioned title compound in the form of a colorless and extremely viscous oil | | |
|---|---|---|---|
| | Elementary analysis: | | |
| Cld: | C 75.68 | H 7.16 | |
| Fnd: | C 75.79 | H 7.04 | | b) 5-[(Carboxy)-pentyl-2,3,4,6-tetra-O-benzyl-α-D-mannopyranoside-]N-hydroxysuccinimide ester 60.0 g (91.5 mmol) of the title compound of Example 17b) is dissolved in 750 ml of dimethylformamide and mixed with a total of 10.4 g (91.5 mmol) of N-hydroxysuccinimide. It is cooled to 0° C., and 18.9 g (91.5 mmol) of dicyclohexylcarbodiimide is added. It is stirred for one hour at 0° C. and then for 4 hours at room temperature. The solvent is drawn off in a vacuum, and the remaining residue is mixed with 100 ml of ethyl acetate and cooled to 0° C. Precipitated urea is filtered out, and the filtrate that is obtained is evaporated to the dry state in a vacuum. The thus obtained, resinous-oily residue is purified on silica gel with use of ethyl acetate/hexane (1:20) as an eluant.

| Yield: | 61.23 g (89.0% of theory) of the above-mentioned title compound in the form of a colorless and viscous oil. | | |
|---|---|---|---|
| | Elementary analysis: | | |
| Cld: | C 70.29 | H 6.57 | N 1.86 |
| Fnd: | C 70.39 | H 5.64 | N 1.91 | b) 2,6-Bis-{6-N$_\varepsilon$-2-N$_\alpha$-]-[1-O-α-D-6-carbonyl-pentyl-(2,3,4,6-tetra-O-benzyl)-mannopyranose}-L-lysine}-methyl ester A solution of 27.51 g (36.6 mmol) of the title compound of Example 17c) in 150 ml of dimethylformamide is added in drops to a solution, cooled to 0° C., that consists of 4.26 g (18.30 mmol; 0.5 molar equivalent relative to the carboxylic acid that is used) of L-lysine methyl ester-dihydrochloride (commercially available from the Bachem Company) and 4.05 g (40.26 mmol) of triethylamine in 100 ml of dimethylformamide. After the addition is completed, it is stirred for one more hour at 0° C. and then overnight at room temperature. It is evaporated to the dry state in a vacuum, and the residue is taken up in 300 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 25:1). 39.56 g (75.4% of theory) of the title compound is obtained in the form of a colorless oil.

| | Elementary analysis: | | |
|---|---|---|---|
| Cld: | C 72.88 | H 7.31 | N 1.95 |
| Fnd: | C 72.90 | H 7.29 | N 2.02 | b) 2,6-Bis-[6-N$_\varepsilon$-2-N$_\alpha$-[1-O-α-D-6-carbonyl-pentyl-(2,3,4,6-tetra-O-benzyl)-mannopyranose]]-L-lysine 30.0 g (20.92 mmol) of the compound that is produced under Example 17d) is dissolved in 150 ml of ethanol. The solution of 4 g (100.0 mmol) of sodium hydroxide in 10 ml of distilled water is then added to it, and it is stirred for 3 hours at 50° C. According to the thin-layer chromatogram, the saponification is quantitative. It is evaporated to the dry state in a vacuum, and the remaining residue is taken up in 300 ml of ethyl acetate, and the organic phase is extracted twice with 100 ml each of dilute, aqueous citric acid solution. After drying on sodium sulfate, it is filtered and evaporated to the dry state in a vacuum. The residue is chromatographed on silica gel (mobile solvent: n-hexane/isopropanol 13:1). 25.56 g (88.5% of theory) of the title compound is obtained in the form of a colorless oil.

| | Elementary analysis: | | |
|---|---|---|---|
| Cld: | C 72.88 | H 7.31 | N 1.95 |
| Fnd: | C 72.78 | H 7.33 | N 1.96 | b) 2,6-Bis-[6-N$_\varepsilon$-2-N$_\alpha$-[1-O-α-D-6-carbonyl-pentyl-(2,3,4,6-tetra-O-benzyl) -mannopyranose]-L-lysine]-N-hydroxysuccinimide ester 14.0 g (9.15 mmol) of the title compound of Example 17e) is dissolved in 100 ml of dimethylformamide and mixed with a total of 1.04 g (9.15 mmol) of N-hydroxysuccinimide. It is cooled to 0° C., and 1.89 g (9.15 mmol) of dicyclohexylcarbodiimide is added. It is stirred for one hour at 0° C. and then for 4 hours at room temperature. The solvent is then drawn off in a vacuum, and the remaining residue is mixed with 100 ml of ethyl acetate and cooled to 0° C. Precipitated urea is filtered out, and the filtrate that is obtained is evaporated to the dry state in a vacuum. The thus obtained, resinous-oily residue is purified on silica gel with use of ethyl acetate/n-hexane (1:20) as an eluant.

| Yield: | 12.94 g (92.4% of theory) of the above-mentioned title compound in the form of a colorless and viscous oil. | | |
|---|---|---|---|
| | Elementary analysis: | | |
| Cld: | C 71.40 | H 7.05 | N 2.74 |
| Fnd: | C 71.39 | H 7.14 | N 2.81 | g) 2,6-N,N'-Bis[1-O-α-D-(6-carbonyl)-pentyl-2,3,4, 6-tetra-O-benzyl-mannopyranose]-L-lysine-1,7-(1,4, 7-triazaheptane)-diamide A solution that consists of 14.0 g (9.15 mmol; 2 molar equivalents relative to the amine that is used) of the title compound of Example 17f) in 100 ml of dimethylformamide is slowly added in drops to a solution, cooled to 0° C., of 0.47 g (4.57 mmol) of diethylenetriamine in 25 ml of dimethylformamide. After addition is completed, it is stirred for one more hour at 0° C. and then overnight at room temperature. It is evaporated to the dry state in a vacuum, and the residue is taken up in 200 ml of ethyl acetate. Precipitated urea is filtered out, and the filtrate is washed twice with 50 ml each of 5% aqueous soda solution. The organic phase is dried on magnesium sulfate and evaporated to the dry state in a vacuum. The residue is chromatographed on silica gel (mobile solvent: n-hexane/isopropanol 25:1). 9.53 g (71.4% of theory) of the title compound is obtained in the form of a colorless oil.

| Elementary analysis: | | | |
| --- | --- | --- | --- |
| Cld: | C 72.79 | H 7.42 | N 3.36 |
| Fnd: | C 72.90 | H 7.39 | N 3.32 | h) 2-N-[2-(N-Ethyl-N-perfluorooctylsulfonyl)-amino]-acetyl-6-N-(benzyloxycarbonyl)-L-lysine-methylester 20.8 g (35.6 mmol) of the 2-(N-ethyl-N-perfluorooctylsulfonyl)-aminoacetic acid and 3.60 g (35.6 mmol) of triethylamine are dissolved in 200 ml of dimethylformamide, and 4.09 g (35.6 mol) of N-hydroxysuccinimide is added. It is cooled to 0° C., and 7.34 g (35.6 mmol) of dicyclohexylcarbodiimide is added. It is stirred for one hour at 0° C. and then for 4 hours at room temperature. It is cooled to 0° C., and a solution that consists of 11.77 g (35.6 mmol) of 6-N-benzyloxycarbonyl-L-lysine-methyl ester-hydrochloride and 4.0 g (40.0 mmol) of triethylamine in 100 ml of dimethylformamide are added in drops within 10 minutes. It is stirred for one hour at 0° C. then overnight at room temperature. It is evaporated to the dry state in a vacuum, and the residue is taken up in 100 ml of ethyl acetate. Precipitated urea is filtered out, and the filtrate is washed twice with 100 ml of 5% aqueous soda solution. The organic phase is dried on magnesium sulfate and evaporated to the dry state in a vacuum. The residue is chromatographed on silica gel (mobile solvent: n-hexane/ethyl acetate 20:1). 27.43 g (88.0% of theory) of a colorless oil.

| Elementary analysis: | | | | | |
| --- | --- | --- | --- | --- | --- |
| Cld: | C 38.41 | H 3.45 | N 4.80 | F 36.89 | S 3.66 |
| Fnd: | C 38.45 | H 3.38 | N 4.88 | F 37.02 | S 3.71 | b) 2-Nα-{[2-(N-Ethyl-N-perfluorooctylsulfonyl]-amino-acetyl}-6-Nε-(benzyloxycarbonyl)-L-lysine 25.0 g (28.55 mmol) of the compound that is produced under Example 17h) is dissolved in 150 ml of ethanol. The solution of 4 g (100.0 mmol) of sodium hydroxide in 10 ml of distilled water is then added to it and stirred for 3 hours at 50° C. According to the thin-layer chromatogram, the saponification is quantitative. It is evaporated to the dry state in a vacuum, and the remaining residue is taken up in 300 ml of ethyl acetate, and the organic phase is extracted twice with 100 ml each of dilute, aqueous citric acid solution. After drying on sodium sulfate, it is filtered, and it is evaporated to the dry state in a vacuum. The residue is chromatographed on silica gel (mobile solvent: n-hexane/isopropanol 10:1). 22.73 g (92.4% of theory) of the title compound is obtained in the form of a colorless oil.

| Elementary analysis: | | | | | |
| --- | --- | --- | --- | --- | --- |
| Cld: | C 37.64 | H 3.28 | N 4.88 | F 37.49 | S 3.72 |
| Fnd: | C 37.65 | H 3.38 | N 4.88 | F 37.52 | S 3.73 | j) 1,4,7-Triazaheptane-4-{2-N-[(2-(N-ethyl-N-perfluorooctylsulfonyl)-amino]-acetyl-6-N-benzyloxycarbonyl}-L-lysine-amide-1,7-bis{2,6-N,N'-bis[1-O-α-D-(5-carbonyl)-pentyl-2,3,4,6-tetra-O-benzylmannopyranose]-L-lysine-diamide}

15.33 g (17.8 mmol) of the title compound of Example 17i) and 1.80 g (17.8 mmol) of triethylamine are dissolved in 250 ml of dry tetrahydrofuran. After the reaction solution is cooled to −15° C. to −20° C., a solution of 4.92 g (35.6 mmol) of isobutyl chloroformate, dissolved in 50 ml of dry tetrahydrofuran, is slowly added in drops at this temperature while being stirred, whereby the rate of addition by drops can be selected in such a way that an internal temperature of −10° C. is not exceeded. After a reaction time of 15 minutes at −15 C., a solution of 52.0 g (17.8 mmol) of the title compound of Example 17g) and 1.80 g (17.8 mmol) of triethylamine, in 300 ml of dry tetrahydrofuran, is then slowly added in drops at −20° C. After a reaction time of one hour at −15° C. and two hours at room temperature, the reaction solution is evaporated to the dry state in a vacuum. The remaining residue is taken up in 500 ml of ethyl acetate and washed twice with 200 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:20) as an eluant.

Yield: 54.6 g (81.6% of theory) of the above-mentioned title compound as a colorless and strongly viscous oil.

| Elementary analysis: | | | | | |
| --- | --- | --- | --- | --- | --- |
| Cld: | C 65.09 | H 6.45 | N 3.72 | F 8.58 | S 0.85 |
| Fnd: | C 65.13 | H 4.41 | N 3.69 | F 8.52 | S 0.90 | k) 1,4,7-Triazaheptane-4-{2-N-[2-(N-ethyl-N-amino]-acetyl}-L-lysine-amide-1,7-bis{2,6-N,N'-bis[1-O-α-D-(5-carbonyl)-pentyl-mannopyranose]-L-lysine-diamide}

50.0 g (13.28 mmol) of the compound, produced under 17j), is dissolved in 500 ml of ethanol, mixed with 4.0 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (about 400 ml) and evaporated to the dry state in a vacuum. The title compound is obtained as a strongly viscous and colorless oil.

Yield: 26.85 g (93.0% of theory)
Elementary analysis:

| Cld: | C 45.85 | H 6.35 | N 6.44 | F 14.86 | S 1.47 |
|---|---|---|---|---|---|
| Fnd: | C 45.76 | H 6.35 | N 6.41 | F 14.92 | S 1.39 |

1) 1,4,7-Triazaheptane-4-{2-N-[2-(N-ethyl-N-perfluorooctylsulfonyl)-amino ]-acetyl-6-N-[1,4,7-tris(carboxylatomethyl)-10-(3-aza-4-oxo-5-methyl-5-yl-pentanoyl)-1,4,7,10-tetraazacyclododecane}-L-lysine-amide-1,7-bis{2,6-N,N'-bis[1-O-α-D-(5-carbonyl)-pentyl-mannopyranose]-L-lysine-diamide}, gadolinium complex 5.54 g (8.8 mmol; 2.2 molar equivalents relative to the amine components of Example 17k) that are used) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g of anhydrous lithium chloride (8.8 mmol) are dissolved at 40° C. in 60 ml of absolute dimethyl sulfoxide while being stirred and mixed at this temperature with a total of 1.01 g (8.8 mmol) of N-hydroxysuccinimide and 1.84 g (4.0 mmol) of the title compound of Example 17k), dissolved in 40 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off 3,000 Da), and low-molecular components are removed. The retentate is then freeze-dried.

Yield: 8.77 g (78.7% of theory) as a colorless lyophilizate.
$H_2O$ content (Karl-Fischer): 4.43%.
Elementary analysis (relative to anhydrous substance):

| Cld: | C 43.98 | H 5.97 | N 7.54 | F 11.59 | Gd 5.64 | S 1.15 |
|---|---|---|---|---|---|---|
| Fnd: | C 43.97 | H 6.02 | N 7.62 | F 11.61 | Cd 10.18 | S 1.15 |

EXAMPLE 18 a) 2-Nα-6-Nξ-Bis-[-1-O-α-D-carbonylmethyl-2,3,4,6-tetra-O-benzyl-mannopyranose ]-L-lysine]-methyl ester 10.95 g (18.30 mmol) of 1-carboxymethyloxy-2,3,4-tetra-O-benzyl-α-D-mannopyranoside [production as described in Patent DE 197 28 954 C1] is dissolved in 150 ml of dimethylformamide and mixed with a total of 2.09 g (18.3 mmol) of N-hydroxysuccinimide.

It is cooled to 0° C., and 3.78 g (18.3 mmol) of dicyclohexylcarbodiimide is added. It is stirred for one hour at 0° C. and then for 4 hours at room temperature. It is cooled to 0° C., and within one hour, a solution that consists of 2.13 g (9.15 mmol; 0.5 molar equivalent relative to the carboxylic acid that is used) of L-lysine methyl ester-dihydrochloride (commercially available from the Bachem Company) and 2.02 g (20.13 mmol) of triethylamine in 70 ml of dimethylformamide is added. After the addition is completed, it is stirred for one more hour at 0° C. and then overnight at room temperature. It is evaporated to the dry state in a vacuum, and the residue is taken up in 300 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 25:1). 10.05 g (82.3% of theory) of the title compound is obtained in the form of a colorless oil.

Elementary analysis:

| Cld: | C 71.94 | H 6.79 | N 2.10 |
|---|---|---|---|
| Fnd: | C 71.90 | H 6.79 | N 2.09 | b) 2-Nα-6-Nξ-Bis-[1-O-α-D-carbonylmethyl-2,3,4,6-tetra-O-benzyl-mannopyranose]benzyl-mannopyranose]-L-lysine Analogously to what is described in Example 17c) for the synthesis of the title compound that is relevant there, the methyl ester saponification of 15 g (11.23 mmol) of the title compound of Example 18a) results in the formation of 13.89 g (93.6 of theory) of the above-mentioned title compound in the form of a colorless and viscous oil.

Elementary analysis:

| Cld: | C 71.80 | H 6.71 | N 2.12 |
|---|---|---|---|
| Fnd: | C 71.84 | H 6.69 | N 2.15 | c) 2-Nα-6-Nξ-Bis-[1-O-α-D-carbonylmethyl-2,3,4,6-tetra-O-benzyl-mannopyranose ]-L-lysine-N-hydroxysuccinimide ester 12.09 g (9.15 mmol) of the title compound of Example 18d) is dissolved in 100 ml of dimethylformamide and mixed with a total of 1.04 g (9.15 mmol) of N-hydroxysuccinimide. It is cooled to 0° C., and 1.89 g (9.15 mmol) of dicyclohexylcarbodiimide is added. It is stirred for one hour at 0° C. and then for 4 hours at room temperature. The solvent is then drawn off in a vacuum, and the remaining residue is mixed with 100 ml of ethyl acetate and cooled to 0° C. Precipitated urea is filtered out, and the filtrate that is obtained is evaporated to the dry state in a vacuum. The thus obtained resinous-oily residue is purified on silica gel with use of ethyl acetate/n-hexane (1:20) as an eluant.

Yield: 12.24 g (94.4% of theory) of the above-mentioned title compound in the form of a colorless and viscous oil.
Elementary analysis:

| Cld: | C 70.27 | H 6.47 | N 2.96 |
|---|---|---|---|
| Fnd: | C 70.31 | H 6.44 | N 3.01 | d) 6-N-Benzyloxycarbonyl-2-N-{[2,6-N,N'-bis(1-O-α(-D-carbonylmethyl-2,3,4,6-tetra-O-benzyl-mannopyranose)]-L-lysyl-}-L-lysine-[1-(4-perfluorooctylsulfonyl)-piperazine]-amide 19.0 g (13.4 mmol) of the carboxylic acid-N-hydroxysuccinimide ester, produced under Example 18c), is dissolved in 75 ml of dimethylformamide and mixed drop by drop at 0° C. with a solution, cooled to 0° C., of 11.13 g (13.4 mmol) of the title compound of Example 1c), dissolved in 50.0 ml of dimethylformamide. The resulting reaction solution is stirred for 2 more hours at 0° C. and for 12 hours at room temperature. For working-up, precipitated dicyclohexylurea is filtered out, and the solvent is then drawn off in a vacuum until a dry state is reached. The thus obtained residue is chromatographed on silica gel [mobile solvent: dichloromethane/ethanol 28:1; the chromatography is performed here with use of a solvent gradient with a proportion of the polar eluant component (here:ethanol) that is used continuously increasing in the course of the chromatography].

Yield: 25.28 g (88.4% of theory) of the title compound in the form of a colorless and strongly viscous oil.
Elementary analysis:

| | | | | | |
|---|---|---|---|---|---|
| Cld: | C 59.10 | H 5.34 | N 3.94 | F 15.13 | S 1.50 |
| Fnd: | 0 59.18 | H 5.35 | N 4.02 | F 15.15 | S 1.56 | e) 2-N-{[2,6-N,N'-Bis(1-O-α-D-carbonylmethyl-mannopyranose)]-L-lysyl-L-lysine-[1-(4-perfluorooctylsulfonyl)-piperazine]-amide 20.0 g (9.37 mmol) of the compound that is produced under 18d) is dissolved in 200 ml of ethanol, mixed with 1.5 g f Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (twice with about 100 ml each) and evaporated to the dry state in a vacuum. The title compound is obtained as a strongly viscous and colorless oil.

Yield: 11.62 g (97.0% of theory)
Elementary analysis:

| | | | | | |
|---|---|---|---|---|---|
| Cld: | C 38.50 | H 4.65 | N 6.57 | F 25.25 | S 2.51 |
| Fnd: | C 38.46 | H 4.65 | N 6.51 | F 25.23 | S 2.52 | f) 6-N-[1,4,7-Tris(carboxylatomethyl)-10-(3-aza-4-oxo-5-methyl-5-yl-pentanoyl)-1,4,7,10-tetraazacyclododecane)-2-N-{[2,6-N,N'-bis (1-O-α(-D-carbonylmethyl-mannopyranose)]-L-lysyl}-L-lysine-[1-(4-perfluorooctylsulfonyl)-piperazine]-amide, Gd complex 9.98 g (15.84 mmol; 2.2 molar equivalents relative to the amine component of Example 18c) that is used) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.67 g of anhydrous lithium chloride (15.84 mmol) are dissolved at 40° C. in 100 ml of absolute dimethyl sulfoxide while being stirred and mixed at this temperature with a total of 1.82 g (15.84 mmol) of N-hydroxysuccinimide and 9.19 g (7.19 mmol) of the title compound of Example 18e), dissolved in 50 ml of absolute dimethyl sulfoxide. After cooling to room temperature, the reaction solution is mixed with 3.27 g (15.84 mmol) of N,N'-dicyclohexylcarbodiimide and stirred for 12 hours at room temperature. The suspension that is obtained is then mixed with sufficient acetone until the precipitation of the above-mentioned title compound is completed, the precipitate is suctioned off, dried, taken up in water, insoluble dicyclohexylurea is filtered off, and the filtrate is desalinated with an AMICON(R) YM-3 ultrafiltration membrane (cut-off 3,000 Da) and in this case possible, still present low-molecular components are removed at the same time. The retentate is then freeze-dried.

Yield: 11.85 g (87.2% of theory) as a colorless lyophilizate.
H₂O content (Karl-Fischer): 5.54%
Elementary analysis (relative to anhydrous substance):

| | | | | | | |
|---|---|---|---|---|---|---|
| Cld: | C 38.12 | H 4.64 | N 8.15 | F 20.38 | S 1.70 | Gd 8.32 |
| Fnd: | C 38.16 | H 4.59 | N 8.18 | F 20.37 | S 1.68 | Gd 8.28 |

EXAMPLE 19 a) 1,7-Bis(benzyloxycarbonyl)-4-(3-oxa-2H,2H,4H,4H,5H,5H-perfluorotridecanoyl)-1,4,7,10-tetraazacyclododecane 12.74 g (24.4 mmol) of the title compound of Example 19g), dissolved in 150 ml of tetrahydrofuran, is added at 0° C. and under nitrogen atmosphere to a solution of 10.75 g (24.4 mmol) of 1,7-bis-[benzyloxycarbonyl]-1,4,7,10-tetraazacyclododecane, dissolved in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C., and it is allowed to stir overnight at room temperature and then concentrated by evaporation in a vacuum. The remaining oil is chromatographed on silica gel (mobile solvent: n-hexane/isopropanol 16:1). 15.89 g (69.0% of theory, relative to the sec-amine that is used) of the monoamide and 3.8 g (8.8% of theory) of the diamide are obtained as by-products. The title compound is isolated in the form of a colorless oil.

Elementary analysis:

| | | | | |
|---|---|---|---|---|
| Cld: | C 45.77 | H 3.95 | F 34.19 | N 5.93 |
| Fnd: | C 45.72 | H 4.01 | F 34.22 | N 5.88 | b) 1,7-Bis(benzyloxycarbonyl)-4-(3-oxa-2H,2H,4H,4H,5H,5H-perfluorotridecanoyl)-10-[1-S-α-D-(2-carbonyl)-ethyl-2,3,4,6-tetra-O-acetyl-mannopyranose]-1,4,7,10-tetraazacyclododecane 7.09 g (13.4 mmol) of 3-(2,3,4,6-tetra-O-acetyl-1-thio-α-D-mannopyranosyl)-propionic acid-N-hydroxysuccinimide ester (production according to: J. Haensler et al., Bioconjugate Chem. 4, 85, (1993); Chipowsky, S., and Lee, Y. C. (1973), Synthesis of 1-Thio-aldosides; Carbohydrate Research 31, 339–346) are dissolved in 100 ml of dimethylformamide and mixed drop by drop at 0° C. with a solution, cooled to 0° C. of 12.65 g (13.4 mmol) of the title compound of Example 19a), dissolved in 100 ml of dimethylformamide. It is stirred for 2 hours at 0° C. then for 12 hours at room temperature. For working-up, the solvent is drawn off in a vacuum until a dry state is reached, and the thus obtained residue is then chromatographed on silica gel (mobile solvent: dichloromethane/ethyl acetate 20:1; the chromatography was performed with use of a solvent gradient with continuous increase of the proportion of ethyl acetate.

Yield: 16.23 g (88.9% of theory) of the title compound in the form of a colorless and strongly viscous oil.
Elementary analysis:

| | | | | | |
|---|---|---|---|---|---|
| Cld: | C 46.70 | H 4.36 | N 4.11 | F 23.69 | S 2.35 |
| Fnd: | C 46.66 | H 4.35 | N 4.12 | F 23.65 | S 2.30 | c) 1-(3-Oxa-2H,2H,4H,4H, 5H,5H-perfluorotridecanoyl)-7-[1-S-α-D-(2-carbonyl)-ethyl-2,3,4,6-tetra-O-acetyl-mannopyranose]-1,4,7,10-tetraazacyclododecane 15.0 g (11.0 mmol) of the compound that is produced under 19b) is dissolved in 150 ml of ethanol, mixed with 1.0 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (twice with 75 ml each) and evaporated to the dry state in a vacuum. The title compound is obtained as a strongly viscous and colorless oil.

Yield: 11.56 g (96.0% of theory).
Elementary analysis:

| | | | | | |
|---|---|---|---|---|---|
| Cld: | C 40.59 | H 4.33 | N 5.12 | F 29.50 | S 2.93 |
| Fnd: | C 40.63 | H 4.35 | N 5.11 | F 29.52 | S 2.92 | d) 1-(3-Oxa-2H,2H,4H,4H,5H,5H-perfluorotridecanoyl)-7-[1-S-α-D-(2-carbonyl)-ethyl-mannopyranose]-1,4,7,10-tetraazacyclododecane 10.0 g (9.13 mmol) of the title compound of Example 19c) is suspended in 100 ml of absolute methanol and mixed at 5° C. with a catalytic amount of sodium methanolate. After a reaction time of 3 hours at room temperature, even thin-layer chromatographic checking (eluant: chloroform/methanol 4:1) of the plot of the reaction indicates a quantitative reaction. For the purpose of working-up, the now clear reaction solution is neutralized by mixing with Amberlite IR 120 (H⁻ form)-cation-exchange resin, exchanger is suctioned out, rewashed with methanol, and the thus obtained methanolic filtrate is drawn off in a vacuum until a dry state is reached. The oily residue that is obtained is purified by column chromatography on silica gel (mobile solvent: dichloromethane/n-hexane/ethyl acetate 15:20:1; the chromatography was performed with use of a solvent gradient with continuous increase of the proportion of ethyl acetate). After $^1$H-NMR-spectroscopic study of the title compound, the presence of the α-configuration at the anomeric center of the D-mannopyranose was definitively established based on the size of the coupling constant of $J_{1,2}$=0.9 Hz. This α-configuration is the sole existing configuration at the anomeric center, i.e., the amount of the β-configured anomer of the title compound that can possibly be formed thus lies below the $^1$H-NMR-spectroscopic detection limit. The above-mentioned title compound was accordingly represented only in the form of the pure α-configured anomer.

Yield: 8.28 g (98.0% of theory) of the title compound in the form of a colorless and strongly viscous oil.
Elementary analysis:

| | | | | | |
|---|---|---|---|---|---|
| Cld: | C 37.59 | H 4.24 | N 6.05 | F 34.85 | S 3.46 |
| Fnd: | C 37.57 | H 4.28 | N 6.02 | F 34.85 | S 3.44 | e) 1-(3-Oxa-2H,2H,4H,4H, 5H,5H-perfluorotridecanoyl)-7-[1-S-α-D-(2-carbonyl)-ethyl-mannopyranose]-4,10-bis[1,4,7-tris(carboxylatomethyl)-10-(3-aza-4-oxo-5-methyl-5-yl-pentanoyl) ]-1,4,7,10-tetraazacyclododecane, digadolinium complex 2.48 g [(3.94 mmol); 4.4 molar equivalents relative to the diamine component of 19d) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 167 mg of anhydrous lithium chloride (3.94 mmol) are dissolved at 40° C. in 40 ml of absolute dimethyl sulfoxide while being stirred and mixed at this temperature with a total of 453 mg (3.94 mmol) of N-hydroxysuccinimide and 980 mg (0.895 mmol) of the title compound of Example 19d), dissolved in 10 ml of absolute dimethyl sulfoxide. After cooling to room temperature, the reaction solution is mixed with 814 mg (3.946 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON$^{(R)}$ YM-3 ultrafiltration membrane (cut-off 3,000 Da), and low-molecular components are removed. The retentate is then freeze-dried.

Yield: 1.32 g (69.1% of theory) as a colorless lyophilizate.
H$_2$O content (Karl-Fischer): 7.65%
Elementary analysis (relative to anhydrous substance):

| | | | | | | |
|---|---|---|---|---|---|---|
| Cld: | C 37.43 | H 4.45 | N 9.12 | F 15.02 | S 1.49 | Gd 14.63 |
| Fnd: | C 37.42 | H 4.50 | N 9.18 | F 15.07 | S 1.51 | Gd 14.58 | f) 3-Oxa-2H,2H,4H,4H,5H,5H-perfluorotridecanoic acid-t-butyl ester 25.0 g (53.8 mmol) of 1H,1H,2H,2H-perfluoro-1-decanol [commercially available from the Lancaster Company] is dissolved in 250 ml of absolute toluene and mixed at room temperature with a catalytic amount (about 0.75 g) of tetra-N-butyl-ammonium hydrogen sulfate Then, a total of 7.55 g (134.6 mmol; 2.5 equivalents relative to the alcohol component that is used) of fine-powder potassium hydroxide powder is added at 0° C., followed by 15.73 g (80.7 mmol; 1.5 equivalents relative to the alcohol component that is used) of bromoacetic acid-tert-butyl ester, and it is allowed to stir for 2 more hours at 0° C. The thus obtained reaction solution is stirred for 12 hours at room temperature and for the purpose of working-up, it is mixed with a total of 500 ml of ethyl acetate and 250 ml of water. The organic phase is separated and washed twice with water. After the organic phase is dried on sodium sulfate, salt is suctioned out, and the solvent is drawn off in a vacuum. The remaining oily residue is purified on silica gel with use of ethyl acetate/hexane (1:10) as an eluant.

Yield: 26.3 g (84.6% of theory) of the above-mentioned title compound as a colorless and strongly viscous oil
Elementary analysis:

| Cld: | C 33.23 | H 2.61 | F 55.85 |
|---|---|---|---|
| Fnd: | C 33.29 | H 2.61 | F 55.90 | g) 3-Oxa-2H,2H,4H,4H,5H,5H-perfluorotridecanoic carboxylic acid 20.0 g (34.58 mmol) of the title compound of Example 19f) is suspended in 200 ml of a mixture that consists of methanol and 0.5 molar sodium hydroxide solution at a ratio of 2:1 while being stirred at room temperature, and then it is heated to 60° C. After a reaction time of 12 hours at 60° C., the now clear reaction mixture is neutralized for working-up by mixing with Amberlite IR 120 ($H^+$ form)-cation-exchange resin, exchanger is suctioned out, and the thus obtained methanolic-aqueous filtrate is evaporated to the dry state in a vacuum. The amorphous-oily residue that is obtained is purified on silica gel with use of ethyl acetate/n-hexane (1:3) as an eluant.

Yield: 16.0 g (88.6% of theory) of the above-mentioned title compound as a colorless and strongly viscous oil
Elementary analysis:

| Cld: | C 27.60 | H 1.35 | F 61.85 |
|---|---|---|---|
| Fnd: | C 27.58 | H 1.36 | F 61.90 |

EXAMPLE 20 a) 6-Benzyloxycarbonyl-2-[2-(N-ethyl-N-perfluorooctylsulfonyl)-amino]-acetyl-L-lysine-methyl ester 16.18 g (27.0 mmol) of 2-[N-ethyl-N-perfluorooctylsulfonyl)-aminoacetic acid (production according to: DE 196 03 033), dissolved in 50 ml of tetrahydrofuran, is added drop by drop to 8.0 g (24.4 mmol) of ξ-carbonyloxybenzyl-L-lysine methyl ester hydrochloride (commercially available from the Bachem Company), dissolved in a mixture that consists of 150 ml of tetrahydrofuran, 15 ml of chloroform, and 2.62 g (26.0 mmol) of triethylamine at 0° C. and under nitrogen atmosphere. Then, a total of 18.0 g (36.6 mmol) of EEDQ [2-ethoxy-1-ethoxycarbonyl-1,2-dihydroquinoline] is added in portions at 0° C. and allowed to stir overnight at room temperature. It is then concentrated by evaporation in a vacuum, and the remaining oil is chromatographed on silica gel (mobile solvent: n-hexane/isopropanol 15:1). 17.0 g (79.6% of theory, relative to the primary amine that is used) of the title compound is obtained in the form of a colorless oil.

Elementary analysis:

| Cld: | C 33.41 | H 3.45 | F 36.89 | N 4.80 | S 3.66 |
|---|---|---|---|---|---|
| Fnd: | C 38.42 | H 3.47 | F 36.92 | N 4.87 | S 3.64 | b) 2-[2-(N-Ethyl-N-perfluorooctylsulfonyl)-amino]-acetyl-L-lysine-methyl ester 15.0 g (20.23 mmol) of the compound that is produced under Example 20a) is dissolved in 200 ml of ethanol, mixed with 800 mg of Pearlman's catalyst (Pd 20% on activated carbon) and hydrogenated until the calculated amount of hydrogen is taken up. Catalyst is suctioned out, it is thoroughly rewashed with ethanol and evaporated to the dry state in a vacuum. The title compound is obtained as a colorless oil.

Yield: 14.68 g (97.9% of theory)
Elementary analysis:

| Cld: | C 32.40 | H 3.26 | F 43.56 | N 5.67 | S 4.32 |
|---|---|---|---|---|---|
| Fnd: | C 32.42 | H 3.27 | F 43.60 | N 5.67 | S 4.34 | c) 6-(1-O-α-D-Carbonylmethyl-2,3,4,6-tetra-O-benzyl-mannopyranose) 2-[2-(N-ethyl-N-perfluorooctylsulfonyl)-amino]-acetyl-L-lysine-methyl ester 21.31 g (35.6 mmol) of 1-carboxymethyloxy-2,3,4-tetra-O-benzyl-α-D-mannopyranoside [production as described in Patent DE 197 28 954 C1] and 3.60 g (35.6 mmol) of triethylamine are dissolved in 500 ml of dry tetrahydrofuran. After the reaction solution is cooled to −15° C. to −20° C., a solution of 4.92 g (35.6 mmol) of isobutyl chloroformate in 75 ml of dry tetrahydrofuran is slowly added in drops at this temperature while being stirred, whereby the rate of addition by drops can be selected in such a way that an internal temperature of −10° C. is not exceeded. After a reaction time of 15 minutes at −15° C., a solution of 26.39 g (35.6 mmol) of the title compound of Example 20b) and 3.60 g (35.6 mmol) of triethylamine, in 100 ml of dry tetrahydrofuran, is then slowly added in drops at −20° C. After a reaction time of one hour at −15° C. and two hours at room temperature, the reaction solution is evaporated to the dry state in a vacuum. The remaining residue is taken up in 250 ml of ethyl acetate and washed twice with 100 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:10) as an eluant.

| Yield: | 38.12 g (81.0% of theory) of the above-mentioned title compound as a colorless and strongly viscous oil Elementary analysis: | | | | |
|---|---|---|---|---|---|
| Cld: | C 49.92 | H 3.92 | N 2.53 | F 29.18 | S 2.90 |
| fnd: | C 49.99 | H 4.11 | N 2.69 | F 29.22 | S 3.01 | d) 6-(1-O-α-D-Carbonylmethyl-2,3,4,6-tetra-O-benzyl-mannopyranose) 2-[2-(N-ethyl-N-perfluorooctylsulfonyl)-amino]-acetyl-L-lysine 27.65 g (20.92 mmol) of the compound that is produced under Example 20c) is dissolved in 250 ml of methanol. The solution of 4.0 g (100.0 mmol) of sodium hydroxide in 10 ml of distilled water is then added to it, and it is stirred for 3 hours at 50° C. After the course of the reaction is checked by means of thin-layer chromatography, methyl ester saponification has already taken place quantitatively. It is evaporated to the dry state in a vacuum, the remaining residue is taken up in 300 ml of ethyl acetate, and the organic phase is extracted twice with 100 ml each of dilute, aqueous citric acid solution. After drying on sodium sulfate, it is filtered and evaporated to the dry state in a vacuum. The residue that is obtained is chromatographed on silica gel (mobile solvent: n-hexane/chloroform/isopropanol 15:10:1). 24.31 g (88.9% of theory) of the title compound is obtained in the form of a colorless and viscous oil.

| Elementary analysis: | | | | | |
|---|---|---|---|---|---|
| Cld: | C 51.46 | H 4.70 | N 3.21 | F 24.71 | S 2.45 |
| Fnd: | C 51.49 | H 4.71 | N 3.19 | F 24.72 | S 2.41 | c) 6-(1-O-α-D-Carbonylmethyl-mannopyranose) 2-[2-(N-ethyl-N-perfluorooctylsulfonyl)-amino [-acetyl-L-lysine 20.0 g (15.30 mmol) of the title compound of Example 20d) is dissolved in a mixture that consists of 250 ml of 2-propanol and 25 ml of water, and it is mixed with 1.0 g of palladium catalyst (10% Pd on activated carbon). It is hydrogenated for 12 hours at room temperature and a hydrogen pressure of one atmosphere. Catalyst is filtered out, and the filtrate is evaporated to the dry state in a vacuum. The residue is dissolved in 200 ml of methanol, and the reaction product is precipitated by mixing with a total of 800 ml of diethyl ether. After the thus obtained solid is suctioned off, the latter is dried in a vacuum at 50° C.

| Yield: | 14.32 g (99.0% of theory) of an amorphous solid. | | | | |
|---|---|---|---|---|---|
| | Elementary analysis: | | | | |
| Cld: | C 35.56 | H 3.34 | N 4.44 | S 3.39 | F 34.15 |
| Fnd: | C 35.58 | H 3.81 | N 4.45 | S 3.40 | F 34.17 | f) 6-(1-O-α-D-Carbonylmethyl-mannopyranose) 2-[2-(N-ethyl-N-perfluorooctylsulfonyl)-amino ]-acetyl-L-lysine-N-{2-hydroxy-prop-3-yl-[1,4,7-tris(carboxylatomethyl)-1,4,7,10-tetraazacyclododecan-10-yl[}-amide, Gd complex 7.48 g (7.91 mmol) of the title compound of Example 20e) is dissolved at 40° C. in 50 ml of dimethyl sulfoxide, and 1.00 g (8.70 mol) of N-hydroxysuccinimide is added. It is cooled to 20° C., and 1.795 g (8.7 mmol) of dicyclohexylcarbodiimide is added. It is stirred for one hour at 20° C. and then for 4 hours at 40° C. Then, a solution that consists of 4.53 g (7.91 mmol) of the gadolinium complex of 10-(2-hydroxy-3-aminopropyl)-4,7,10-tris (carboxymethyl)-1,4,7,10-tetraazacyclododecanine [for production, cf.: WO 97/02051] in 20 ml of dimethyl sulfoxide is added in drops at this temperature within 10 minutes. It is stirred for one hour at 40° C., then overnight at room temperature. The thus obtained suspension is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off 3,000 Da), and low-molecular components are removed. The retentate is then freeze-dried.

| Yield: | 9.71 g (81.7% of theory) as a colorless lyophilizate. | | | | | |
|---|---|---|---|---|---|---|
| H₂O content (Karl-Fischer): | 3.97% | | | | | |
| | Elementary analysis (relative to anhydrous substance): | | | | | |
| Cld: | C 35.16 | H 4.16 | N 7.45 | F 21.48 | Gd 10.46 | S 2.13 |
| Fnd: | C 35.17 | H 4.20 | N 7.42 | F 21.49 | Gd 10.48 | S 2.09 |

EXAMPLE 21 a) 6-N-[1-O-α-D-(5-Carbonyl)-pentyl-2,3,4,6-tetra-O-benzyl-mannopyranosel-2N-[2-(N-ethyl-N-perfluorooctylsulfonyl)-amino]-acetyl-L-lysine-methyl ester 5.23 g (8.0 mmol) of the 5-(carboxy)pentyl-2,3,4,6-tetra-O-benzyl-α-D-mannopyranoside, described in Example 10c), 1.3 g (8.0 mmol) of 1-hydroxybenzotriazole, and 2.6 g (8.0 mmol) of 2-(1H-benzotriazol-1-yl)-1,1,3,3-tetramethyluronium tetrafluoroborate (TBTU; Peboc Limited, UK) are dissolved in 75 ml of DMF and stirred for 15 minutes. This solution is then mixed with 5.16 ml (30 mmol) of N-ethyldiisopropylamine and with 5.93 g (8.0 mmol) of the amine that is described under Example 20b), and it is stirred for 1.5 days at room temperature. For working-up, the solvent is drawn off in a vacuum until a dry state is reached, and the thus obtained residue is then chromatographed on silica gel (mobile solvent: dichloromethane/ethyl acetate 30:1; the chromatography was carried out with use of a solvent gradient with continuous increase of the proportion of ethyl acetate).

| Yield: | 9.70 g (88.0% of theory) of the title compound in the form of a colorless and strongly viscous oil. | | | | |
|---|---|---|---|---|---|
| | Elementary analysis: | | | | |
| Cld: | C 52.29 | H 4.97 | N 3.05 | F 23.43 | S 2.33 |
| Fnd: | C 52.33 | H 4.95 | N 3.12 | F 23.50 | S 2.30 | b) 6-N-[1-O-α-D-(5-Carbonyl)-pentyl-2,3,4,6-tetra-O-benzyl-mannopyranose]-2N-[2-(N-ethyl-N-perfluorooctylsulfonyl)-amino]-acetyl-L-lysine 9.0 g (12.40 mmol) of the compound that is produced under Example 21a) is dissolved in 150 ml of methanol. The solution of 2.48 g (62.0 mmol) of sodium hydroxide in 15 ml of distilled water is then added to it, and it is stirred for 3 hours at 50° C. After the course of the reaction is checked by means of thin-layer chromatography, the methyl ester saponification has already taken place quantitatively after the above-mentioned reaction time. It is evaporated to the dry state in a vacuum, and the remaining residue is taken up in 300 ml of ethyl acetate, and the organic phase is extracted twice with 100 ml each of dilute, aqueous citric acid solution. After drying on sodium sulfate, it is filtered and evaporated to the dry state in a vacuum. The residue that is obtained is chromatographed on silica gel (mobile solvent: n-hexane/chloroform/isopropanol 25:10:1). 15.88 g (93.9% of theory) of the title compound is obtained in the form of a colorless and strongly viscous oil.

Elementary analysis:

| Cld: | C 51.95 | H 4.88 | N 3.08 | F 23.67 | S 2.35 |
|---|---|---|---|---|---|
| Fnd: | C 51.99 | H 4.91 | N 3.09 | F 23.70 | S 2.33 | c) 6-N-[1-O-α-D-(5-Carbonyl)-pentyl-mannopyranose]-2N-[2-(N-ethyl-N-perfluorooctylsulfonyl)-amino]-acetyl-L-lysine 13.0 g (9.52 mmol) of the title compound of Example 21b) is dissolved in a mixture that consists of 150 ml of 2-propanol and 25 ml of water, and 1.0 g of the palladium catalyst (10% Pd on activated carbon) is added. It is hydrogenated for 12 hours at 1 atmosphere of hydrogen pressure and at room temperature. Catalyst is filtered out, and the filtrate is evaporated to the dry state in a vacuum. The residue that is obtained is chromatographed on silica gel (mobile solvent: n-hexane/chloroform/isopropanol 15:10:1). 9.09 g (95.1% of theory) of the title compound is obtained in the form of a colorless and strongly viscous oil.

Elementary analysis:

| Cld: | C 37.10 | H 4.22 | N 4.19 | F 32.18 | S 3.10 |
|---|---|---|---|---|---|
| Fnd: | C 37.09 | H 4.21 | N 4.19 | F 32.20 | S 3.13 | d) 6-N-[1-O-α-D-(5-Carbonyl)-pentyl-mannopyranose]-2N-[2-(N-ethyl-N-perfluorooctylsulfonyl)-amino]-acetyl-L-lysine-N-{2-hydroxy-prop-3-yl-[1,4,7-tris(carboxylatomethyl)-1,4,7,10-tetraazacyclododecan-10-yl]}-amide, Gd complex 7.93 g (7.91 mmol) of the title compound of Example 21c) is dissolved at 40° C. in 75 ml of dimethyl sulfoxide, and it is mixed with 1.00 g (8.70 mol) of N-hydroxysuccinimide. It is cooled to room temperature, and a total of 1.795 g (8.7 mmol) of dicyclohexylcarbodiimide is added. It is stirred for one hour at 20° C. and then for 4 hours at 40° C. A solution that consists of 4.53 g (7.91 mmol) of the gadolinium complex of 10-(2-hydroxy-3-aminopropyl)-4,7,10-tris (carboxymethyl)-1,4,7,10-tetraazacyclododecanine [for production, cf.: WO 97/02051], in 20 ml of dimethyl sulfoxide, is then added in drops at 40° C. within 10 minutes to this solution of the active ester of the title compound of Example 21c). It is stirred for one hour at 40° C., then overnight at room temperature. The thus obtained suspension is then mixed with the sufficient amount of a mixture that consists of acetone/2-propanol (2:1) until precipitation of the above-mentioned title compound is completed, the precipitate is suctioned off, rewashed with ethyl acetate, dried, taken up in water, insoluble dicyclohexylurea is filtered out, and the filtrate is desalinated with an AMICON (R) YM-3 ultrafiltration membrane (cut-off 3,000 Da), and low-molecular components are removed. The retentate is then freeze-dried.

Yield: 9.71 g (78.8% of theory) as a colorless lyophilizate.
$H_2O$ content 6.65%
(Karl-Fischer):

Elementary analysis (relative to anhydrous substance):

| Cld: | C 36.97 | H 4.52 | N 7.19 | F 20.71 | Gd 10.08 | S 2.06 |
|---|---|---|---|---|---|---|
| Fnd: | C 37.02 | H 4.50 | N 7.22 | F 20.59 | Gd 10.08 | S 2.09 |

EXAMPLE 22 a) 6-N-{4-[2,3-Bis-(N,N-bis(t-butyloxycarbonylmethyl)-amino)-propyl]-phenyl}-3-oxa-propionyl-2-N-(1-α-D-carbonylmethyl-mannopyranose) L-lysine-[1-(4-perfluorooctylsulfonyl)-piperazine]-amide 5.25 g (7.72 mmol) of the tetra-t.bu-ester of 1-(4-carboxymethoxybenzyl)-EDTA (lit.: U.S. Pat. No. 4,622,420) and 781 mg (7.72 mmol) of triethylamine are dissolved in 50 ml of methylene chloride. At −15° C., a solution that consists of 1.16 g (8.5 mmol) of isobutyl chloroformate in 10 ml of methylene chloride is added in drops within 5 minutes, and it is stirred for another 20 minutes at −15° C. Then, the solution is cooled to −25° C., and a solution that consists of 7.07 g (7.72 mmol) of the title compound of Example 10e) and 2.12 g (21.0 mmol) of triethylamine, in 70 ml of tetrahydrofuran, is added in drops within 30 minutes and subsequently stirred for 30 more minutes at −15° C. and then stirring is continued overnight at room temperature. For working-up, the solvent is drawn off in a vacuum, and the remaining oily residue is taken up in 250 ml of chloroform. The chloroform phase is extracted twice with 100 ml each of a 10% aqueous ammonium chloride solution, the organic phase is dried on magnesium sulfate, and it is evaporated to the dry state in a vacuum. The residue is chromatographed on silica gel (mobile solvent: methylene chloride/ethanol—20:1).

Yield: 9.0 g (79.0% of theory) of a colorless and very viscous oil.
Elementary analysis:

| Cld: | C 46.39 | H 5.55 | N 5.32 | F 20.45 | S 2.03 |
|---|---|---|---|---|---|
| Fnd: | C 46.42 | H 5.51 | N 5.29 | F 20.49 | S 2.09 | b) 6-N-{4-[2,3-Bis-(N,N-bis(carboxymethyl)-amino)-propyl]-phenyl}-3-oxa-propionyl-2-N-(1-α-D-carbonylmethyl-mannopyranose) L-lysine-[1-(4-perfluorooctylsulfonyl)-piperazine]-amide 9.0 g (5.70 mmol) of the compound that is produced under Example 22a) is dissolved in 150 ml of methanol. The solution of 4.0 g (100.0 mmol) of sodium hydroxide in 25 ml of distilled water is then added to it, and it is stirred for 6 hours at 60° C. After the course of the reaction is checked by means of thin-layer chromatography, the saponification of the tetra-t.-butyl ester has already taken place quantitatively after the above-mentioned reaction time. It is evaporated to the dry state in a vacuum, and the remaining residue is taken up in 50 ml of dimethyl sulfoxide in the heat and then it is mixed with the sufficient amount of a mixture that consists of acetone/ethyl acetate (1:1) until the precipitation of the above-mentioned title compound is completed, the thus obtained precipitate is suctioned off, rewashed well with ethyl acetate, dried, taken up in water, the pH of the product solution is set at 3.5 with 1 molar hydrochloric acid, possibly existing insoluble components are filtered out, and the filtrate is desalinated with an AMICON(R) YM-3 ultrafiltration membrane (cut-off: 3,000 Da), and low-molecular components are removed. The retentate is then freeze-dried.

Yield: 6.76 g (87.6% of theory) as a colorless lyophilizate.
H$_2$O content (Karl-Fischer): 3.30%
Elementary analysis (relative to anhydrous substance):

| | | | | | |
|---|---|---|---|---|---|
| Cld: | C 39.89 | H 4.09 | N 6.20 | F 23.84 | S 2.37 |
| Fnd: | C 39.92 | H 4.15 | N 6.22 | F 23.92 | S 2.29 | c) 6-N-{4-[2,3-Bis-(N,N-bis(carboxylatomethyl)-amino)-propyl]-phenyl}-3-oxa-propionyl-2-N-(1-α-D-carbonylmethyl-mannopyranose) L-lysine-[1-(4-perfluorooctylsulfonyl)-piperazine]-amide, Mn complex, disodium salt 3.0 g (2.22 mmol) of the title compound of Example 22b) is dissolved in 150 ml of a water/ethanol (3:1) mixture at boiling heat and mixed at 80° C. in portions with 0.25 g (2.22 mmol) of manganese (II) carbonate. Then, the thus obtained reaction solution is refluxed for 5 hours. After cooling to room temperature, the solvent mixture is completely drawn off in a vacuum, and the remaining residue is dissolved in a mixture that consists of 200 ml of distilled water/n-butanol (1:1). While being stirred vigorously, it is set at a pH of 7.2 by mixing with 1N sodium hydroxide solution. After the n-butanol is completely drawn off in a vacuum, the remaining aqueous phase is desalinated with an AMICON(R) YM-3 ultrafiltration membrane (cut-off 3,000 Da), and low-molecular components are removed. The retentate is then freeze-dried.

Yield: 3.19 g (99.0% of theory) as a colorless lyophilizate.
H$_2$O content (Karl-Fischer): 5.08%.
Elementary analysis (relative to anhydrous substance):

| | | | | | | | |
|---|---|---|---|---|---|---|---|
| Cld: | C 37.23 | H 3.54 | F 22.25 | Mn 3.78 | N 5.79 | Na 3.17 | S 2.21 |
| Fnd: | C 37.30 | H 3.49 | F 22.29 | Mn 3.81 | N 5.76 | Na 3.19 | S 2.18 |

EXAMPLE 23 a) 3-Benzyloxycarbonylamino-glutaric acid-[1-(4-perfluorooctylsulfonyl)-piperazine]-monoamide A stirred solution of 25.0 g (94.96 mmol) of 3-N-(benzyloxycarbonyl)-glutaric acid-anhydride [synthesis according to: Hatanaka, Minoru; Yamamoto, Yu-ichi; Nitta, Hajime; Ishimaru, Toshiyasu; TELEAY; Tetrahedron Lett.; EN; 22; 39; 1981; 3883–3886;] in 150 ml of absolute tetrahydrofuran is mixed drop by drop while being stirred with a solution of 53.97 g (95.0 mmol) of 1-perfluorooctylsufonylpiperazine in 150 ml of tetrahydrofuran, and the thus obtained reaction solution is refluxed for 12 hours. After cooling to room temperature, it is evaporated to the dry state, and the remaining oily residue is purified on silica gel with use of dichloromethane/2-propanol (20:1) as an eluant.

Yield: 75.80 g (96.0% of theory) of the above-mentioned title compound in the form of a colorless and viscous oil.
Elementary analysis:

| | | | | | |
|---|---|---|---|---|---|
| Cld: | C 36.11 | H 2.67 | N 5.05 | S 3.86 | F 38.84 |
| Fnd: | C 36.12 | H 2.61 | N 5.08 | S 3.88 | F 38.82 | b) 3-Amino-glutaric acid-[1-(4-perfluorooctylsulfonyl)-piperazine]-monoamide 31.50 g (37.88 mmol) of the compound that is produced under 23b) is dissolved in 300 ml of ethanol, mixed with 2.5 g of Pearlman's catalyst (Pd 20% C) and hydrogenated at 1 atmosphere of hydrogen pressure until quantitative hydrogen uptake is reached. Catalyst is suctioned out, it is rewashed with ethanol and evaporated to the dry state in a vacuum. The title compound is obtained as a whitish-yellow, viscous oil.

Yield: 25.22 g (95.5% of theory)
Elementary analysis:

| | | | | | |
|---|---|---|---|---|---|
| Cld: | C 29.28 | H 2.31 | N 6.03 | S 4.06 | F 46.31 |
| Fnd: | C 29.32 | H 2.29 | N 6.08 | S 4.08 | F 46.28 | c) 3-N-(1-α-D-Carbonylmethyl-2,3,4,6-tetra-O-benzyl-mannopyranose)-glutaric acid-[1-(4-perfluorooctylsulfonyl)-piperazine[-monoamide 21.52 g (18.96 mmol) of 1-carboxymethyloxy-2,3,4-tetra-O-benzyl-α-D-mannopyranoside [production as described in Patent DE 197 28 954 C1] is dissolved at room temperature in 100 ml of absolute dimethylformamide and mixed at 0° C. with 2.56 g (22.2 mmol) of N-hydroxysuccinimide, followed by 4.55 g (22.2 mmol) of dicyclohexylcarbodiimide. After a reaction time of 60 minutes at 0° C. and 3 hours at 22° C., insoluble dicyclohexylurea is filtered out, and the thus obtained clear active ester solution of the above-mentioned title compound is slowly added in drops at 0° C. to a stirred solution of 13.22 g (18.96 mmol) of the compound of Example 23b), dissolved in 100 ml of dimethylformamide. After a reaction time of 12 hours at room temperature, the solvent is drawn off in a vacuum, and the remaining residue is taken up in 300 ml of ethyl acetate, urea is filtered out, and the organic filtrate is washed twice with 100 ml each of saturated sodium bicarbonate solution and once with 100 ml of 10% aqueous citric acid solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:15) as an eluant.

Yield: 21.39 g (88.3% of theory) of the above-mentioned title compound as a colorless and strongly viscous oil.
Elementary analysis:

| | | | | | |
|---|---|---|---|---|---|
| Cld: | C 49.81 | H 4.10 | N 3.29 | F 25.27 | S 2.51 |
| Fnd: | C 49.89 | H 4.11 | N 3.32 | F 25.22 | S 2.51 | d) 3-N-(1-α-D-Carbonylmethyl-mannopyranose)-glutaric acid-[1-(4-perfluorooctylsulfonyl)-piperazine]-monoamide 19.55 g (15.30 mmol) of the title compound of Example 23c) is dissolved in a mixture that consists of 250 ml of 2-propanol and 25 ml of water, and it is mixed with 1.5 g of palladium catalyst (10% Pd on activated carbon). It is hydrogenated for 12 hours at room temperature and a hydrogen pressure of one atmosphere. Catalyst is filtered out, and the filtrate is evaporated to the dry state in a vacuum. The residue is dissolved in 200 ml of methanol, and the reaction product is precipitated by mixing with a total of 800 ml of diethyl ether. After the thus obtained solid is suctioned off, the latter is dried in a vacuum at 40° C.

| Yield: 17.49 g (97.5% of theory) of an amorphous solid. Elementary analysis: | | | | | |
|---|---|---|---|---|---|
| Cld: | C 32.73 | H 3.08 | N 4.58 | S 3.49 | F 35.20 |
| Fnd: | C 32.68 | H 3.15 | N 4.55 | S 3.50 | F 35.17 | e) 3-N-(1-α-D-Carbonylmethyl-mannopyranose)-glutaric acid-[1-(4-perfluorooctylsulfonyl)-piperazine]-amide-5-N-{2-hydroxy-prop-3-yl-[1,4,7-tris(carboxylatomethyl)-1,4,7,10-tetraazacyclododecan-10-yl]}-amide, Gd complex 14.43 g (15.84 mmol) of the title compound of Example 23d) and 0.67 g of anhydrous lithium chloride (15.84 mmol) are dissolved at 40° C. in 100 ml of absolute dimethyl sulfoxide while being stirred and mixed at this temperature with a total of 1.82 g (15.84 mmol) of N-hydroxysuccinimide and a solution of 9.08 g (15.84 mmol) of the gadolinium complex of 10-(2-hydroxy-3-aminopropyl)-4,7,10-tris(carboxymethyl)-1,4,7,10-tetraazacyclododecanine [for production, cf.: WO 97/02051], in 50 ml of dimethyl sulfoxide. After cooling to room temperature, the reaction solution is mixed with 3.27 g (15.84 mmol) of N,N'-dicyclohexylcarbodiimide, and it is stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off 3,000 Da), and in this case possible still present low-molecular components are removed at the same time. The retentate is then freeze-dried.

| Yield: 18.71 g (80.2% of theory) as a colorless lyophilizate. H₂O content (Karl-Fischer): 4.87%. Elementary analysis (relative to anhydrous substance): | | | | | | |
|---|---|---|---|---|---|---|
| Cld: | C 34.24 | H 3.83 | N 7.61 | F 21.92 | S 2.18 | Gd 10.67 |
| Fnd: | C 34.26 | H 3.79 | N 7.58 | F 21.87 | S 2.18 | Gd 10.68 |

EXAMPLE 24

1,7-Bis(benzyloxycarbonyl)-4-{3-oxa-pentane-1,5-dicarboxylic acid-1-oyl-5-[1-(4-perfluorooctylsulfonyl)-piperazine]-amide}-10-[2,6-N,N'-bis(1-O-α-D-carbonylmethyl-2,3,4,6-tetra-O-benzyl-mannopyranose)]-L-lysyl-1,4,7,10-tetraazacyclododecane 33.04 g (25.0 mmol) of the title compound of Example 18c), dissolved in 250 ml of tetrahydrofuran, is added to a solution that consists of 27.0 g (24.4 mmol) of the sec-amine, produced under Example 15a), in a mixture that consists of 150 ml of tetrahydrofuran and 15 ml of chloroform at 0° C. and under nitrogen atmosphere. Then, a total of 18.0 g (36.6 mmol) of EEDQ [2-ethoxy-1-ethoxycarbonyl-1,2-dihydroquinoline] is added in portions at 0° C. and allowed to stir overnight at room temperature. It is then evaporated to the dry state in a vacuum, and the remaining oil is chromatographed on silica gel (mobile solvent: n-hexane/isopropanol 25:1). 45.87 g (78.0% of theory, relative to the sec-amine that is used) of the title compound is obtained in the form of a colorless oil.

| Elementary analysis: | | | | | |
|---|---|---|---|---|---|
| Cld: | C 59.30 | H 5.39 | F 13.40 | N 4.65 | S 1.33 |
| Fnd: | C 59.32 | H 5.37 | F 13.37 | N 4.70 | S 1.34 | b) 1-{3-Oxa-pentane-1,5-dicarboxylic acid-1-oyl-5-[1-(4-perfluorooctylsulfonyl)-piperazine]-amide}-7-[2,6-N,N'-bis (1-O-α-D-carbonylmethyl-mannopyranose)]-L-lysyl-1,4,7,10-tetraazacyclododecane 24.1 g (10.0 mmol) of the title compound that is produced under Example 24a) is dissolved in 250 ml of ethanol and mixed with 1.4 g of Pearlman's catalyst (Pd 20%, C). It is hydrogenated until quantitative hydrogen uptake is reached, then catalyst is suctioned out, it is thoroughly rewashed with ethanol and evaporated to the dry state in a vacuum. The product is obtained as a yellowish-colored and extremely viscous oil.

| Yield: 12.80 g (90.1% of theory). Elementary analysis: | | | | | |
|---|---|---|---|---|---|
| Cld: | C 39.72 | H 4.89 | F 22.73 | N 7.88 | S 2.26 |
| Fnd: | C 39.72 | H 4.87 | F 22.77 | N 7.90 | S 2.24 | c) 1-{3-Oxa-pentane-1,5-dicarboxylic acid-1-oyl-5-[1-(4-perfluorooctylsulfonyl)-piperazine]-amide}-7-[2,6-N,N'-bis (1-O-α-D-carbonylmethyl-mannop-L-lysyl-4,10-bis[1,4,7-tris(carboxylatomethyl)-10-(3-aza-4-oxo-5-methyl-5-yl-pentanoyl)]-1,4,7,10-tetraazacyclododecane, digadolinium complex 5.54 g [8.8 mmol; 2.2 molar equivalents relative to the amine component of Example 24b) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and anhydrous lithium chloride (0.37 g, 8.8 mmol) are dissolved at 40° C. in 60 ml of absolute dimethyl sulfoxide while being stirred and mixed at this temperature with a total of 1.01 g (8.8 mmol) of N-hydroxysuccinimide and 5.68 g (4.0 mmol) of the title compound of Example 24b), dissolved in 40 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltra tion membrane (cut-off 3,000 Da), and low-molecular components are removed. The retentate is then freeze-dried.

Yield: 8.52 g (80.6% of theory; relative to the diamine component that is used) as a colorless lyophilizate.
H₂O content (Karl-Fischer): 6.09%.
Elementary analysis (relative to anhydrous substance):

| | | | | | | |
|---|---|---|---|---|---|---|
| Cld: | C 38.61 | H 4.76 | N 9.53 | F 12.21 | Gd 11.89 | S 1.12 |
| Fnd: | C 38.57 | H 4.82 | N 9.52 | F 12.21 | Gd 11.93 | S 1.15 |

EXAMPLE 25 a) 1,7-Bis(benzyloxycarbonyl)-4-{3-oxa-pentane-1, 5-dicarboxylic acid-1-oyl-5-[1-(4-perfluorooctylsulfonyl)-piperazine]-amide}-10-{2,6-N,N'-bis(1-O-α-D-(5-carbonyl)-pentyl-2,3,4,6-tetra-O-benzyl-mannopyranose)}-L-lysyl-1,4,7,10-tetraazacyclododecane 35.80 g (25.0 mmol) of the title compound of Example 17e), dissolved in 250 ml of tetrahydrofuran, is added at 0° C. and under nitrogen atmosphere to a solution that consists of 27.0 g (24.4 mmol) of the sec-amine, produced under Example 15a), in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C., and it is allowed to stir overnight at room temperature. It is then evaporated to the dry state in a vacuum, and the remaining oil is chromatographed on silica gel (mobile solvent: n-hexane/isopropanol 20:1). 49.48 g (80.4% of theory, relative to the sec-amine that is used) of the title compound is obtained in the form of a colorless oil.

Elementary analysis:

| | | | | | |
|---|---|---|---|---|---|
| Cld: | C 60.47 | H 5.79 | F 12.80 | N 4.44 | S 1.27 |
| Fnd: | C 60.52 | H 5.77 | F 12.77 | N 4.50 | S 1.30 | b) 1-{3-Oxa-pentane-1,5-dicarboxylic acid-1-oyl-5-[1-(4-perfluorooctylsulfonyl)-piperazine]-amide}-7-[2,6-N,N'-bis (1-O-α-D-(5-carbonyl)-pentyl-mannopyranose)]-L-lysyl-1,4,7,10-tetraazacyclododecane 25.2 g (10.0 mmol) of the title compound that is produced under Example 25a) is dissolved in 250 ml of ethanol and mixed with 1.8 g of Pearlman's catalyst (Pd 20%, C). It is hydrogenated until quantitative hydrogen uptake is reached, then catalyst is suctioned out, it is thoroughly rewashed with ethanol and evaporated to the dry state in a vacuum. The product is obtained as a yellow-colored and extremely viscous oil.

Yield: 14.11 g (92.5% of theory)
Elementary analysis:

| | | | | | |
|---|---|---|---|---|---|
| Cld: | C 49.60 | H 7.20 | F 21.17 | N 7.34 | S 2.10 |
| Fnd: | C 49.62 | H 7.17 | F 21.20 | N 7.30 | S 2.14 | c) 1-{3-Oxa-pentane-1,5-dicarboxylic acid-1-oyl-5-[1-(4-perfluorooctylsulfonyl)-piperazine]-amide}-7-[2,6-N,N'-bis (1-O-α-D-(5-carbonyl)-pentyl-mannopyranose)]-L-lysyl-4,10-bis[1,4,7-tris (carboxylatomethyl)-10-(3-aza-4-oxo-5-methyl-5-yl-pentanoyl)]-1,4,7,10-tetraazacyclododecane, digadolinium complex 5.54 g [8.8 mmol; 2.2 molar equivalents relative to the amine component of Example 25b) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and anhydrous lithium chloride (0.37 g, 8.8 mmol) are dissolved at 40° C. in 60 ml of absolute dimethyl sulfoxide while being stirred and mixed at this temperature with a total of 1.01 g (8.8 mmol) of N-hydroxysuccinimide and 6.10 g (4.0 mmol) of the title compound of Example 25b), dissolved in 40 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off 3,000 Da), and low-molecular components are removed. The retentate is then freeze-dried.

Yield: 9.26 g (84.0% of theory; relative to the diamine component that is used) as a colorless lyophilizate.
H₂O content (Karl-Fischer): 5.89%.
Elementary analysis (relative to anhydrous substance):

| | | | | | | |
|---|---|---|---|---|---|---|
| Cld: | C 40.52 | H 5.16 | N 9.15 | F 11.72 | Gd 11.41 | S 1.16 |
| Fnd: | C 40.57 | H 5.20 | N 9.12 | F 11.69 | Gd 11.43 | S 1.18 |

EXAMPLE 26 a) 6-N-t-Butyloxycarbonyl-2-N-benzyloxycarbonyl-L-lysine-[1-(4-perfluorooctylsulfonyl)-piperazine]-amide 19.02 g (50.0 mmol) of α-N-(benzyloxycarbonyl)-ξ-N'-(tertbutyloxycarbonyl)-L-lysine (commercially available from the Bachem Company) is dissolved in 150 ml of absolute tetrahydrofuran. 8.31 g (50.0 mmol) of carbonyldiimidazole and 5.03 g (50.0 mmol) of triethylamine, dissolved in 75 ml of dry tetrahydrofuran, are added drop by drop at 0° C., and stirring is allowed to continue for 10 minutes at this temperature. Then, a solution of 48.42 g (50.0 mmol) of perfluorooctylsulfonyl-piperazine and 5.03 g (50.0 mmol) of triethylamine in 250 ml of dry tetrahydrofuran is added in drops at 0° C. After stirring overnight, the tetrahydrofuran is drawn off in a vacuum, and the remaining oil is chromatographed on silica gel (mobile solvent: n-hexane/isopropanol 15:1). 49.48 g (80.4% of theory, relative to the sec-amine that is used) of the title compound is obtained in the form of a colorless oil.

Elementary analysis (relative to anhydrous substance):

| | | | | | |
|---|---|---|---|---|---|
| Cld: | C 40.01 | H 3.79 | N 6.02 | F 34.70 | S 3.45 |
| Fnd? | C 40.07 | H 3.82 | N 6.02 | F 34.67 | S 3.48 | b) 6-N-t-Butyloxycarbonyl-L-lysine-[1-(4-perfluorooctylsulfonyl)-piperazine]-amide 30.0 g (32.2 mmol) of the title compound of Example 26a) is dissolved in 300 ml of isopropanol and mixed with 1.5 g of Pearlman's catalyst (20% palladium hydroxide on carbon). It is hydrogenated for 10 hours at room temperature, whereby after the course of the reaction is checked by thin-layer chromatography, the hydrogenolytic cleavage of the benzyloxycarbonyl protective group is carried out quantitatively even after the above-mentioned reaction time. Catalyst is filtered out, and the filtrate is evaporated to the dry state in a vacuum. The remaining residue is chromatographed on silica gel (mobile solvent: n-hexane/isopropanol 25:1). 25.13 g (98.0% of theory) of the title compound is obtained in the form of a colorless oil.

| | Elementary analysis: | | | | |
|---|---|---|---|---|---|
| Cld: | C 34.68 | H 3.67 | F 40.55 | N 7.03 | S 4.03 |
| Fnd: | C 34.72 | H 3.70 | F 40.60 | N 7.01 | S 3.98 | c) 6-N-t-Butyloxycarbonyl-2-N-[1-S-α-D-(2-carbonyl)-ethyl-2,3,4,6-tetra-O-acetyl-mannopyranose]-L-lysine-[1-(4-perfluorooctylsulfonyl)-piperazine]-amide 15.53 g (35.60 mmol) of the 3-(2,3,4,6-tetra-O-acetyl-1-thio-α-D-mannopyranosyl)-propionic acid (production according to: J. Haensler et al., Bioconjugate Chem. 4, 85, (1993); Chipowsky, S. and Lee, Y. C. (1973), Synthesis of 1-Thio-aldosides; Carbohydrate Research 31, 339–346, and 3.60 g (35.60 mmol) of triethylamine are dissolved in 300 ml of dry tetrahydrofuran. After the reaction solution is cooled to −15° C. to −20° C., a solution of 4.92 g (35.60 mmol) of isobutyl chloroformate in 75 ml of dry tetrahydrofuran is slowly added in drops at this temperature while being stirred, whereby the rate of addition by drops can be selected in such a way that an internal temperature of −10° C. is not exceeded. After a reaction time of 15 minutes at −15° C., a solution of 28.35 g (35.60 mmol) of the title compound of Example 22b) and 3.60 g (35.60 mmol) of triethylamine, in 200 ml of dry tetrahydrofuran, is then slowly added in drops at 20° C.

After a reaction time of one hour at −15° C. and two hours at room temperature, the reaction solution is evaporated to the dry state in a vacuum. The remaining residue is taken up in 250 ml of ethyl acetate and washed twice with 100 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:25) as an eluant.

| Yield: 34.21 g (79.1% of theory) of the above-mentioned title compound as a colorless and strongly viscous oil. | | | | | |
|---|---|---|---|---|---|
| | Elementary analysis: | | | | |
| Cld: | C 39.54 | H 4.23 | N 4.61 | F 26.58 | S 5.28 |
| Fnd: | C 39.49 | H 4.21 | N 4.59 | F 26.52 | S 5.31 | d) 6-N-t-Butyloxycarbonyl-2-N-[1-S-α-D-(2-carbonyl)-ethyl-mannopyranose]-L-lysine-[1-(4-perfluorooctylsulfonyl)-piperazine]-amide 29.93 g (24.64 mmol) of the title compound of Example 26c) is suspended in 400 ml of absolute methanol and mixed at 5° C. with a catalytic amount of sodium methanolate. After a reaction time of 3 hours at room temperature, even thin-layer chromatographic checking (eluant: chloroform/methanol=9:1) of the course of the reaction indicates a quantitative reaction. For the purpose of working-up, the now clear reaction solution is neutralized by mixing with Amberlite(R) IR 120 (H+ form)-cation-exchange resin, exchanger is suctioned out, and the thus obtained methanolic filtrate is drawn off in a vacuum until a dry state is reached. The amorphous residue that is obtained is purified by chromatography on silica gel with use of 2-propanol/ethyl acetate/n-hexane (1:1:15) as an eluant.

| Yield: 23.42 g (90.8% of theory) of a colorless and viscous oil. | | | | | |
|---|---|---|---|---|---|
| | Elementary analysis: | | | | |
| Cld: | C 36.72 | H 4.14 | N 5.35 | F 30.85 | S 6.13 |
| Fnd: | C 36.69 | H 4.11 | N 5.35 | F 30.82 | S 6.11 | e) 2-N-[1-S-α-D-(2-Carbonyl)-ethyl-mannopyranose]-L-lysine-[1-(4-perfluorooctylsulfonyl)-piperazine]-amide 20.93 g (20.0 mmol) of the title compound of Example 26d) is dissolved in a mixture that consists of 50 ml of trifluoroacetic acid and 100 ml of dichloromethane at 0° C. while being stirred vigorously, and it is stirred for 10 minutes at this temperature. Then, it is evaporated to the dry state in a vacuum, and the residue is taken up in 150 ml of water. The pH of this aqueous product solution is set at 9.5 by adding 2 molar aqueous sodium hydroxide solution drop by drop. The aqueous product solution is desalinated with an AMICON(R) YM-3 ultrafiltration membrane (cut-off: 3,000 Da), and in this case possible, still present, low-molecular components are removed at the same time. The retentate is then freeze-dried.

| Yield: 17.79 g (94.2% of theory) of the free amine as a colorless lyophilizate. | | | | | |
|---|---|---|---|---|---|
| H₂O content (Karl-Fischer): 3.09%. | | | | | |
| Elementary analysis (relative to anhydrous substance): | | | | | |
| Cld: | C 34.26 | H 3.73 | N 5.92 | F 34.12 | S 6.77 |
| Fnd: | C 34.26 | H 3.79 | N 5.88 | F 34.07 | S 6.80 | f) 2-N-[1-S-α-D-(2-Carbonyl)-ethyl-mannopyranose]-6-N-[1,4,7-tris(carboxylatomethyl)-10-(3-aza-4-oxo-5-methyl-5-yl-pentanoyl)-1,4,7,10-tetraazacyclododecane]-L-lysine-[-(4-perfluorooctylsulfonyl)-piperazine]-amide, gadolinium complex 5.54 g [(8.8 mmol, 2.2 molar equivalents relative to the amine component of Example 26e) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g of anhydrous lithium chloride (8.8 mmol) are dissolved at 40° C. in 60 ml of absolute dimethyl sulfoxide while being stirred and mixed at this temperature with a total of 1.01 g (8.8 mmol) of N-hydroxysuccinimide and 3.78 g (4.0 mmol) of the title compound of Example 26e), dissolved in 40 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, taken up in water, insoluble dicyclohexylurea is filtered out, and the filtrate is desalinated with an AMICON[(R)] YM-3 ultrafiltration membrane (cut-off 3,000 Da), and low-molecular components are removed. The retentate is then freeze-dried.

Yield: 5.17 g (83.0% of theory) as a colorless lyophilizate.
$H_2O$ content (Karl-Fischer): 4.43%.
Elementary analysis (relative to anhydrous substance):

| | | | | | | |
|---|---|---|---|---|---|---|
| Cld: | C 35.45 | H 4.07 | N 8.09 | F 20.72 | Gd 10.09 | S 4.11 |
| Fnd: | C 35.50 | H 4.01 | N 8.12 | F 20.68 | Gd 10.13 | S 4.14 |

EXAMPLE 27 a) 6-N-Benzyloxycarbonyl-2-N-(1-O-β-D-carbonylmethyl-2,3,4,6-tetra-O-benzylglucopyranose)-L-lysine-[1-(4-perfluorooctylsulfonyl)-piperazine]-amide 8.02 g (13.4 mmol) of the title compound [1-carboxymethyloxy-2,3,4,6-tetra-O-benzyl-β-D-glucopyranoside] that is described in Patent Application DE 197 28 954 C1 under Example 46a) and 3.24 g (28.14 mmol) of N-hydroxysuccinimide are dissolved in 100 ml of dimethylformamide and mixed in portions at 0° C. with a total of 5.80 g (28.14 mmol) of N,N'-dicyclohexylcarbodiimide. It is stirred for 3 more hours at this temperature. A solution, cooled to 0° C., of 11.13 g (13.4 mmol) of the title compound of Example 1c), dissolved in 50 ml of dimethylformamide, is added in drops to the thus produced active ester solution, and it is stirred for 2 hours at 0° C. and for 12 hours at room temperature. For working-up, precipitated dicyclohexylurea is filtered out, and the solvent is then drawn off until a dry state is reached. The thus obtained residue is then chromatographed on silica gel (mobile solvent: dichloromethane/ethanol, 20:1; the chromatography was carried out with use of a solvent gradient with continuous increase of the ethanol content).

Yield: 12.67 g (67.0% of theory) of the title compound in the form of a colorless and strongly viscous oil.
Elementary analysis:

| | | | | | |
|---|---|---|---|---|---|
| Cld: | C 52.77 | H 4.50 | N 3.97 | F 22.89 | S 2.27 |
| Fnd: | C 52.75 | H 4.61 | N 3.98 | F 22.94 | S 2.26 | b) 2-N-(1-O-β-D-Carbonylmethyl-glucopyranose)-L-lysine-[1-(4-perfluorooctylsulfonyl)-piperazine]-amide 11.52 g (8.17 mmol) of the compound that is produced under 27a) is dissolved in 100 ml of ethanol, mixed with 0.5 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (three times with about 40 ml in each case) and evaporated to the dry state in a vacuum. The title compound is obtained as a strongly viscous and colorless oil.

Yield: 7.36 g (98.4% of theory).
Elementary analysis:

| | | | | | |
|---|---|---|---|---|---|
| Cld: | C 34.07 | H 3.63 | N 6.11 | F 35.24 | S 3.50 |
| Fnd: | C 34.11 | H 3.59 | N 6.08 | F 35.23 | S 3.52 | c) 2-N-(1-O-β-D-Carbonylmethyl-glucopyranose)-6-N-[1,4,7-tris (carboxylatomethyl)-10-(aza-4-oxo-5-methyl-5-yl-pentanoyl)-1,4,7,10-tetraazacyclododecane]-L-lysine-[1-(4-perfluorooctylsulfonyl)-piperazine]-amide, Gd complex 9.98 g [(15.84 mmol; 2.2 molar equivalents relative to the amine component of Example 27b) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.67 g (15.84 mmol) of anhydrous lithium chloride are dissolved at 40° C. in 80 ml of absolute dimethyl sulfoxide while being stirred and mixed at this temperature with a total of 1.82 g (15.84 mmol) of N-hydroxysuccinimide and 7.25 g (7.19 mmol) of the title compound of Example 27b), dissolved in 30 ml of absolute dimethyl sulfoxide. After cooling to room temperature, the reaction solution is mixed with 3.27 g (15.84 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, taken up in water, insoluble dicyclohexylurea is filtered out, the filtrate is desalinated with an AMICON[(R)] YM-3 ultrafiltration membrane (cut-off: 3,000 Da), and low-molecular components are removed. The retentate is then freeze-dried.

Yield: 9.11 g (83.0% of theory) as a colorless lyophilizate.
$H_2O$ content 4.02%.
(according to Karl-Fischer):
Elementary analysis (relative to anhydrous substance):

| | | | | | | |
|---|---|---|---|---|---|---|
| Cld: | C 35.37 | H 4.02 | N 8.25 | F 21.13 | S 2.10 | Gd 10.29 |
| Fnd: | C 35.42 | H 4.07 | N 8.18 | F 21.09 | S 2.06 | Gd 10.34 |

EXAMPLE 28 a) 2-N-Trifluoroacetyl-L-lysine-[1-(4-perfluorooctylsulfonyl)-piperazne]-amide 10.0 g (11.46 mmol) of the compound, produced under 1b), is dissolved in 100 ml of ethanol, mixed with 1.0 g of Pearlman's catalyst (Pd 20%/C) and hydrogenated until quantitative hydrogen uptake is reached. Catalyst is suctioned out, it is rewashed with ethanol and evaporated to the dry state in a vacuum. The title compound is obtained as a viscous and colorless oil.

| Yield: | 8.85 g (97.5% of theory). | | | | |
|---|---|---|---|---|---|
| | Elementary analysis: | | | | |
| Cld: | C 30.31 | H 2.54 | N 7.07 | F 47.95 | S 4.05 |
| Fnd: | C 30.36 | H 2.50 | N 7.11 | F 47.99 | S 4.00 | b) 2-N-Trifluoroacetyl-6-N-[1-O-α-D-(5-carbonyl)-pentyl-2,3,4,6-tetra-O-benzyl-mannopyranose]-L-lysine-[1-(4-perfluorooctylsulfonyl)-piperazine]-amide A solution of 27.51 g (36.6 mmol) of the title compound of Example 17c) in 150 ml of dimethylformamide is added in drops to a solution, cooled to 0° C., that consists of 29.0 g (36.6 mmol) of the title compound of Example 28a) and 4.05 g (40.26 mmol) of triethylamine in 100 ml of dimethylformamide. After the addition is completed, it is stirred for one more hour at 0° C. and then overnight at room temperature. It is evaporated to the dry state in a vacuum, and the residue is taken up in 300 ml of ethyl acetate. Insoluble components are filtered out, and the filtrate is washed twice with 100 ml each of 5 aqueous soda solution. The organic phase is dried on magnesium sulfate and evaporated to the dry state in a vacuum. The residue is chromatographed on silica gel (mobile solvent: n-hexane/isopropanol 25:1). 42.05 g (80.4% of theory) of the title compound is obtained in the form of a colorless oil.

| | Elementary analysis: | | | | |
|---|---|---|---|---|---|
| Cld: | C 50.42 | H 4.51 | N 7.96 | F 26.59 | S 2.24 |
| Fnd: | C 50.38 | H 4.50 | N 7.91 | F 26.62 | S 2.20 | c) 6-N-[1-O-α-D-(5-Carbonyl)-pentyl-2,3,4,6-tetra-O-benzyl-mannopyranose]-L-lysine-[1-(4-perfluorooctylsulfonyl)-piperazine]-amide 20.0 g (14.0 mmol) of the compound, produced under Example 28b), is dissolved in 150 ml of ethanol. The solution of 2.8 g (70.0 mmol) of sodium hydroxide in 25 ml of distilled water is then added to it, and it is stirred for 0.5 hour at 50° C. According to the thin-layer chromatogram, the protective group cleavage at this point has already taken place quantitatively. It is evaporated to the dry state in a vacuum, and traces of water are removed by repeated co-distillation with ethanol. The residue is chromatographed on silica gel (mobile solvent: n-hexane/isopropanol 20:1). 16.66 g (89.3% of theory) of the title compound is obtained in the form of a colorless oil.

| | Elementary analysis: | | | | |
|---|---|---|---|---|---|
| Cld: | C 52.25 | H 4.91 | N 4.20 | F 24.22 | S 2.41 |
| Fnd: | C 52.30 | H 4.90 | N 4.18 | F 24.22 | S 2.38 | d) 6-N-[1-O-α-D-(5-Carbonyl)-pentyl-mannopyranose]-L-lysine-[1-(4-perfluorooctylsulfonyl)-piperazine]-amide 15.0 g (11.25 mmol) of the compound, produced under 28c), is dissolved in 150 ml of a 10:1 mixture that consists of ethanol and water, and it is mixed with 1.0 g of Pearlman's catalyst (Pd 20%/C). Then, it is hydrogenated until quantitative hydrogen uptake is reached at room temperature and under one atmosphere of hydrogen pressure. Catalyst is suctioned out, it is rewashed with ethanol/water (10:1) and evaporated to the dry state in a vacuum. The title compound is obtained as a viscous and colorless oil.

| Yield: | 10.77 g (98.4% of theory). | | | | |
|---|---|---|---|---|---|
| | Elementary analysis: | | | | |
| Cld: | C 37.04 | H 4.25 | N 5.76 | F 33.20 | S 3.30 |
| Fnd: | C 37.06 | H 4.20 | N 5.18 | F 33.19 | S 3.30 | e) 6-N-[1-O-α-D-(5-Carbonyl)-pentyl-mannopyranose]-2-N-[1,4,7-tris(carboxylatomethyl)-10-(3-aza-4-oxo-5-methyl-5-yl-pentanoyl)-1,4,7,10-tetraazacyclododecane]-L-lysine-[1-(4-perfluorooctylsulfonyl)-piperazine]-amide, Gd complex 5.54 g [(8.8 mmol; 2.2 molar equivalents relative to the amine component of Example 28d) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g (8.8 mmol) of anhydrous lithium chloride are dissolved at 40° C. in 60 ml of absolute dimethyl sulfoxide while being stirred and mixed at this temperature with a total of 1.01 g (8.8 mmol) of N-hydroxysuccinimide and 3.89 g (4.0 mmol) of the title compound of Example 28d), dissolved in 60 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, taken up in water, insoluble dicyclohexylurea is filtered out, and the filtrate is desalinated with an AMICON(R) YM-3 ultrafiltration membrane (cut-off: 3,000 Da), and low-molecular components are removed. The retentate is then freeze-dried.

Yield: 4.81 g (75.9% of theory) as a colorless lyophilizate.
H₂O content 8.98%.
(Karl-Fischer):

| | Elementary analysis (relative to anhydrous substance): | | | | | |
|---|---|---|---|---|---|---|
| Cld: | C 37.15 | H 4.39 | N 7.96 | F 20.38 | Gd 9.92 | S 2.02 |
| Fnd: | C 37.27 | H 4.40 | N 8.02 | F 20.31 | Gd 10.00 | S 1.98 |

EXAMPLE 29 a) 1,7-Bis(benzyloxycarbonyl)-4-(1-O-β-D-carbonylmethyl-2,3,4,6-tetra-O-benzyl-galactopyranose)-10-{3-oxa-pentane-1,5-dicarboxylic acid-1-oyl-5-[1-(4-perfluorooctylsulfonyl)-piperazine]-amide }-1,4,7,10-tetraazacyclododecane 35.80 g (25.0 mmol) of the title compound of Example 17e), dissolved in 250 ml of tetrahydrofuran, is added to a solution that consists of 27.0 g (24.4 mmol) of the sec-amine, produced under Example 15a), in a mixture that consists of 150 ml of tetrahydrofuran and 15 ml of chloroform at 0° C. and under nitrogen atmosphere. Then, a total of 18.0 g (36.6 mmol) of EEDQ [2-ethoxy-1-ethoxycarbonyl-1,2-dihydroquinoline] is added in portions at 0° C. and allowed to stir overnight at room temperature. It is then evaporated to the dry state in a vacuum, and the remaining oil is chromatographed on silica gel (mobile solvent: n-hexane/isopropanol 20:1). 32.11 g (78.0% of theory, relative to the sec-amine that is used) of the title compound is obtained in the form of a colorless oil.

| Elementary analysis: | | | | | |
|---|---|---|---|---|---|
| Cld: | C 54.09 | H 4.72 | F 19.14 | N 4.93 | S 1.90 |
| Fnd: | C 54.12 | H 4.77 | F 19.17 | N 5.03 | S 1.90 | b) 1-(1-O-β-D-Carbonylmethyl-galactopyranose)-7-{3-oxa-pentane-1,5-dicarboxylic acid-1-oyl-5-[1-(4-perfluorooctylsulfonyl)-piperazine]-amide}-1,4,7,10-tetraazacyclododecane 30.0 g (17.77 mmol) of the title compound, produced under Example 29a), is dissolved in 250 ml of ethanol and mixed with 3.0 g of Pearlman's catalyst (Pd 20%/C). It is hydrogenated until quantitative hydrogen uptake is reached, catalyst is then suctioned out, it is thoroughly rewashed with ethanol and evaporated to the dry state in a vacuum. The product is obtained as a yellowish-colored and extremely viscous oil.

| Yield: | 17.89 g (95.1% of theory) | | | | |
|---|---|---|---|---|---|
| | Elementary analysis: | | | | |
| Cld: | C 36.30 | H 4.09 | F 30.50 | N 7.94 | S 3.03 |
| Fnd: | C 36.26 | H 4.12 | F 30.46 | N 7.90 | S 3.04 | c) 1-(1-O-β-D-Carbonylmethyl-galactopyranose)-7-{3-oxapentane-1,5-dicarboxylic acid-1-oyl-5-[1-(4-perfluorooctylsulfonyl)-piperazine]-amide}-4,10-bis[1,4,7-tris(carboxylatomethyl)-10-(3-aza-4-oxo-5-methyl-5-yl-pentanoyl)-1,4,7,10-tetraazacyclododecane ]-1,4,7,10-tetraazacyclododecane, digadolinium complex 5.54 g [8.8 mmol; 4.4 molar equivalents relative to the amine component of Example 29b) that is used] of the Gd complex, described in Patent Application DE 197 28 954 C1 under Example 31), of 10-(4-carboxy-1-methyl-2-oxo-3-azabutyl)-1,4,7,10-tetraazacyclododecane-1,4,7-triacetic acid and 0.37 g (8.8 mmol) of anhydrous lithium chloride are dissolved at 40° C. in 60 ml of absolute dimethyl sulfoxide while being stirred and mixed at this temperature with a total of 1.01 g (8.8 mmol) of N-hydroxysuccinimide and 2.11 g (2.0 mmol) of the title compound of Example 29b), dissolved in 25 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until precipitation of the above-mentioned title compound is completed, the precipitate is suctioned off, dried, taken up in water, insoluble dicyclohexylurea is filtered out, and the filtrate is desalinated with an AMICON(R) YM-3 ultrafiltration membrane (cut-off: 3,000 Da), and low-molecular components are removed. The retentate is then freeze-dried.

| Yield: | 3.29 g (72.2% of theory; relative to the amine component that is used) as a colorless lyophilizate. | | | | |
|---|---|---|---|---|---|
| H₂O content (Karl-Fischer): | 5.99%. | | | | |
| Elementary analysis (relative to anhydrous substance): | | | | | |
| Cld: | C 36.84 | H 4.37 | N 9.82 | F 14.15 | Gd 19.63 | S 1.40 |
| Fnd: | C 36.87 | H 4.40 | N 9.82 | F 14.09 | Gd 19.59 | S 1.38 |

EXAMPLE 30 a) 3-(1-O-α-D-2,3,4,6-Tetra-O-benzyl-mannopyranose)-2-N-benzyloxycarbonyl-L-serine-methyl ester 21.42 g (39.61 mmol) of 2,3,4,6-tetra-O-benzyl-α-D-mannopyranose (production according to: F. Kong et al., J. Carbohydr. Chem.; 16; 6; 1997; 877–890) is dissolved in 500 ml of dry acetonitrile. After the reaction solution is cooled to 5° C., a solution of 13.23 g (59.52 mmol) of trifluoromethanesulfonic acid-trimethyl silyl ester in 30 ml of acetonitrile, followed by a solution that consists of 20.06 g (79.21 mmol) of N-benzyloxycarbonyl-L-serine methyl ester (commercially available from the Bachem Company) in 50 ml of acetonitrile, are slowly added in drops at this temperature while being stirred, whereby the rate of addition by drops can be selected in such a way that an internal temperature of 10° C. is not exceeded. After a reaction time of 15 hours at room temperature, the reaction solution is evaporated to the dry state in a vacuum. The remaining residue is taken up in 250 ml of ethyl acetate and washed twice with 100 ml each of saturated sodium bicarbonate solution and once with 200 ml of water. After the organic phase is dried on sodium sulfate, salt is suctioned out, and the ethyl acetate is removed in a vacuum. The remaining oily residue is purified on silica gel with use of ethyl acetate/n-hexane (1:5) as an eluant.

| Yield: | 23.60 g (76.8% of theory) of the above-mentioned title compound as a colorless oil. | | |
|---|---|---|---|
| | Elementary analysis: | | |
| Cld: | C 71.21 | H 6.37 | N 1.81 |
| Fnd: | C 71.19 | H 6.41 | N 1.79 | b) 3-(1-O-α-D-2,3,4,6-Tetra-O-benzyl-mannopyranose)-2-N-benzyloxycarbonyl-L-serine 10.0 g (12.90 mmol) of the compound that is produced under Example 30a) is dissolved in a mixture that consists of 20 ml of methanol, 20 ml of water and 50 ml of tetrahydrofuran. 0.47 g (19.35 mmol) of lithium hydroxide, dissolved in 25 ml of distilled water, is then added at room temperature, and it is then stirred for 6 hours at 60° C. After the course of the reaction is checked by means of thin-layer chromatography (eluant: methylene chloride/methanol 10:1), the saponification of the methyl ester of Example 30a) has already taken place quantitatively after the above-mentioned reaction time. For the purpose of working-up, the product solution is evaporated to the dry state in a vacuum, and the remaining residue is taken up in 250 ml of ethyl acetate in the heat (about 60° C.) Then, the thus obtained ethyl acetate phase is washed twice with 50 ml each of a 15% aqueous hydrochloric acid, and once with 100 ml of distilled water. The organic phase is dried on magnesium sulfate, filtered and evaporated to the dry state in a vacuum. The residue is chromatographed on silica gel (mobile solvent: n-hexane/ethyl acetate 5:1). 8.40 g (85.7% of theory) of the title compound is obtained in the form of a colorless oil.

Elementary analysis:

| Cld: | C 70.94 | H 6.22 | N 1.84 |
|---|---|---|---|
| Fnd: | C 70.97 | H 6.30 | N 1.78 | c) 3-(1-O-α-D-2,3,4,6-Tetra-O-benzyl-mannopyranose-2-N-benzyloxycarbonyl-L-serine-[1-(4-perfluorooctylsulfonyl)-piperazine]-amide 20.57 g (27.0 mmol) of the carboxylic acid, produced according to Example 30b), dissolved in 50 ml of tetrahydrofuran, is added drop by drop to 13.86 g (24.40 mmol) of 1-perfluorooctylsulfonylpiperazine (produced according to DE 19603033), dissolved in a mixture that consists of 150 ml of tetrahydrofuran and 15 ml of chloroform at 0° C. and under nitrogen atmosphere. Then, a total of 18.0 g (36.60 mmol) of EEDQ [2-ethoxy-1-ethoxycarbonyl-1,2-dihydroquinoline] is added in portions at 0° C. and allowed to stir overnight at room temperature. For the purpose of working-up, the reaction solution is concentrated by evaporation in a vacuum, and the remaining, extremely viscous oil is chromatographed on silica gel with use of an n-hexane/isopropanol (15:1) mixture as an eluant system. 17.0 g (79.6% of theory, relative to the primary amine that is used) of the title compound is obtained in the form of a colorless and viscous oil.

Elementary analysis:

| Cld: | C 51.53 | H 4.23 | N 3.15 | F 25.65 | S 2.41 |
|---|---|---|---|---|---|
| Fnd: | C 51.48 | H 4.27 | N 3.10 | F 25.71 | S 2.35 | d) 3-(1-O-α-D-Mannopyranose)-L-serine-[1-(4-perfluorooctylsulfonyl)piperazine]-amide 15.0 g (11.41 mmol) of the compound, produced according to Example 30c), is dissolved in 200 ml of ethanol and mixed with 1.5 g of Pearlman's catalyst (Pd 20%, C). Then, the reaction solution is hydrogenated at room temperature under a hydrogen atmosphere (1 atm) until no more hydrogen absorption can be observed (about 8 hours). For the purpose of working-up, catalyst is suctioned out, it is thoroughly rewashed with ethanol (twice with about 100 ml each),and the product-containing ethanolic filtrate is evaporated to the dry state in a vacuum. The title compound is obtained as a strongly viscous and colorless oil.

Yield: 8.79 g (94.0% of theory).
Elementary analysis:

| Cld: | C 30.78 | H 3.20 | N 5.13 | F 39.41 | S 3.91 |
|---|---|---|---|---|---|
| Fnd: | C 30.87 | H 3.14 | N 5.19 | F 39.50 | S 3.88 | e) 3-(1-O-α-D-Mannopyranose)-2-N-[1,4,7-tris(carboxylatomethyl)-10-(3-aza-4-oxo-5-methyl-5-yl-pentanoyl)-1,4,7,10-tetraazacyclododecane]-L-serine-[1-(4-perfluorooctylsulfonyl)-piperazine]-amide, Gd complex A stirred suspension of 5.7 g [9.06 mmol; corresponding to 1.5 molar equivalents relative to the title compound (primary amine) of Example 30d) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid in 75 ml of absolute dimethyl sulfoxide is mixed at 70° C. with 0.68 g (15.9 mmol) of lithium chloride. After 30 minutes of stirring at 70° C., the now clear reaction solution is mixed in portions with a total of 1.83 g (15.9 mmol) of N-hydroyxsuccinimide, and the reaction mixture is held for 1 more hour at 70° C. After the reaction solution is cooled to 10° C., it is mixed with 4.52 g (23.85 mmol) of dicyclohexylcarbodiimide, and the reaction solution is stirred for another hour at 0° C., followed by 12 hours at 22° C. The thus obtained solution of N-hydroxysuccinimide ester of the Gd complex of 10-(4-carboxy-1-methyl-2-oxo-3-azabutyl)-1,4,7,10-tetraazacyclododecane-1,4,7-triacetic acid is now mixed drop by drop at 22° C. with a solution of 4.94 g (6.03 mmol) of the title compound of Example 30d), in 15 ml of absolute dimethyl sulfoxide, and it is stirred for another 12 hours at room temperature. For working-up, the reaction solution is slowly added in drops at 22° C. into a solvent mixture that consists of 250 ml of acetone and 250 ml of 2-propanol, whereby after 12 hours at 10° C., the title compound is deposited completely as a light yellowish-colored oil. The supernatant eluant mixture is carefully decanted out, and the oily product is taken up in 200 ml of distilled water, whereby the latter completely dissolves so that a light yellowish-colored aqueous solution of the above-mentioned title compound is obtained. The aqueous product solution is subsequently filtered first with a membrane filter and then, for the purpose of desalination and separation of low-molecular components, it is ultrafiltered three times with a YM3-ultrafiltration membrane (AMICON(R): cut-off: 3,000 Da). The thus obtained retentate is then freeze-dried.

Yield: 8.63 g (80.2% of theory, relative to the title compound of Example 30d) that is used) as a colorless lyophilizate with a water content of 7.65%.
Elementary analysis (relative to anhydrous substance):

| Cld: | C 33.57 | H 3.80 | N 7.83 | F 22.57 | Cd 10.99 | S 2.24 |
|---|---|---|---|---|---|---|
| Fnd: | C 33.57 | H 3.76 | N 7.82 | F 22.63 | Gd 11.06 | S 2.18 |

EXAMPLE 31 a) 6-N-Benzyloxycarbonyl-2-N-[-O-β-D-galactopyranosyl (1→4)-gluconosyl ]-L-lysine-[1-(4-perfluorooctylsulfonyl)-piperazine]-amide A solution of 13.3 g (37.2 mmol) of O-β-D-galactopyranosyl-(1→4)-D-glucono-1,5-lactone [lactobionolactone; production according to: (a) Williams, T. J.; Plessas, N. R., Goldstein, I. J. Carbohydr. Res. 1978, 67, Cl. (b) Kobayashi, K.; Sumitomo, H.; Ina, Y. Polym. J. 1985, 17, 567, (c) Hiromi Kitano, Katsuko Sohda, and Ayako Kosaka, Bioconjugate Chem. 1995, 6 131–134] in 40 ml of absolute dimethyl sulfoxide is added drop by drop to a stirred solution of 4.98 g (6.0 mmol) of the title compound of Example 1c) in 40 ml of absolute dimethyl sulfoxide at room temperature. The thus obtained reaction solution is then stirred for 14 hours at 40° C. For working-up, it is mixed at room temperature with 500 ml of absolute 2-propanol, and the colorless precipitate that is produced is suctioned off using a G4 frit and thoroughly rewashed with a total of 250 ml of absolute 2-propanol. The thus obtained solid is now dissolved in 300 ml of distilled water and ultrafiltered a total of three times with a YM3-ultrafiltration membrane (AMICON$^{(R)}$: cut-off: 3,000 Da). Both the excess lactobionolactone and possibly still present, low-molecular components of the desired product are separated by the ultrafiltration process that is repeated three times. The residue that remains in the ultrafiltration membrane is subsequently completely dissolved in 300 ml of distilled water and freeze-dried.

Yield: 6.51 g (92.7% of theory) as a colorless lyophilizate.
Water content: 10.03%.
Elementary analysis (relative to anhydrous substance:

| | | | | | |
|---|---|---|---|---|---|
| Cld: | C 38.98 | H 4.05 | N 4.79 | F 27.58 | S 2.74 |
| Fnd: | C 39.04 | H 4.09 | N 4.82 | F 27.61 | S 2.71 | b) 2-N-[O-β-D-Galactopyranosyl (1→4)-gluconosyl]-L-lysine-[1-(4-perfluorooctylsulfonyl)-piperazine]-amide 5.0 g (4.27 mmol) of the compound that is produced under 31a) is dissolved in 100 ml of ethanol, mixed with 0.5 g of Pearlman's catalyst (Pd 20%, C) and hydrogenated at 1 atmosphere of hydrogen pressure until quantitative hydrogen uptake is reached. Catalyst is suctioned out, it is rewashed with ethanol and evaporated to the dry state in a vacuum. The title compound is obtained as a colorless and viscous oil.

Yield: 4.36 g (98.5% of theory).
Elementary analysis:

| | | | | | |
|---|---|---|---|---|---|
| Cld: | C 34.76 | H 3.99 | N 5.40 | F 31.51 | S 3.09 |
| Fnd: | C 34.78 | H 4.04 | N 5.34 | F 31.51 | S 3.15 | c) 2-N-[O-β-D-Galactopyranosyl (1→4)-gluconosyl]-6-N-[1,4,7-tris (carboxylatomethyl)-10-(3-aza-4-oxo-5-methyl-5-yl-pentanoyl)-1,4,7,10-(tetraazacyclododecane]-L-lysine-[1-(4-perfluorooctylsulfonyl)-piperazine]-amide, Gd complex 5.54 g [(8.8 mmol; 2.2 molar equivalents relative to the amine component of Example 31b) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g (8.8 mmol) of anhydrous lithium chloride are dissolved at 40° C. in 60 ml of absolute dimethyl sulfoxide while being stirred and mixed at this temperature with a total of 1.01 g (8.8 mmol) of N-hydroxysuccinimide and 3.85 g (4.0 mmol) of the title compound of Example 31b), dissolved in 60 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone/2-propanol (1:1) until precipitation of the above-mentioned title compound is completed, and the precipitate is suctioned off. The thus obtained precipitate is subsequently taken up in 300 ml of water, and insoluble dicyclohexylurea is filtered out. The filtrate is ultrafiltered three times with an AMICON $^{(R)}$ YM-3 ultrafiltration membrane (cut-off: 3,000 Da). Both the excess Gd complex and possibly still present, low-moleuclar components are separated from the desired product by the ultrafiltration process that is performed three times. The residue that remains in the ultrafiltration membrane is subsequently completely dissolved in 500 ml of distilled water and freeze-dried.

Yield: 4.64 g (70.4% of theory) as a colorless lyophilizate.
H$_2$O content (Karl-Fischer): 10.08%.
Elementary analysis (relative to anhydrous substance):

| | | | | | | |
|---|---|---|---|---|---|---|
| Cld: | C 35.70 | H 4.22 | N 7.65 | F 19.59 | Gd 9.54 | S 1.95 |
| Fnd: | C 35.77 | H 4.17 | N 7.71 | F 19.61 | Gd 9.60 | S 1.99 |

EXAMPLE 32 a) 6-N-Benzyloxycarbonyl-2-N-(2,3,4,5-pentahydroxy-hexanoyl)L-lysine-[1-(4-perfluorooctylsulfonyl)-piperazine]-amide A solution that consists of 21.45 g (120.4 mol) of 5-gluconolactone in 50 ml of tetrahydrofuran is added in drops at 50° C. to a solution that consists of 100.0 g (120.4 mol) of the title compound of Example 1c), in 500 ml of dry tetrahydrofuran. It is stirred for 3 hours at 60° C. and then overnight at room temperature. It is evaporated to the dry state in a vacuum, and the residue is chromatographed on silica gel (mobile solvent: dichloromethane/ethanol=20:1).

Yield: 98.37 g (82% of theory) of a viscous oil.
Elementary analysis:

| | | | | | |
|---|---|---|---|---|---|
| Cld: | C 38.10 | H 3.70 | F 32.02 | N 5.55 | S 3.18 |
| Fnd: | C 38.22 | H 3.79 | F 32.02 | N 5.42 | S 3.29 | b) 2-N-(2,3,4,5-Pentahydroxy-hexanoyl)-L-lysine-[1-[(4-perfluorooctylsulfonyl)-piperazine]-amide 100.9 g (100.0 mmol) of the title compound of Example 32a) is dissolved in 2000 ml of ethanol, and 10.0 g of palladium catalyst (10% Pd/C) is added to it. It is hydrogenated for 12 hours at room temperature. Catalyst is filtered out, and the filtrate is evaporated to the dry state in a vacuum.

Yield: 87.46 g (quantitative) of a colorless solid.
Elementary analysis:

| | | | | | |
|---|---|---|---|---|---|
| Cld: | C 32.96 | H 3.57 | N 6.41 | S 3.67 | F 36.93 |
| Fnd: | C 32.91 | H 3.72 | N 6.34 | S 3.50 | F 36.78 | c) 6-N-[1,4,7-Tris(carboxylatomethyl)]-1,4,7,10-tetraazacyclododecane-10-N-(pentanoyl-3-aza-4-oxo-5-methyl-5-yl) ]-2-N-[1-O-α-D-carbonylmethyl-mannopyranose]-L-lysine-[1-(4-perfluorooctylsulfonyl)-piperazine]-amide, Gd complex 50.0 g (54.55 mmol) of the title compound of Example 1e), 6.28 g (54.55 mmol) of N-hydroxysuccinimide, 4.62 g (109.0 mo) of lithium chloride and 34.35 g (54.55 mol) of 1,4,7-tris (carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 75.9 g (91.0% of theory) of a colorless solid.
Water content: 8.6%.
Elementary analysis (relative to anhydrous substance):

| Cld: | C 35.34 | H 4.09 | N 8.24 | S 2.10 | F 21.12 | Gd 10.28 |
|---|---|---|---|---|---|---|
| Fnd: | C 35.28 | H 4.15 | N 8.19 | S 2.15 | F 21.03 | Gd 10.14 |

EXAMPLE 33 a) 6-N-Benzyloxycarbonyl-2-N-(2,3,4,5-pentahydroxy-hexanoyl)L-lysine-[1-(4-perfluorooctylsulfonyl)-piperazine]-amide A solution that consists of 21.45 g (120.4 mol) of 5-gluconolactone in 50 ml of tetrahydrofuran is added in drops at 50° C. to a solution that consists of 100.0 g (120.4 mmol) of the title compound of Example 1c), and 12.18 g (120.4 mmol) of triethylamine in 500 ml of dry tetrahydrofuran. It is stirred for 3 hours at 60° C. and then overnight at room temperature. 400 ml of 5% aqueous hydrochloric acid is then added to it, it is stirred for 5 minutes at room temperature, mixed with sodium chloride, the organic phase is separated, it is dried on magnesium sulfate, evaporated to the dry state in a vacuum, and the residue is chromatographed on silica gel (mobile solvent: dichloromethane/ethanol 20:1).

Yield: 100.97 g (82% of theory) of a viscous oil.
Elementary analysis:

| Cld: | C 37.58 | H 3.45 | F 31.58 | N 5.48 | S 3.14 |
|---|---|---|---|---|---|
| Fnd: | C 37.72 | H 3.59 | F 31.72 | N 5.42 | S 3.29 | b) 2-N-(2,3,4,5-Pentahydroxy-hexanoyl)-L-lysine-1-[(4-perfluorooctylsulfonyl)-piperazine]-amide 100.9 g (100.0 mmol) of the title compound of Example 32a) is dissolved in 2000 ml of ethanol, and 10.0 g of palladium catalyst (10% Pd/C) is added to it. It is hydrogenated for 12 hours at room temperature. Catalyst is filtered out, and the filtrate is evaporated to the dry state in a vacuum.

Yield: 87.46 g (quantitative) of a colorless solid.
Elementary analysis:

| Cld: | C 32.96 | H 3.57 | N 6.41 | S 3.67 | F 36.93 |
|---|---|---|---|---|---|
| Fnd: | C 32.91 | H 3.72 | N 6.34 | S 3.50 | F 36.78 | c) 6-N-[1,4,7-Tris(carboxylatomethyl)]-1,4,7,10-tetraazacyclododecane-10-N-(pentanoyl-3-aza-4-oxo-5-methyl-5-yl) ]-2-N-[1-O-α-D-carbonylmethyl-mannopyranose]-L-lysine-[1-(4-perfluorooctylsulfonyl)-piperazine]-amide, Gd complex 50.0 g (54.55 mmol) of the title compound of Example 1e), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 75.9 g (91.0% of theory) of a colorless solid.
Water content: 8.6%
Elementary analysis (relative to anhydrous substance):

| Cld: | C 35.34 | H 4.09 | N 8.24 | S 2.10 | F 21.12 | Gd 10.28 |
|---|---|---|---|---|---|---|
| Fnd: | C 35.28 | H 4.15 | N 8.19 | S 2.15 | F 21.03 | Gd 10.14 |

Under the conditions of Example 1f, mannose was replaced with glucose or galactose.

EXAMPLE 34 a) 6-N-Benzyloxycarbonyl-2-N-[1-O-α-D-carbonylmethyl-(2,3,4,6-tetra-O-benzyl glucopyranose]-L-lysine-[1-(4-perfluorooctylsulfonyl)-piperazine]-amide 41.27 g (200.0 mmol) of N,N-dicyclohexylcarbodiimide is added at 0° C. to a solution that consists of 100.0 g (120.4 mol) of the title compound of Example 1c), 72.1 g (120.4 mol) of 1-O-α-D-carboxymethyl-2,3,4,6-tetra-O-benzyl-glucopyranose and 13.86 g (120.4 mol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum and chromatographed on silica gel (mobile solvent: dichloromethane/ethanol=20:1).

Yield: 136.1 g (87% of theory) of a viscous oil.
Elementary analysis:

| Cld: | C 57.32 | H 4.89 | N 4.31 | F 24.86 | S 2.47 |
|---|---|---|---|---|---|
| Fnd: | C 57.48 | H 5.04 | N 4.20 | F 24.69 | S 2.38 | b) 2-N-[1-O-α-D-Carbonylmethylglucopyranose]-L-lysine-1-[(4-perfluorooctylsulfonyl)-piperazine]-amide 130.0 g (100.0 mmol) of the title compound of Example 34a) is dissolved in 2000 ml of ethanol, and 10.0 g of palladium catalyst (10% Pd/C) is added to it. It is hydrogenated for 12 hours at room temperature. Catalyst is filtered out, and the filtrate is evaporated to the dry state in a vacuum.

Yield: 91.7 g (quantitative) of a colorless solid.
Elementary analysis:

| Cld: | C 34.07 | H 3.63 | N 6.11 | S 3.50 | F 35.24 |
|---|---|---|---|---|---|
| Fnd: | C 33.92 | H 3.71 | N 6.02 | S 3.42 | F 35.33 | c) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-glucopyranose]-L-lysine-[1-(4-perfluorooctylsulfonyl)-piperazine]-amide, Gd complex 50.0 g (54.55 mmol) of the title compound of Example 34b), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone, and it is stirred for 10 minutes. The precipitated solid is filtered off and then purified by chromatography (RP-18 mobile solvent: gradient that consists of water/ethanol/acetonitrile).

Yield: 75.9 g (91.0% of theory) of a colorless solid.
Water content: 8.6%.
Elementary analysis (relative to anhydrous substance):

| Cld: | C 35.34 | H 4.09 | N 8.24 | S 2.10 | F 21.12 | Gd 10.28 |
|---|---|---|---|---|---|---|
| Fnd: | C 35.26 | H 4.18 | N 8.14 | S 2.158 | F 21.01 | Gd 10.13 |

EXAMPLE 35 a) 6-N-Benzyloxycarbonyl-2-N-[1-O-α-D-carbonylmethyl-(2,3,4,6-tetra-O-benzyl-galactopyranose]-L-lysine-[1-(4-perfluorooctylsulfonyl)-piperazine]-amide 20.64 g (100.0 mmol) of N,N-dicyclohexylcarbodiimide is added at 0° C. to a solution that consists of 50.0 g (60.2 mmol) of the title compound of Example 1c), 36.05 g (60.2 mmol) of 1-O-α-D-carboxymethyl-2,3,4,6-tetra-O-benzyl-galactopyranose and 6.93 g (60.2 mmol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum and chromatographed on silica gel (mobile solvent: dichloromethane/ethanol=20:1).

Yield: 68.1 g (87% of theory) of a viscous oil.
Elementary analysis:

| Cld: | C 57.32 | H 4.89 | N 4.31 | F 24.86 | S 2.47 |
|---|---|---|---|---|---|
| Fnd: | C 57.47 | H 5.05 | N 4.19 | F 24.72 | S 2.29 | b) 2-N-[1-O-α-D-Carbonylmethyl-galactopyranose]-L-lysine-1-[(4-perfluorooctylsulfonyl)-piperazine]-amide 65.0 g (50.0 mmol) of the title compound of Example 35a) is dissolved in 1000 ml of ethanol, and 5.0 g of palladium catalyst (10% Pd/C) is added to it. It is hydrogenated for 12 hours at room temperature. Catalyst is filtered out, and the filtrate is evaporated to the dry state in a vacuum.

Yield: 45.35 g (quantitative) of a colorless solid.
Elementary analysis:

| Cld: | C 34.07 | H 3.63 | N 6.11 | S 3.50 | F 35.24 |
|---|---|---|---|---|---|
| Fnd: | C 33.93 | H 3.74 | N 6.01 | S 3.39 | F 35.05 | c) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-galactopyranose]-L-lysine-[1-(4-perfluorooctylsulfonyl)-piperazine]-amide, Gd complex 50.0 g (54.55 mmol) of the title compound of Example 35b), 6.28 g (54.55 mmol) of N-hydroxysuccinimide, 4.62 g (109.0 mol) of lithium chloride and 34.35 g (54.55 mol) of 1,4,7-tris (carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 37.95 g (91.0% of theory) of a colorless solid.
Water content: 8.6%.
Elementary analysis (relative to anhydrous substance):

| Cld: | C 35.34 | H 4.09 | N 8.24 | S 2.10 | F 21.12 | Gd 10.28 |
|---|---|---|---|---|---|---|
| Fnd: | C 35.22 | H 4.17 | N 8.18 | S 2.19 | F 20.91 | Gd 10.12 |

EXAMPLE 36 a) N-Trifluoroacetyl-L-glutamic acid-mono-benzyl ester 100 g (421.5 mmol) of L-glutamic acid-mono-benzyl ester is dissolved in a mixture that consists of 1000 ml of trifluoroacetic acid ethyl ester/500 ml of ethanol, and it is stirred for 24 hours at room temperature. It is evaporated to the dry state, and the residue is crystallized from diisopropyl ether.

Yield: 140.47 g (96% of theory) of a colorless, crystalline powder.
Elementary analysis:

| Cld: | C 50.46 | H 4.23 | F 17.10 | N 4.20 |
|---|---|---|---|---|
| Fnd: | C 51.35 | H 4.18 | F 17.03 | N 4.28 | b) 2-N-Trifluoacetyl-L-glutamic acid-mono-benzyl ester-5-N-(methyl)-N-(2,3,4,5,6-pentahydroxyhexyl)-amide 8.25 g (40 mmol) of N,N-dicyclohexylcarbodiimide is added at 0° C. to a solution that consists of 24.9 g (24.08 mmol) of the title compound of Example 36a), 2×g (24.08 mmol) of N-methylglucamine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent dichloromethane/ethanol=20:1).

| Yield: | 109.40 g (89% of theory) of a viscous oil. |
| --- | --- |
| | Elementary analysis: |
| Cld: | C 51.43 H 5.51 F 13.56 N 6.66 |
| Fnd: | C 51.22 H 5.41 F 13.40 N 6.75 | c) N-Trifluoroacetyl-L-glutamic acid-N-(methyl)-N-(2,3,4,5,6-pentahydroxyhexyl)-amide 77.33 g (15.15 mmol) of the title compound of Example 36b is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

| Yield: | 43.0 g (quantitative) of a colorless solid. |
| --- | --- |
| | Elementary analysis: |
| Cld: | C 40.01 H 5.19 F 17.26 N 8.48 |
| Fnd: | C 39.84 H 5.13 F 17.09 N 8.68 | d) Trifluoroacetyl-L-glutamic acid-5-N-(methyl)-N-(2,3,4,5,6-pentahydroxyhexyl)-amide-[1-(4-perfluorooctylsulfonyl)-piperazine]-amidopiperazine]-amide 16.42 g (66.4 mmol) of EEDQ (2-ethoxy-1,2,-dihydroquinoline-1-carboxylic acid ethyl ester) is added at 0° C. to 10.96 g (33.2 mmcl) of the title compound of Example 36c and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum and chromatographed on silica gel (mobile solvent: dichloromethane/methanol=20:1).

| Yield: | 28.67 g (92% of theory) of a colorless solid. |
| --- | --- |
| | Elementary analysis: |
| Cld: | C 39.61 H 2.89 F 35.66 N 6.19 S 3.54 |
| Fnd: | C 39.68 H 2.74 F 35.81 N 6.13 S 3.40 | e) L-Glutamic acid-5-N-(methyl)-N-(2,3,4,5,6-pentahydroxyhexyl)-amide-[1-(4-perfluorooctylsulfonyl)-piperazine]-amide Ammonia gas is introduced at 0° C. for one hour into a solution that consists of 28.36 g (30.22 mmol) of the title compound of Example 36d in 200 ml of ethanol. It then is stirred for 4 hours at 0° C. It is evaporated to the dry state, and the residue is absorptively precipitated from water. The solid is filtered off and dried in a vacuum (50° C.)

| Yield: | 24.19 g (95% of theory) of an amorphous solid. |
| --- | --- |
| | Elementary analysis: |
| Cld: | C 41.12 H 2.89 F 35.66 N 6.19 S 3.54 |
| Fnd: | C 41.15 H 2.83 F 35.78 N 6.28 S 3.71 | f) N-[1,4,7-Tris(carboxylatomethyl)-1,4,7,10-tetraazacyclododecane-10-(pentanoyl-3-aza-4-oxo-5-methyl-5-yl)]-L-glutamic acid-5-N-(methyl)-N-(2,3,4,5,6-pentahydroxyhexyl)-amide-5-[1-(4-perfluorooctylsulfonyl)-piperazine]-amide, Gd complex 20.43 g (24.25 mmol) of the title compound of Example 36c, 2.79 g (24.25 mmol) of N-hydroxysuccinimide, 2.12 g (50 mmol) of lithium chloride and 15.27 g (24.25 mmol) of 1,4,7-tris(carboxylatomethyl )-10[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

| Yield: | 28.45 g (79% of theory) of a colorless solid. |
| --- | --- |
| Water content: | 11.0% |
| | Elementary analysis (relative to anhydrous substance): |
| Cld: | C 34.41 H 3.83 F 23.13 N 9.03 S 2.30 Gd 11.26 |
| Fnd: | C 34.34 H 3.98 F 23.29 N 9.19 S 2.15 Gd 11.07 |

EXAMPLE 37 a) 6-N-Benzyloxycarbonyl-2-N-[1-O-α-D-carbonylmethyl-(2,3,4-tri O benzyl-glucuronic acid benzyl ester]-L-lysine-[1-(4-perfluorooctylsulfonyl)-piperazine]-amide 41.27 g (200.0 mmol) of N,N-dicyclohexylcarbodiimide is added at 0° C. to a solution that consists of 100.0 g (120.4 mol) of the title compound of Example 1c), 73.77 g (120.4 mol) of 1-O-α-D-carboxymethyl-2,3,4-tri-O-benzyl-glucuronic acid benzyl ester and 13.86 g (120.4 mol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum and chromatographed on silica gel (mobile solvent: dichloromethane/ethanol=20:1).

| Yield: | 147.58 g (86% of theory) of a viscous oil. |
| --- | --- |
| | Elementary analysis: |
| Cld: | C 52.25 H 4.31 N 3.93 F 22.66 S 2.45 |
| Fnd: | C 52.38 H 4.17 N 4.12 F 22.78 S 2.39 | b) 2-N-[1-O-α-D-Carbonylmethyl-glucuronic acid]-L-lysine-1-[(4-perfluorooctylsulfonyl)-piperazine]-amide 142.52 g (100.0 mmol) of the title compound of Example 37a) is dissolved in 2000 ml of ethanol, and 10.0 g of palladium catalyst (10% Pd/C) is added to it. It is hydrogenated for 12 hours at room temperature. Catalyst is filtered out, and the filtrate is evaporated to the dry state in a vacuum.

| Yield: | 93.06 g (quantitative) off a colorless solid. Elementary analysis: |
|---|---|
| Cld: | C 33.56 H 3.36 N 6.02 S 3.45 F 34.71 |
| Fnd: | C 33.31 H 3.42 N 6.04 S 3.40 F 35.51 | c) 6-N-[1,4,7-Tris(carboxylatomethyl)]-1,4,7,10-tetraazacyclododecane-10-N-(pentanoyl-3-aza-4-oxo-5-methyl-5-yl) ]-2-N-[1-O-α-D-carbonylmethyl-glucuronic acid]-L-lysine-[1-(4-perfluorooctylsulfonyl)-piperazine]-amide, Gd complex, sodium salt 50.76 g (54.55 mmol) of the title compound of Example 37b), 6.28 g (54.55 mmol) of N-hydroxysuccinimide, 4.62 g (109.0 mol) of lithium chloride and 34.35 g (54.55 mol) of 1,4,7-tris (carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

| Yield: | 75.149 g (88.0% of theory) of a colorless solid. |
|---|---|
| Water content: | 8.6%. |
| | Elementary analysis (relative to anhydrous substance): |
| Cld: | C 34.53 H 3.80 N 8.05 Na 1.47 S 2.05 F 20.63 Gd 10.05 |
| Fnd: | C 34.38 H 3.95 N 8.19 Na 1.63 S 2.15 F 20.83 Gd 10.14 |

EXAMPLE 38 a) 6-N-Benzyloxycarbonyl)-2-[2-(N-ethyl-N-perfluorooctylsulfonyl ]-amino]-acetyl-L-lysine 49.46 g (200.0 mmol) of EEDQ (2-ethoxy-1,2-dihydroquinoline-1-carboxylic acid ethyl ester) is added at 0° C. to 31.820 g (113.5 mmol) of 6-N-benzyloxycarbonyl)-L-lysine and 66.42 g (113.5 mmol) of 2-(N-ethyl-N-perfluorooctylsulfonyl)-aminoacetic acid (produced according to DE 196 03 033) in 300 ml of tetrahydrofuran), and it is stirred overnight at room temperature. It is evaporated to the dry state in a vacuum and chromatographed on silica gel (mobile solvent: dichloromethane/methanol=20:1).

| Yield: | 55.79 g (58% of theory) of a colorless solid. Elementary analysis: |
|---|---|
| Cld: | C 36.85 H 3.09 N 4.96 F 38.11 S 3.78 |
| Fnd: | C 36.85 H 3.19 N 4.87 F 38.28 S 3.95 | b) 6-N-Benzyloxycarbonyl-2-N-[2-(N-ethyl-N-perfluorooctylsulfonyl)-amino]-acetyl-L-lysine-N-methyl-N-(2,3,4,5,6-pentahydroxy-hexyl)-amide 20.64 g (100.0 mmol) of N,N-dicyclohexylcarbodiimide is added at 0° C. to a solution that consists of 51.02 g (60.2 mol) of the title compound of Example 38a), 11.75 g (60.2 mol) of N-methyl-glucamine and 6.93 g (60.2 mol) of N-hydroxysuccinimide, dissolved in 250 ml of dimethylformamide. It is stirred for 3 hours at 0° C. and then overnight at room temperature. Precipitated urea is filtered out, the filtrate is evaporated to the dry state in a vacuum, and it is chromatographed on silica gel (mobile solvent: dichloromethane/ethanol=20:1).

| Yield: | 53.05 g (86% of theory) of a viscous oil. Elementary analysis: |
|---|---|
| Cld: | C 38.68 H 4.03 N 5.47 F 31.52 S 3.13 |
| Fnd: | C 38.49 H 4.17 N 5.32 F 31.70 S 3.29 | c) 2-N-[2-(N-Ethyl-N-perfluorooctylsulfonyl)-amino]-acetyl-L-lysine-N-methyl-N-(2,3,4,5,6-pentahydroxy-hexyl)-amide 102.48 g (100.0 mmol) of the title compound of Example 38b) is dissolved in 2000 ml of ethanol, and 10.0 g of palladium catalyst (10% Pd/C) is added to it. It is hydrogenated for 12 hours at room temperature. Catalyst is filtered out, and the filtrate is evaporated to the dry state in a vacuum.

Yield: 89.06 g (quantitative) of a colorless solid
Elementary analysis:

| Cld: | C 33.72 | H 3.96 | N 6.29 | S 3.60 | F 36.26 |
|---|---|---|---|---|---|
| Fnd: | C 33.91 | H 3.82 | N 6.14 | S 3.47 | F 36.31 | d) 6-N-[1,4,7-Tris(carboxylatomethyl)]-1,4,7,10-tetraazacyclododecane-10-N-(pentanoyl-3-aza-4-oxo-5-methyl-5-yl)]-2-N-[2-(N-ethyl-N-perfluorooctylsulfonyl)-amino ]-acetyl-L-lysine-N-methyl-N-(2,3,4,5,6-pentahydroxy-hexyl)-amide, Gd complex 48.58 g (54.55 mmol) of the title compound of Example 38c), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 73.27 g (89.4% of theory) of a colorless solid.
Water content: 8.6%.
Elementary analysis (relative to anhydrous substance):

| Cld: | C 35.18 | H 4.23 | N 4.23 | S 2.13 | F 21.50 | Gd 10.47 |
|---|---|---|---|---|---|---|
| Fnd: | C 35.28 | H 4.15 | N 4.19 | S 2.18 | F 21.33 | Gd 10.61 |

EXAMPLE 39

Organ Distribution (Including Tumor and Lymph Node Concentration) After Intravenous Administration of the Contrast Medium According to the Invention of Example 1 in Prostate-cancer-carrying Rats After intravenous administration of 225 μmol of total gadolinium/kg of body weight of the title compound of Example 1 in rats (Cop-inbreeding Dunning R3327 MAT-Lu prostate cancer i.m.-implanted 12 days earlier), the metal content in various organs, in tumors and in lymph nodes (pooled as mesenteral and peripheral lymph nodes) was determined 10 minutes, 1 and 24 hours after administration (MW±SD, n=3).

| | Title Compound of Example 1 | | | | | |
|---|---|---|---|---|---|---|
| | Gd-Concentration [μmol/l] | | | % Dose per Total Tissue | | |
| | 10 min p.i. | 1 h p.i. | 24 h p.i. | 10 min p.i. | 1 h p.i. | 24 h p.i. |
| Liver | 387 ± 26 | 364 ± 8 | 746 ± 34 | 5.46 ± 0.16 | 5.81 ± 0.16 | 11.65 ± 0.97 |
| Spleen | 548 ± 22 | 487 ± 25 | 645 ± 27 | 0.39 ± 0.03 | 0.39 ± 0.02 | 0.57 ± 0.03 |
| Pancreas | 229 ± 27 | 199 ± 30 | 130 ± 13 | 0.26 ± 0.05 | 0.21 ± 0.05 | 0.17 ± 0.02 |
| Kidney | 2081 ± 537 | 883 ± 94 | 1178 ± 139 | 5.02 ± 1.29 | 2.15 ± 0.23 | 2.97 ± 0.21 |
| Lung | 837 ± 32 | 658 ± 29 | 370 ± 34 | 1.69 ± 0.06 | 1.38 ± 0.08 | 0.73 ± 0.04 |
| Heart | 438 ± 29 | 289 ± 24 | 131 ± 9 | 0.46 ± 0.01 | 0.31 ± 0.03 | 0.14 ± 0.02 |
| Brain | 47 ± 13 | 26 ± 5 | 14 ± 2 | 0.15 ± 0.03 | 0.08 ± 0.02 | 0.04 ± 0.00 |
| Muscle** | 99 ± 5 | 78 ± 1 | 36 ± 1 | 10.11 ± 0.03 | 0.09 ± 0.03 | 0.04 ± 0.00 |
| Tumor | 185 ± 36 | 184 ± 13 | 199 ± 19 | 0.28 ± 0.10 | 0.21 ± 0.02 | 0.31 ± 0.01 |
| Femur | 184 ± 4 | 127 ± 9 | 87 ± 6 | 0.65 ± 0.01 | 0.46 ± 0.03 | 0.31 ± 0.03 |
| mes. LK | 359 ± 72 | 697 ± 42 | 854 ± 135 | 0.11 ± 0.04 | 0.24 ± 0.02 | 0.32 ± 0.04 |
| periph. LK | 229 ± 15 | 436 ± 44 | 373 ± 24 | 0.10 ± 0.01 | 0.20 ± 0.03 | 0.18 ± 0.01 |
| Stomach (emptied) | 231 ± 10 | 219 ± 46 | 138 ± 9 | 0.57 ± 0.04 | 0.54 ± 0.12 | 0.37 ± 0.06 |
| Intestine (emptied) | 342 ± 16 | 409 ± 67 | 243 ± 22 | 2.91 ± 0.18 | 3.41 ± 1.02 | 2.14 ± 0.14 |
| Blood* | 1665 ± 110 | 825 ± 67 | 214 ± 9 | 42.95 ± 2.59 | 21.47 ± 1.78 | 1.78 ± 0.03 |
| Remainder of body**** | — ± — | — ± — | 225 ± 31 | — ± — | — ± — | 30.83 ± 4.05 |
| Urine 0–24 h | — ± — | — ± — | 94 ± 20 | — ± — | — ± — | 20.20 ± 4.41 |
| Feces 0–24 h | — ± — | — ± — | 3128 ± 204 | — ± — | — ± — | 21.85 ± 1.46 |
| Sum of Organs | | | | 60.47 ± 3.68 | 36.33 ± 2.51 | 52.01 ± 5.22 |
| Balance | | | | — ± — | — ± — | 94.1 ± 6.41 |

*58 ml of blood/kg of body weight
**only tissue sample from right lower leg muscle
***the sum total of all of the organs at 10 and 60 min. p. i., less tye remainder of the body
****the remainder of the body also contains the remainder of the blood

EXAMPLE 40

Lymph Node Visualization (MRT) After Intravenous Administration of the Contrast Medium According to the Invention of Example 1 in VX2-tumor-carrying Rabbits MR images were prepared of iliac lymph nodes pre-contrast and up to 24 hours after intravenous administration of 200 μmol of Gd/kg of body weight of the title compound of Example 1 in rabbits with VX2-tumors implanted i.m. The $T_1$-weighted gradient-echo images (1.5 T; sequence: MPRange; TR 11.1 ms, TE 4.3 ms, α 15°) illustrated the strong signal rise in healthy lymph node tissue. A zone without a signal rise within the lymph node was diagnosed as metastasis and confirmed histologically (H/E-staining of the lymph node section). Later (24 hours) after contrast medium administration, however, a signal reversal was observed, surprisingly enough. The signal rise in the healthy lymph node tissue was reduced, while the metastasis now exhibited a considerable signal rise. As early as immediately after administration, surprisingly enough, a considerable enhancement of the primary tumor (especially the periphery) was observed. Later (24 hours p.i.), this enhancement also propagates out from the center of the tumor.

EXAMPLE 41

Infarction Visualization (MRT) After Intravenous Administration of the Contrast Medium According to the Invention of Example 1 in Rats MR images were prepared of the heart (in vivo and post mortem) 24 hours after intravenous administration of 100 μmol of Gd/kg of body weight of the title compound of Example 1 in rats with acute induced myocardial infarction. The $T_1$-weighted spin-echo images (1.5 T; TR: 400 ms, TE: 6 ms; NA: 4; Matrix: 128*128; layer thickness: 2.5 mm) illustrated the strong signal rise in the infarction area. The successful indication of an acute myocardial infarction was confirmed using NBT staining.

What is claimed is:

1. Perfluoroalkyl-containing metal complexes with sugar radicals of formula I

in which
R is a monosaccharide or oligosaccharide radical that is bonded via the 1-OH position or 1-SH position,
$R_f$ is a perfluorinated, straight-chain or branched carbon chain with the formula —$C_nF_{2n}$E, in which E is a terminal fluorine, chlorine, bromine, iodine or hydrogen atom, and n is a number from 4–30, K is a metal complex of formula II

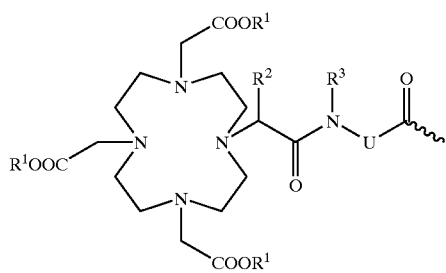

(II)

in which

R$^1$ is a hydrogen atom or a metal ion equivalent of atomic numbers 21–29, 31–33, 37–39, 42–44, 49 or 57–83, provided that at least two R$^1$ are metal ion equivalents, R$^2$ and R$^3$, independently of one another, are hydrogen, C$_1$–C$_7$ alkyl, benzyl, phenyl, —CH$_2$OH or —CH$_2$OCH$_3$, and U is —C$_6$H$_4$—O—CH$_2$-ω-, —(CH$_2$)$_{1-5}$-ω, a phenylene group, —CH$_2$—NHCO—CH$_2$—CH(CH$_2$COOH)—C$_6$H$_4$-ω-, —C$_6$H$_4$—(OCH$_2$CH$_2$)$_{0-1}$—N(CH$_2$COOH)—CH$_2$-ω or a C$_1$–C$_{12}$ alkylene group or a C$_7$–C$_{12}$–C$_6$H$_4$—O group that is optionally interrupted by one or more oxygen atoms, 1 to 3 —NHCO groups or 1- to 3 —CONH groups and/or is substituted with 1 to 3 —(CH$_2$)$_{0-5}$COOH groups, whereby ω stands for the binding site to —CO—, or of formula III

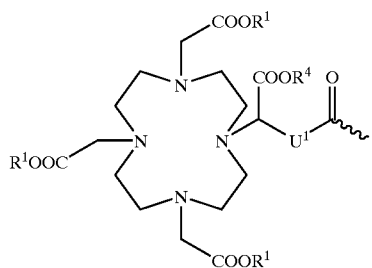

(III)

in which R$^1$ has the above-mentioned meaning, R$^4$ is hydrogen or a metal ion equivalent that is mentioned under R$^1$, and U$^1$ is —C$_6$H$_4$—O—CH$_2$-ω-, whereby ω means the binding site to —CO— or of formula IV

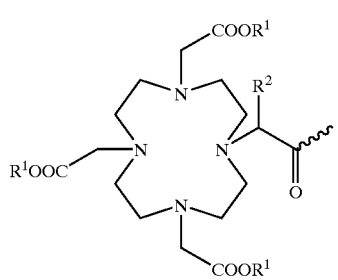

(IV)

in which R$^1$ and R$^2$ have the above-mentioned meaning or of formula V A or V B

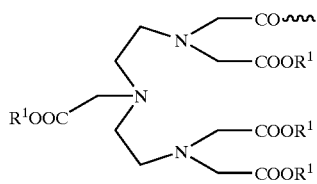

(VA)

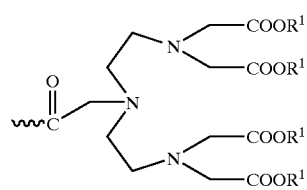

(VB)

in which R$^1$ has the above-mentioned meaning, or of formula VI

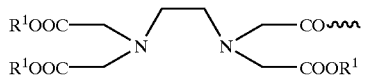

(VI)

in which R$^1$ has the above-mentioned meaning, or of formula VII

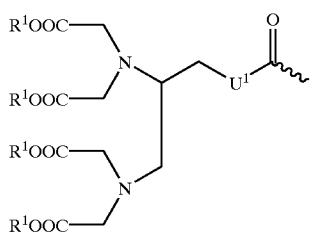

(VII)

in which R$^1$ has the above-mentioned meaning, and

U$^1$ is —C$_6$H$_4$—O—CH$_2$-ω-, whereby ω means the binding site to —CO—, or of formula VIII

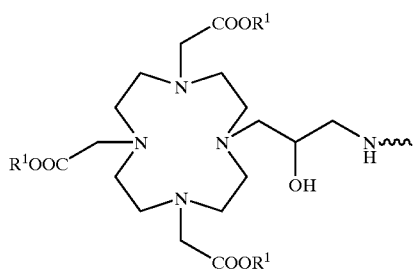

(VIII)

in which R$^1$ the above-mentioned meaning, and in radical K, optionally present free acid groups optionally can be present as salts of organic and/or inorganic bases or amino acids or amino acid amides, G for the case that K means metal complexes II to VII, is a radical that is functionalized in at least three places and that is selected from radicals a) to j) below (a) 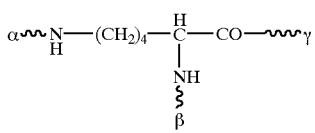

(b) 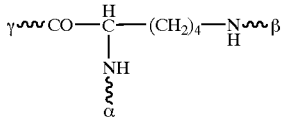

(c) 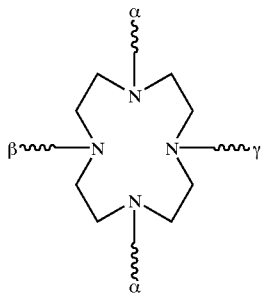

(d) 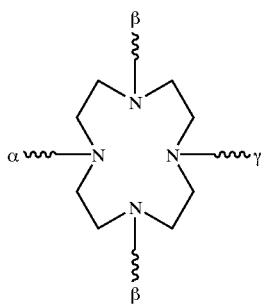

(e) 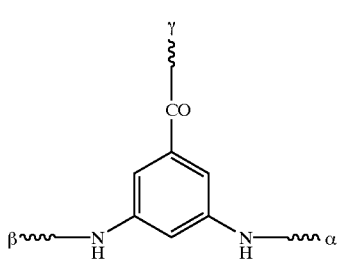

(f) 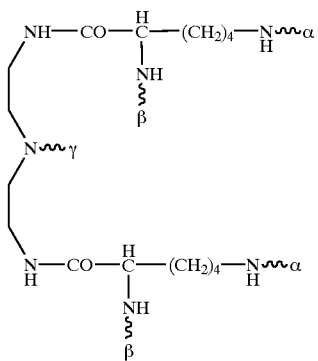

-continued (g) 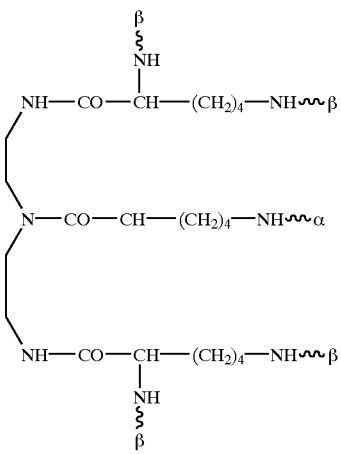

(h) 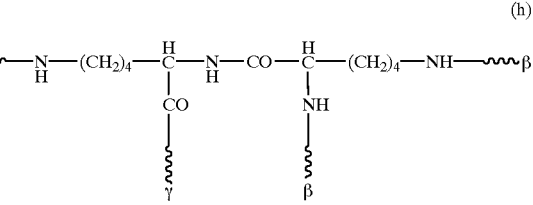

(i) 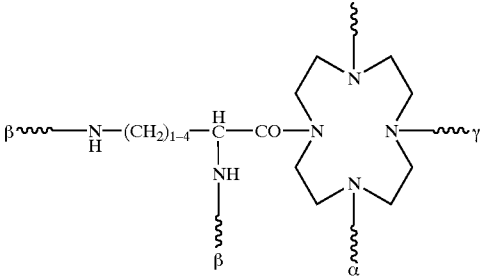

(j) 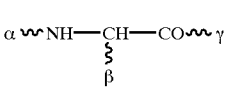

and

G for the case that K means metal complex VIII, is a radical that is functionalized in at least three places and that is selected from k) or l), (k) 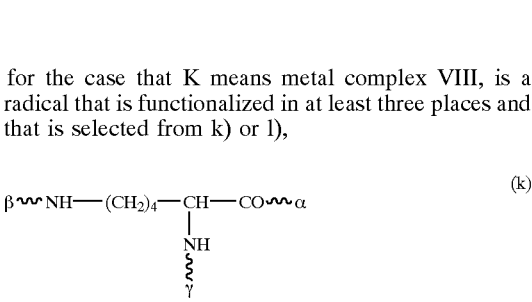

(l) 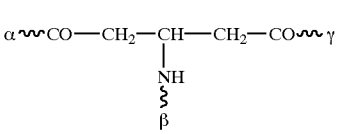

whereby α is the binding site of G to complex K, β is the binding site of G to radical Y and γ is the binding site of G to radical Z, Y is —CH$_2$, δ-(CH$_2$)$_n$CO-β (whereby n=1–5), δ-CH$_2$—CHOH—CO-β or δ-CH(CHOH—CH$_2$OH)—CHOH—CHOH—CO-β, whereby δ is the binding site to sugar radical R and β is the binding site to radical G, Z stands for

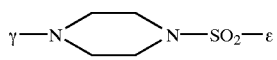

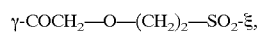

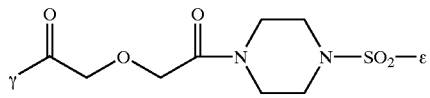

or

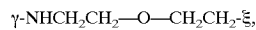

whereby γ is the binding site of Z to radical G, and ξ is the binding site of Z to perfluorinated radical $R_f$,
and
 1 and m, independently of one another, are the whole numbers 1 or 2,
and
 p is a whole number 1 to 4.

2. A metal complex according to claim 1, wherein metal ion equivalent $R^1$ is an element of atomic numbers 21–29, 39, 42, 44 or 57–83.

3. A metal complex according to claim 1, wherein metal ion equivalent $R^1$ is an element of atomic numbers 27, 29, 31–33, 37–39, 43, 49, 62, 64, 70, 75 or 77.

4. A metal complex according to claim 1, wherein R is a monosaccharide radical with 5 to 6 C atoms or its deoxy compound.

5. A metal complex according to claim 1, wherein K is a metal complex of formula II.

6. A metal complex according to claim 5, wherein $R^2$ and $R^3$, independently of one another, are hydrogen or $C_1$–$C_4$ alkyl.

7. A metal complex according to claim 1, wherein E in formula $—C_nF_{2n}E$ is a fluorine atom.

8. A metal complex according to claim 1, wherein G in formula I is a lysine radical (a) or (b).

9. A metal complex according to claim 1, wherein Z in formula I is

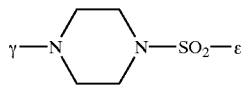

whereby γ is the binding site of Z to radical G, and ξ is the binding site of Z to perfluorinated radical $R_f$.

10. A metal complex according to claim 1, wherein in formula I, Y is δ-$(CH_2)_n$CO-β, whereby δ is the binding site to sugar radical R and β is the binding site to radical G.

11. A metal complex according to claim 1, wherein U in metal complex K is —$CH_2$— or —$C_6H_4$—O—$CH_2$-ω, whereby ω is the binding site to —CO—.

12. A method for the production of contrast media for use in NMR diagnosis and x-ray diagnosis comprising formulating a metal complex according to claim 2 in a physiologically administrable form for NMR diagnosis and x-ray diagnosis.

13. A method for the production of contrast media for infarction and necrosis imaging comprising formulating a metal complex according to claim 12 in a physiologically administrable form for infarction and necrosis imaging.

14. A method for the production of contrast media for use in radiodiagnosis and radiotherapy comprising formulating a metal complex according to claim 12 in a physiologically administrable form for radiodiagnosis and radiotherapy.

15. A method for the production of contrast media for lymphography in the diagnosis of changes in the lymphatic system comprising formulating a metal complex according to claim 2 in a physiologically administrable form for lymphography.

16. A method for the production of contrast media for use in indirect lymphography comprising formulating a metal complex according to claim 2 in a physiologically administrable form for indirect lymphography.

17. A method for the production of contrast media for use in intravenous lymphography comprising formulating a metal complex according to claim 2 in a physiologically administrable form for intravenous lymphography.

18. A method for the production of contrast media for visualizing the vascular space comprising formulating a metal complex according to claim 2 in a physiologically administrable form suitable for visualizing the vascular space.

19. A method for the production of contrast media for tumor imaging comprising formulating a metal complex according to claim 2 in a physiologically administrable form suitable for tumor imaging.

20. A method for the production of contrast media for the study of abnormal capillary permeability comprising formulating a metal complex according to claim 2 in a physiologically administrable form suitable for the study of abnormal capillary permeability.

21. Pharmaceutical composition that contains at least one physiologically compatible compound according to claim 1, optionally with the additives that are commonly used in galenicals.

22. Process for the production of perfluoroalkyl-containing complexes with sugar radicals of formula I

with K being a metal complex of one of formulas II to VII according to claim 1, G being a radical a) to j) according to claim 1, and Y,
 Z, R, $R_f$, m, p and l as defined in claim 1, which comprises reacting a carboxylic acid of formula IIa

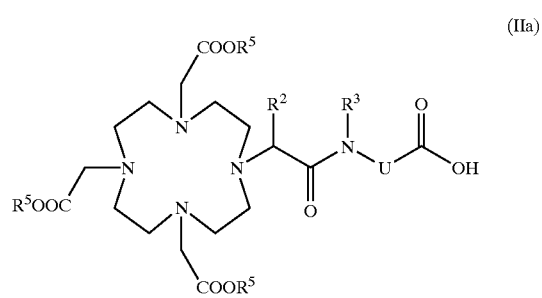

in which $R^5$ is a metal ion equivalent of atomic numbers 21–29, 31–33, 37–39, 42–44, 49 or 57–83 or a carboxyl protective group, and $R^2$, $R^3$ and U have the above-mentioned meaning, or a carboxylic acid of general formula IIIa

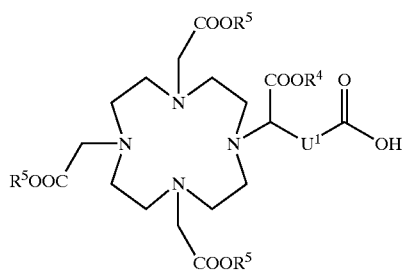

(IIIa)

in which $R^4$, $R^5$, and $U^1$ have the above-mentioned meaning or a carboxylic acid of formula IVa

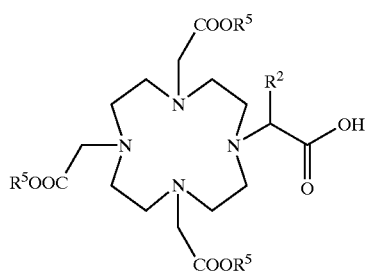

(IVa)

in which $R^5$ and $R^2$ have the above-mentioned meaning or a carboxylic acid of formula Va or Vb

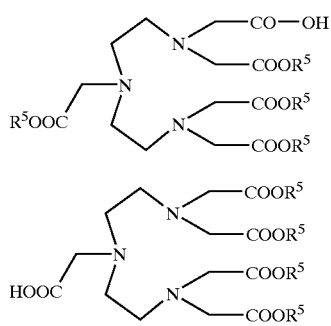

(Va)

(Vb)

in which $R^5$ has the above-mentioned meaning or a carboxylic acid of formula VIa

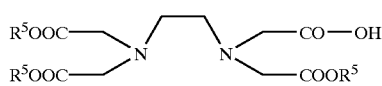

(VIa)

in which $R^5$ has the above-mentioned meaning or a carboxylic acid of formula VIIa

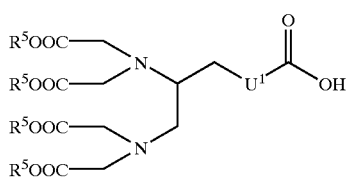

(VIIa)

in which $R^5$ and $U^1$ have the above-mentioned meanings, in optionally activated form with an amine of formula IX

(IX)

in which G, R, $R_f$, Y, Z, m and p have the meaning indicated in the claim, in a coupling reaction, and optionally subsequently cleaving optionally present protective groups to provide a metal complex of formula I, or if $R^5$ has the meaning of a protective group, reacting after cleavage of these protective groups in a subsequent step with at least one metal oxide or metal salt of an element of atomic numbers 21–29, 31–33, 37–39, 42–44, 49 or 57–83, and then, optionally, optionally present, acidic hydrogen atoms are substituted by cations of inorganic and/or organic bases, amino acids or amino acid amides.

23. Process for the production of perfluoroalkyl-containing metal complexes with sugar radicals of formula I

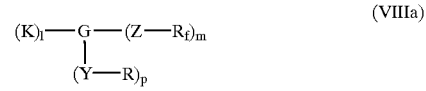

(VIIIa)

with K being a metal complex of formula VIII according to claim 1, G being a radical k) or l) according to claim 1, and Y, Z, R, $R_f$, m, p, and l having the meaning according to claim 1, comprising reacting an amine of formula VIIIa

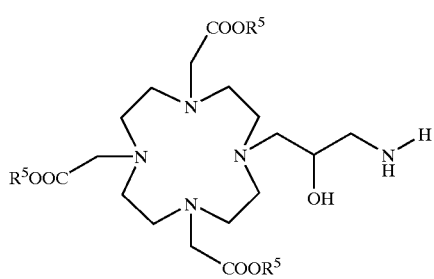

(VIIIa)

in which $R^5$ is a metal ion equivalent of atomic numbers 21–29, 31–33, 37–39, 42–44, 49 or 57–83, or a carboxyl protective group, with an optionally activated carboxylic acid of formula X

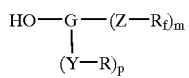 (X)

in which G, R, $R_f$, Y, Z, m and p have the meanings indicated in the claim, in a coupling reaction and optionally subsequently cleaving optionally present protective groups to provide a metal complex of formula I
or
  if $R^5$ has the meaning of a protective group, reacting after cleavage of these protective groups in a subsequent step with at least one metal oxide or metal salt of an element of atomic numbers 21–29, 31–33, 37–39, 42–44, 49 or 57–83, and then, optionally, optionally present acid hydrogen atoms are substituted by cations of inorganic and/or organic bases, amino acids or amino acid amides.

24. A metal complex according to claim 1, wherein R is a glucose, mannose or galactose radical.

25. A metal complex according to claim 1, wherein metal ion equivalent $R^1$ is a gadolinium(III), terbium(III), dysprosium(III), holmium(III), erbium(III), iron(III) or manganese(II) ion.

26. A metal complex according to claim 1, wherein $R^2$ is methyl and $R^3$ is hydrogen.

* * * * *